(12) United States Patent
Abbott et al.

(10) Patent No.: US 8,133,680 B2
(45) Date of Patent: *Mar. 13, 2012

(54) USING LIQUID CRYSTALS TO DETECT AFFINITY MICROCONTACT PRINTED BIOMOLECULES

(75) Inventors: Nicholas L. Abbott, Madison, WI (US); Matthew L. Tingey, Madison, WI (US); Brian H. Clare, Madison, WI (US); Chang-Hyun Jang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 252 days.

This patent is subject to a terminal disclaimer.

(21) Appl. No.: 10/711,517

(22) Filed: Sep. 23, 2004

(65) Prior Publication Data
US 2005/0079486 A1    Apr. 14, 2005

Related U.S. Application Data

(60) Provisional application No. 60/505,114, filed on Sep. 23, 2003.

(51) Int. Cl.
*G01N 33/53* (2006.01)
*G02F 1/13* (2006.01)
(52) U.S. Cl. .................................... 435/7.1; 349/1
(58) Field of Classification Search .................. None
See application file for complete search history.

(56) References Cited

U.S. PATENT DOCUMENTS

| | | | |
|---|---|---|---|
| 4,513,034 A | 4/1985 | Sparer et al. | |
| 4,597,942 A | 7/1986 | Meathrel | |
| 4,902,106 A | 2/1990 | Dijon et al. | |
| 5,352,461 A * | 10/1994 | Feldstein et al. | 424/493 |
| 5,658,491 A | 8/1997 | Kistner et al. | |
| 5,677,195 A | 10/1997 | Winkler et al. | |
| 5,854,864 A | 12/1998 | Knoesen et al. | |
| 5,886,195 A * | 3/1999 | Tang et al. | 549/75 |
| 6,047,095 A | 4/2000 | Knoesen et al. | |
| 6,096,386 A * | 8/2000 | Biebuyck et al. | 427/510 |
| 6,171,802 B1 | 1/2001 | Woolverton et al. | |
| 6,284,197 B1 | 9/2001 | Abbott et al. | |
| 6,284,392 B1 | 9/2001 | Seth et al. | |
| 6,288,392 B1 | 9/2001 | Abbott et al. | |
| 6,292,296 B1 * | 9/2001 | Choi et al. | 359/487 |

(Continued)

FOREIGN PATENT DOCUMENTS

WO    WO 97/03496    2/1994

(Continued)

OTHER PUBLICATIONS

Bernard et al. "Affinity capture of proteins from solution and their dissociation by contact printing" (2001) Nature Biotechnology 19:866-869.*

(Continued)

*Primary Examiner* — Mark Shibuya
*Assistant Examiner* — Christine Foster
(74) *Attorney, Agent, or Firm* — Quarles & Brady LLP

(57) ABSTRACT

The present invention provides methods, devices and kits for detecting a ligand. The methods involve capturing a ligand from a sample with an affinity substrate that includes a receptor for a ligand, transferring captured ligand to a detection surface and detecting the ligand on the detection surface with a liquid crystal. Accordingly, the capture step is decoupled from the detection step.

16 Claims, 22 Drawing Sheets

U.S. PATENT DOCUMENTS

| | | | |
|---|---|---|---|
| 6,364,459 | B1 | 4/2002 | Sharma et al. |
| 6,537,499 | B1 | 3/2003 | Bernard et al. |
| 6,596,346 | B2 | 7/2003 | Bernard et al. |
| 6,600,076 | B1 | 7/2003 | Abbott et al. |
| 6,623,107 | B2 | 9/2003 | Sharma et al. |
| 6,652,885 | B2 * | 11/2003 | Steiner et al. ............. 424/489 |
| 6,692,699 | B2 | 2/2004 | Abbott et al. |
| 6,797,463 | B2 | 9/2004 | Abbott et al. |
| 6,849,321 | B2 | 2/2005 | Abbott et al. |
| 6,852,285 | B2 * | 2/2005 | Abbott et al. ............ 422/82.05 |
| 6,858,423 | B1 | 2/2005 | Abbott et al. |
| 7,745,220 | B2 * | 6/2010 | Abbott et al. .................... 436/4 |
| 2001/0004526 | A1 | 6/2001 | Everhart et al. |
| 2001/0013294 | A1 | 8/2001 | Bruno et al. |
| 2002/0004216 | A1 | 1/2002 | Abbott et al. |
| 2002/0028451 | A1 | 3/2002 | Abbott et al. |
| 2002/0054188 | A1 | 5/2002 | Sharma et al. |
| 2002/0055093 | A1 | 5/2002 | Abbott et al. |
| 2002/0098364 | A1 | 7/2002 | Bernard et al. |
| 2002/0142453 | A1 | 10/2002 | Abbott et al. |
| 2002/0164604 | A1 | 11/2002 | Abbott et al. |
| 2003/0099993 | A1 | 5/2003 | Abbott et al. |
| 2004/0091620 | A1 | 5/2004 | Abbott et al. |
| 2004/0161800 | A1 | 8/2004 | Abbott et al. |
| 2005/0079486 | A1 | 4/2005 | Abbott et al. |
| 2005/0079487 | A1 | 4/2005 | Murphy et al. |
| 2005/0106562 | A1 | 5/2005 | Abbott et al. |

FOREIGN PATENT DOCUMENTS

| | | |
|---|---|---|
| WO | WO 97/32202 | 9/1997 |
| WO | WO 97/33737 | 9/1997 |
| WO | WO 97/35198 | 9/1997 |
| WO | WO 98/04652 | 2/1998 |
| WO | WO 99/063329 | 12/1999 |

OTHER PUBLICATIONS

Houseman et al. "Maleimide-Functionalized Self-Assembled Monolayers for the Preparation of Peptide and Carbohydrate Biochips" (2003) Langmuir 19:1522-1531, Published on Web Nov. 13, 2002.*

Tarlov et al. "UV Photopatterning of Alkanethiolate Monolayers Self-Assembled on Gold and Silver" (1993) J. Am. Chem. Soc. 115, 5305-5306.*

Definitions of the term "peptide" from the Britannica Concise Encyclopedia, the Macmillan Dictionary of Toxicology, and the Columbia Encyclopedia, downloaded from http://www.xreferplus.com/entry/5853278, http://ww.xreferplus.com/entry/975638, and http://www.xreferplus.com/entry/4292792, respectively on Mar. 21, 2007.*

Supporting Information for the article by Renault et al. (Agnew. Chem. Int. Ed. 2002, 41, No. 13, 2320-2323) obtained from http://www.angewandte.org on Mar. 21, 2007.*

Bernard, A., et al., "Printing Patterns of Proteins," Langmuir 1998, 14(9), 2225-2229.

Bernard, A., et al., "Microcontact Printing of Proteins," Adv. Mater. 2000 12:1067-1070.

Brake, J.M. and Abbott, N. L., "An Experimental System for Imaging the Reversible Adsorption of Amphiphiles at Aqueous-Liquid Crystal Interfaces" Langmuir 2002 18:6101-6109.

Charych D.H., et al., "Direct colorimetric detection of a receptor-ligand interaction by a polymerized bilayer assembly." Science 1993 261(5121):585-588. Erratum in: Science 1993 261(5127):1375.

Cornell, B.A., et al., "A biosensor that uses ion-channel switches." Nature 1997 387(6633):580-3.

Dancil, K.S., et al., "A Porous Silicon Optical Biosensor: Detection of Reversible Binding of IgG to a Protein A-Modified Surface." J. Am. Chem. Soc. 1999 121:7925-7930.

Dulcey, et al. "Deep UV photochemistry of chemisorbed monolayers: patterned coplanar molecular assemblies." Science. 1991 252(5005):551-4.

Everitt, D.L., et al., "Evolution of a preferred orientation of polycrystalline grains in obliquely deposited gold films on an amorphous substrate" Physical Rev. B 2000 62:R4833-4836.

Geary, J.M., et al., "The mechanism of polymer alignment of liquid-crystal materials." J. Appl. Phys. 1987 62:4100-4108.

Geissler, M., et al., "Microcontact-Printing Chemical Patterns with Flat Stamps." J. Am. Chem. Soc. 2000 122:6303-6304.

Gu, Y., et al., "Anchoring of liquid crystals on surface-initiated polymeric brushes." Chemphyschem. 2002 3(5):448-51.

Gupta, V.K. and Abbott, N. L., "Uniform Anchoring of Nematic Liquid Crystals on Self-Assembled Monolayers Formed from Alkanethiols on Obliquely Deposited Films of Gold" Langmuir 1996 12:2587-2593.

Gupta, V.K., et al., "Optical amplification of ligand-receptor binding using liquid crystals." Science. 1998 279(5359):2077-2080.

Harnett, C.K., et al., "Low-energy electron-beam patterning of amine-functionalized self-assembled monolayers" Appl Phys Lett 2000 76:2466-2468.

Häussling, L.H. and Ringsdorf, H., "Biotin-functionalized self-assembled monolayers on gold: surface plasmon optical studies of specific recognition reactions." Langmuir 1991 7:1837-1840.

Hidber, P.C., et al., "Microcontact Printing of Palladium Colloids: Micron-Scale Patterning by Electroless Deposition of Copper." Langmuir 1996 12:1375-1380.

Kim, S.R., et al., "Orientations of liquid crystals on mechanically rubbed films of bovine serum albumin: a possible substrate for biomolecular assays based on liquid crystals." Anal. Chem. 2000 72(19):4646-4653.

Kim, S.R. and Abbott, N.L. "Manipulation of the Orientational Response of Liquid Crystals to Proteins Specifically Bound to Covalently Immobilized and Mechanically Sheared Films of Functionalized Bovine Serum Albumin" Langmuir 2002 18:5269-5276.

Kumar, A. and Whitesides, G.M., "Features of gold having micrometer to centimeter dimensions can be formed through a combination of stamping with an elastomeric stamp and an alkanethiol "ink" followed by chemical etching" Appl. Phys. Lett. 1993 63:2002-2004.

Kumar, A., et al., "Patterning Self-Assembled Monolayers: Applications in Materials Science" Langmuir 1994 10:1498-1511.

Lahiri, J., et al., Patterning Ligands on Reactive SAMs by Microcontact Printing. Langmuir 1999 15:2055-2060.

Lin, V., et al., "A porous silicon-based optical interferometric biosensor." Science 1997 278(5339):840-3.

Luk, Y.Y., et al., Surface Science, 2004.

Martin, B.D., et al., "Fabrication and Application of Hydrogel Stampers for Physisorptive Microcontact Printing." Langmuir 2000 16:9944-9946.

Miller, W.J., et al., "Planar anchoring of nematic 4-n-pentyl-4'-cyanobiphenyl on self-assembled monolayers formed from alkanethiols on gold." Appl. Phys. Lett. 1996 69(13)1852-1854.

Ouskova, E., et al., "Photo-orientation of liquid crystals due to light-induced desorption and adsorption of dye molecules on an aligning surface." Phys Rev E Stat Nonlin Soft Matter Phys. 2001 64(5 Pt 1):051709. Epub 2001 Phys. Rev. E 2001 64:Art. No. 051709 Part 1.

Pan, J.J. and Charych, D., "Molecular Recognition and Colorimetric Detection of Cholera Toxin by Poly(diacetylene) Liposomes Incorporating $G_{m1}$ Ganglioside" Langmuir 1997 13:1365-1367.

Renault, J.P., et al., "Fabricating Arrays of Single Protein Molecules on Glass Using Microcontact Printing." J. Phys. Chem. B 2003 107:703-711.

Shah, R.R. and Abbott, N.L., "Coupling of the Orientations of Liquid Crystals to Electrical Double Layers Formed by the Dissociation of Surface-Immobilized Salts." J. Phys. Chem. B 2001 105:4936-4950.

Shah, R.R. and Abbott, N.L., "Principles for Measurement of Chemical Exposure Based on Recognition-Driven Anchoring Transitions in Liquid Crystals." Science 2001 293:1296-1299.

Shah, R.R. and Abbott, N.L., "Using Liquid Crystals to Image Reactants and Products of Acid-Base Reactions on Surfaces with Micrometer Resolution" J. Am. Chem. Soc. 1999 121:11300-10.

Skaife, J. J., et al., "Influence of Nanometer-Scale Topography of Surfaces on the Orientational Response of Liquid Crystals to Proteins Specifically Bound to Surface-Immobilized Receptors" Langmuir 2001 17:5448-5457.

Starkey, C.A., et al., "Evaluation of the Recombigen HIV-1 Latex Agglutination Test." Clin. Microbiol. 1990 28(4):819-22.

Tan, J. L., et al., "Microcontact Printing of Proteins on Mixed Self-Assembled Monolayers." *Langmuir* 2002 18:519-523.

Tercero Espinoza, L.A., et al., "Orientational behavior of thermotropic liquid crystals on surfaces presenting electrostatically bound vesicular stomatitis virus." *Langmuir* 2004 20(6):2375-2385.
Tingey, M.L., et al., "Imaging of affinity microcontact printed proteins by using liquid crystals." *Langmuir* 2004 3;20(16):6818-26.
Tingey, M.L., et al., "Patterned Orientations of Liquid Crystals on Affinity Microcontact Printed Proteins," *Adv. Mater.* 2004 16(15):1331-1336.
Tsukruk, V.V. Rinderspacher and F. Bliznyuk, V.N., "Self-Assembled Multilayer Films from Dendrimers." *Langmuir* 1997 13:2171, 2171-2176.
Wanless, E.J. and Christenson, H,.K., *J. Chem. Phys*. 1994 101:4260-4267.
Yan, L., et al., "Patterning a Preformed, Reactive SAM Using Microcontact Printing" *J. Am. Chem. Soc.* 1998 120:6179-6180.
Yan, L., et al., "Patterning Thin Films of Poly(ethylene imine) on a Reactive SAM Using Microcontact Printing." *Langmuir* 1999 15:1208-1214.
Yaroshchuk, O., et al., "Three-dimensional orientational order in the bulk and on the surface of polymer films and its effect on liquid-crystal alignment." *Phys Rev E* Stat Nonlin Soft Matter Phys. 2004 69(1 Pt 1):011702. Epub Jan. 27, 2004.
Chung, Doo-Han et al., *Alignment Mechanism of Nematic Liquid Crystal on Rubbed Polymer Surface Studied by Subsequent Processes of Rubbing and Photoalignment*, Japanese Journal of Applied Physics, vol. 39, Part 2, No. 3 A/B, Mar. 15, 2000, pp. L185-L187.
Cocchi, J.M. et al., *Comparison Between Direct Binding, Competition and Agglutination Assays in the Characterization of Polyclonal Anti-Idiotypes Against Anti-HBs Human Monoclonal Antibodies*, Journal of Immunological Methods, vol. 160, 1993, pp. 1-9.
Gupta, Vinay K. et al., *Using Isotropic, Nematic, and Smectic Fluids for the Study of Self-Assembled Monolayers Formed from Alkanethiols on Gold*, Chemistry of Materials, vol. 8, Issue 7, 1996, pp. 1366-1369.
Harlow, Ed and Lane, David, *Antibodies—A Laboratory Manual*, Cold Spring Harbor Laboratory, 1988, Contents pp. iii-ix.
Kim, Seung-Ryeol and Abbott, Nicholas L., *Rubbed Films of Functionalized Bovine Serum Albumin as Substrates for the Imaging of Protein-Receptor Interactions Using Liquid Crystals*, Advanced Materials, vol. 13, Issue 19, Oct. 2, 2001, pp. 1445-1449.
Kuby, Janis, *Uses for Monoclonal Antibodies*, Immunology, W.H. Freeman and Company, 1992, Chapter 7, pp. 147-151.
Renault, Jean Philippe et al., *Fabricating Microarrays of Functional Proteins Using Affinity Contact Printing*, Angewandte Chemie-International Edition, vol. 41, Issue 13, 2002, pp. 2320-2323.
Rogers, John A. et al., *Printing Process Suitable for Reel-to-Reel Production of High-Performance Organic Transistors and Circuits*, Advanced Materials, vol. 11, Issue 9, 1999, pp. 741-745.
Schmitt, F.J. et al., *Surface Plasmon Studies of Specific Recognition Reactions at Self-Assembled Monolayers on Gold*, Thin Solid Films, vol. 210/211, Issue 1-2, Apr. 30, 1992, pp. 815-817.
Tizard, Ian R., *Veterinary Immunology: An Introduction*, W.B. Saunders Company, 1996, Contents pp. xv-xxiv.
Van Oss, Carel J. and Van Regenmortel, Marc H.V., *Immunochemistry*, Marcel Dekker, Inc., 1994, Contents pp. v-vii.
Xia, Younan et al., *Microcontact Printing with a Cylindrical Rolling Stamp: A Practical Step Toward Automatic Manufacturing of Patterns with Submicrometer-Sized Features*, Advanced Materials, vol. 8, Issue 12, 1996, pp. 1015-1017.
Yang, Jean Y. et al., *Binary Self-Assembled Monolayers: Spectroscopy and Application to Liquid Crystal Alignment*, Microchemistry—Spectroscopy and Chemistry in Small Domains, 1994, pp. 441-454.
Yang, Kun-Lin et al., *Contact Printing of Metal Ions onto Carboxylate-Terminated Self-Assembled Monolayers*, Advanced Materials, vol. 15, Issue 21, Nov. 4, 2003, pp. 1819-1823.

* cited by examiner

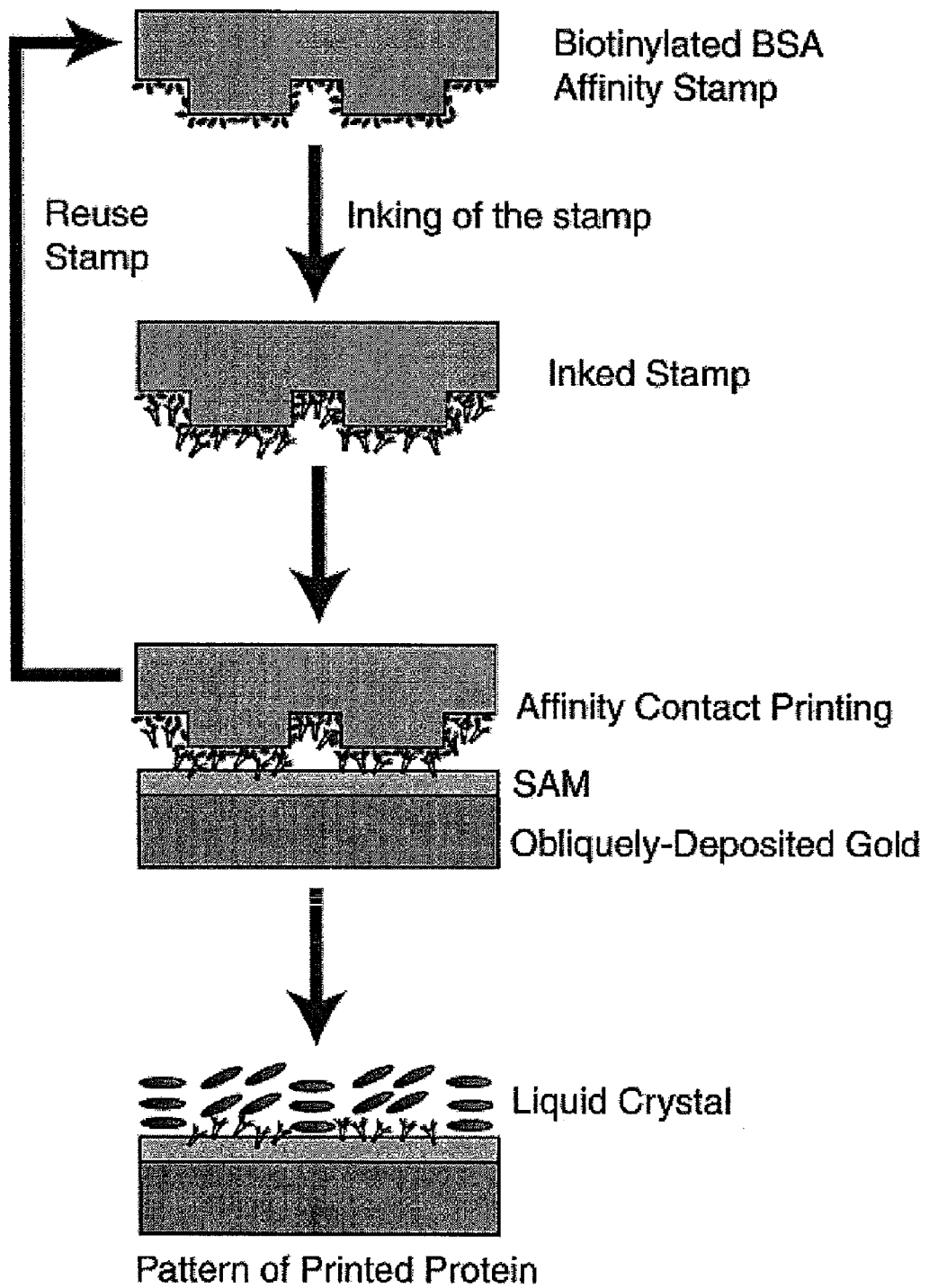
Figure 1.1

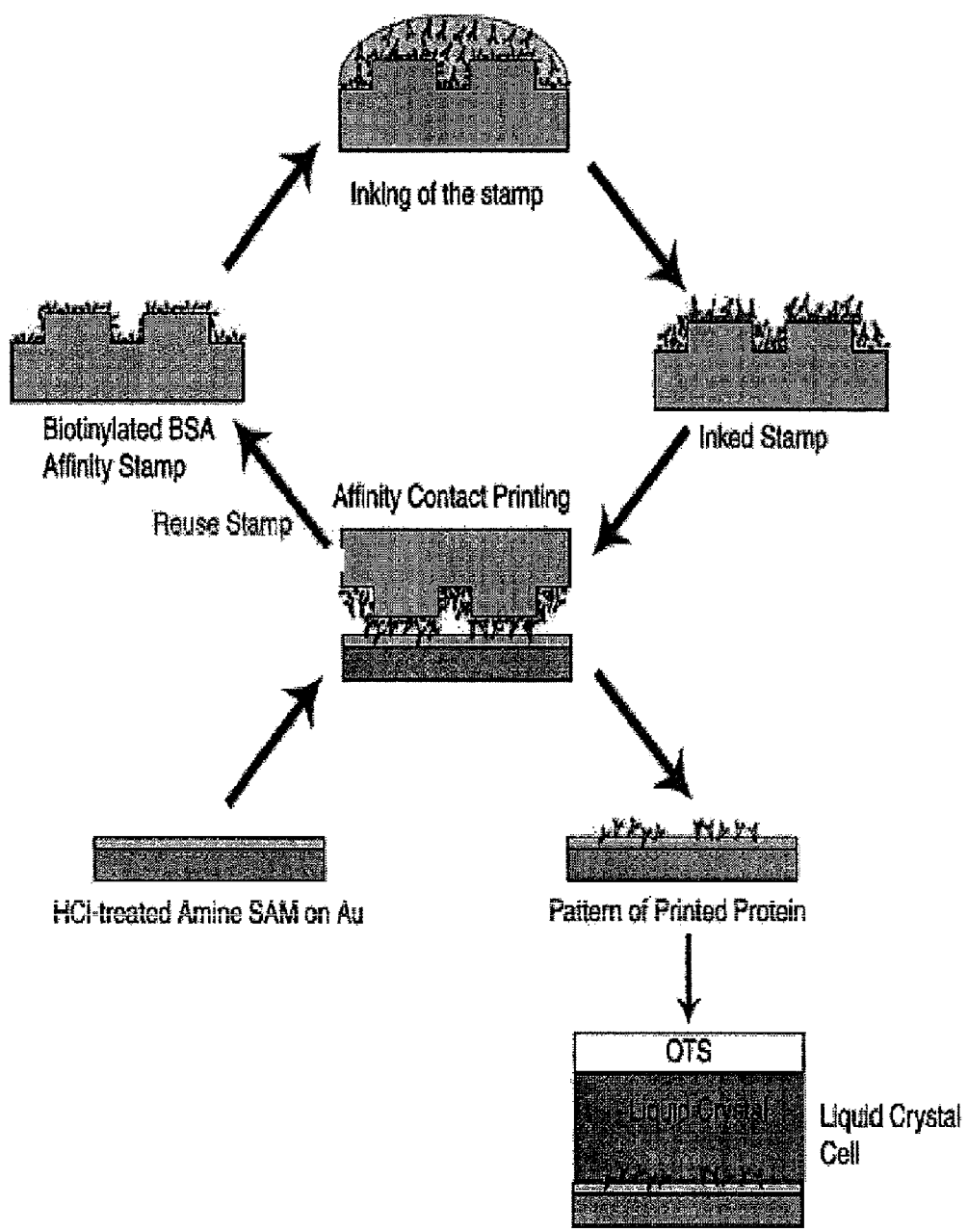
Figure 1.2

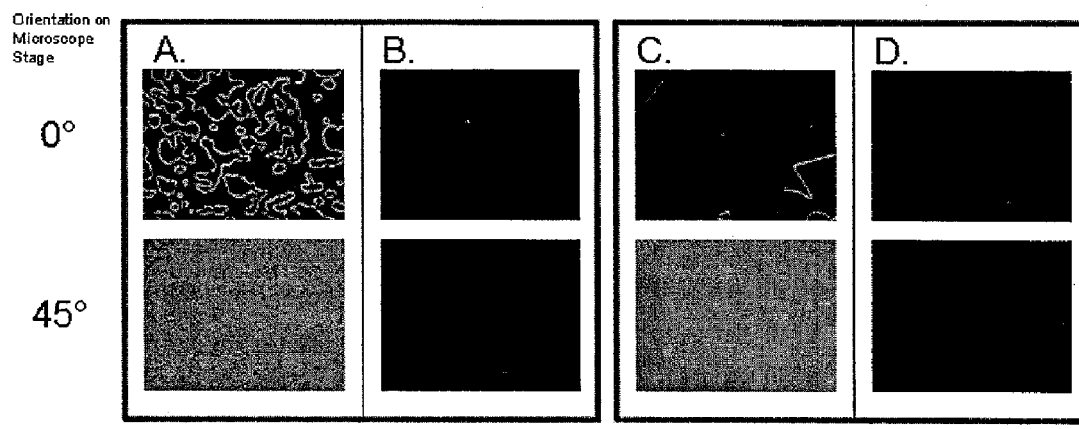
Figure 2
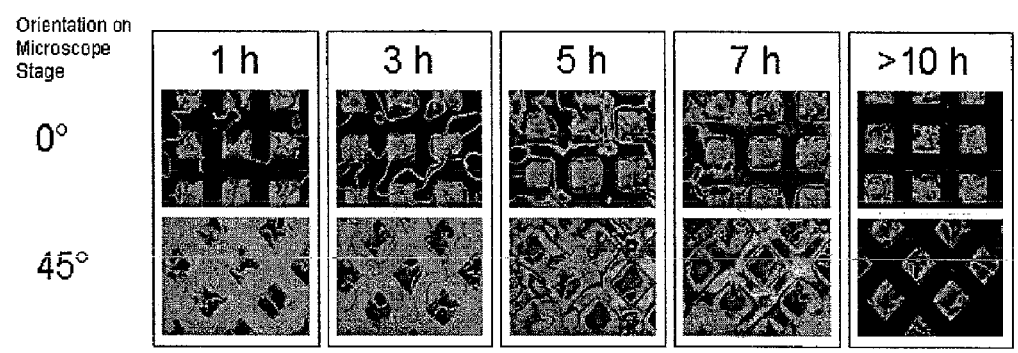
Figure 3.1

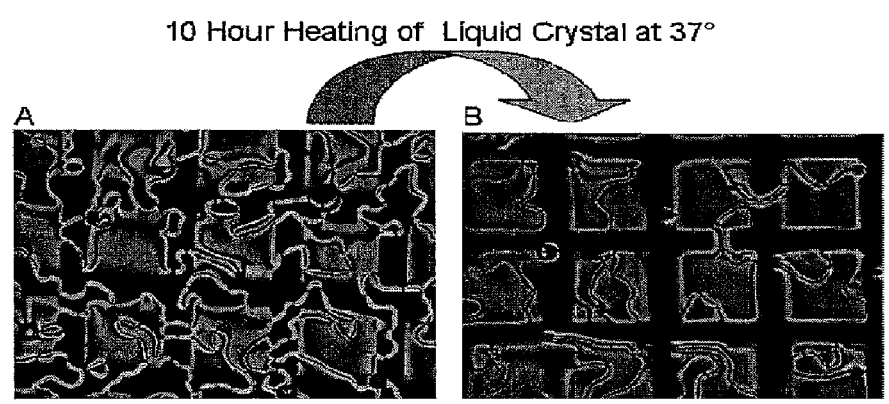
Figure 3.2
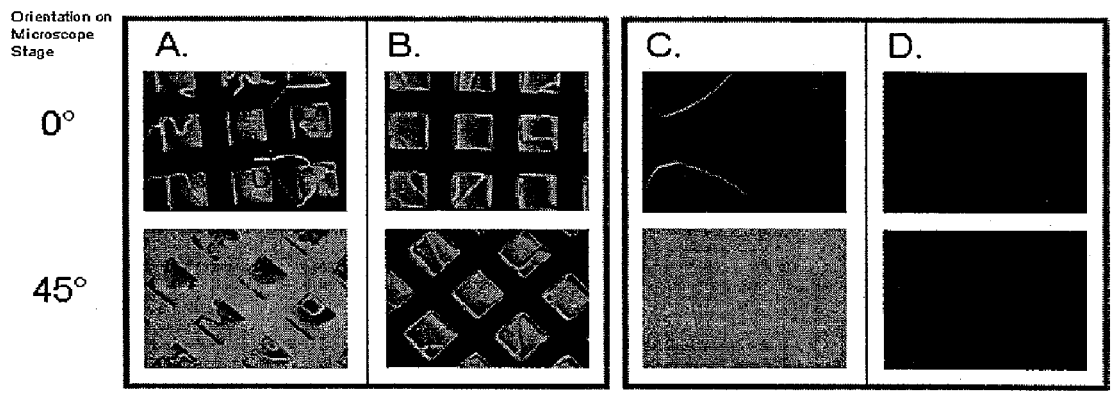
Figure 4

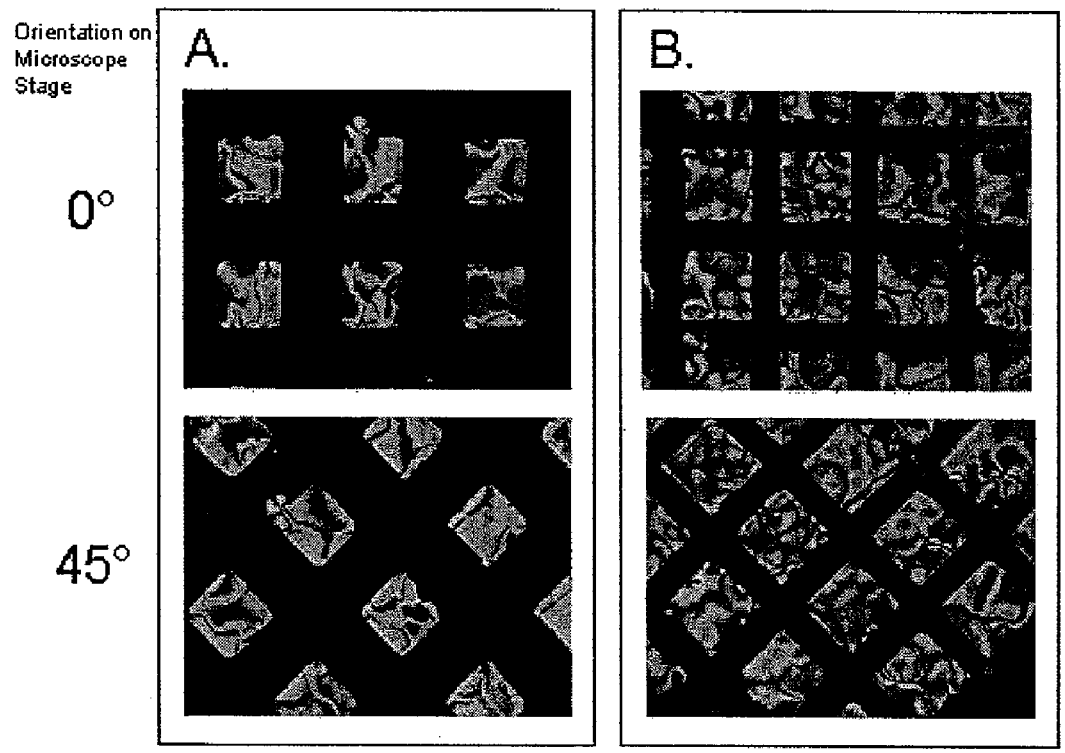
Figure 4.1

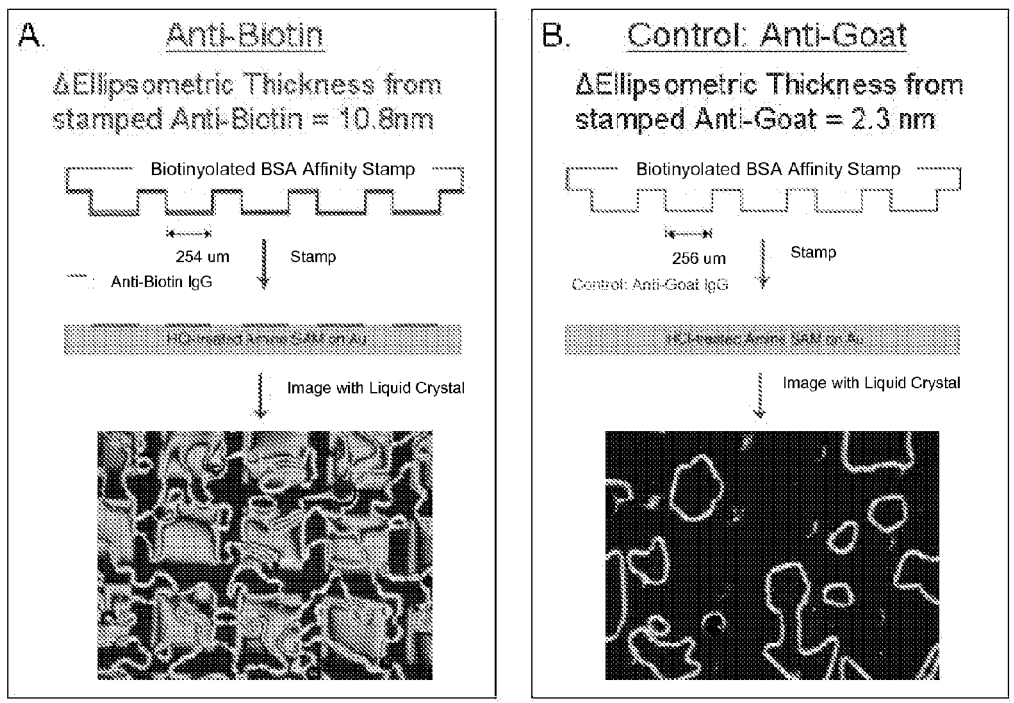
Figure 4.2
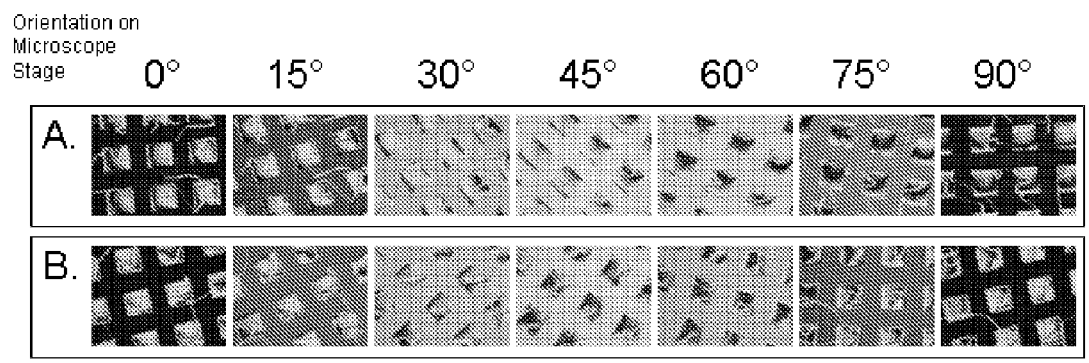
Figure 5.1

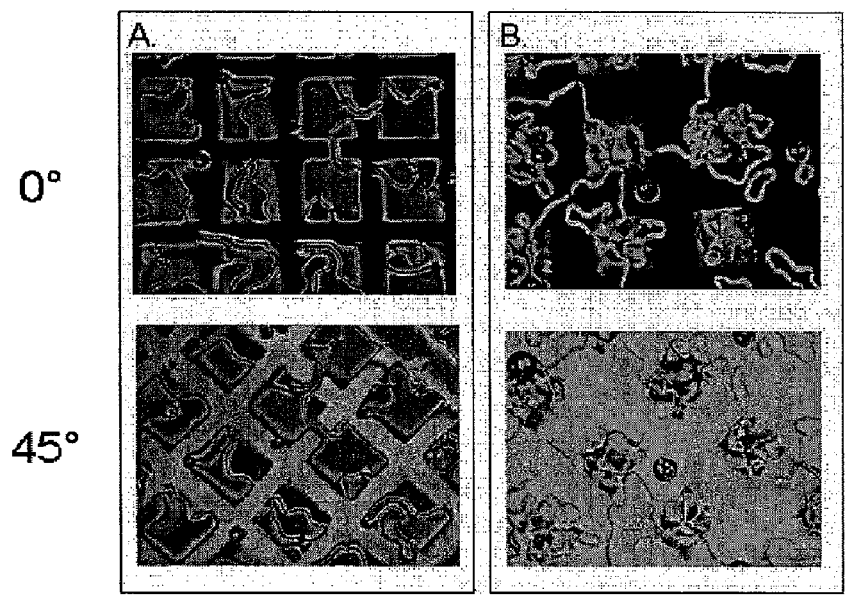
Figure 5.2
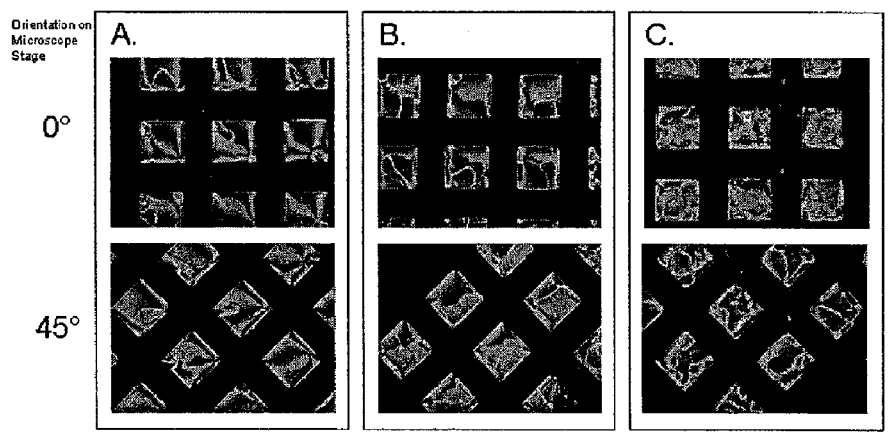
Figure 6.1

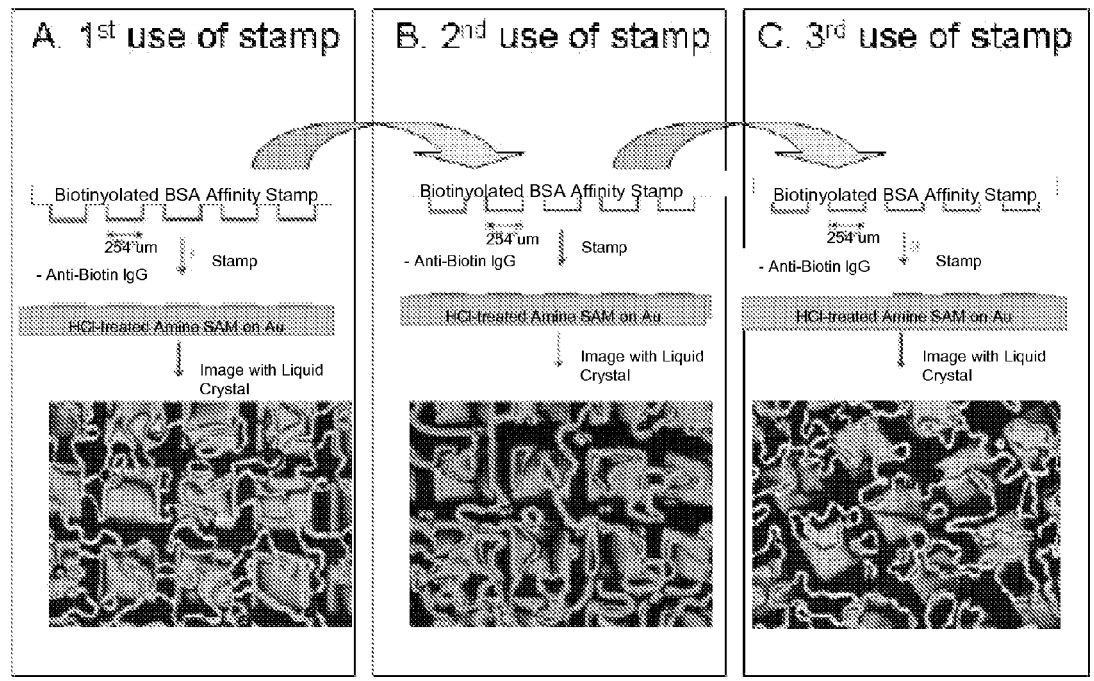
Figure 6.2
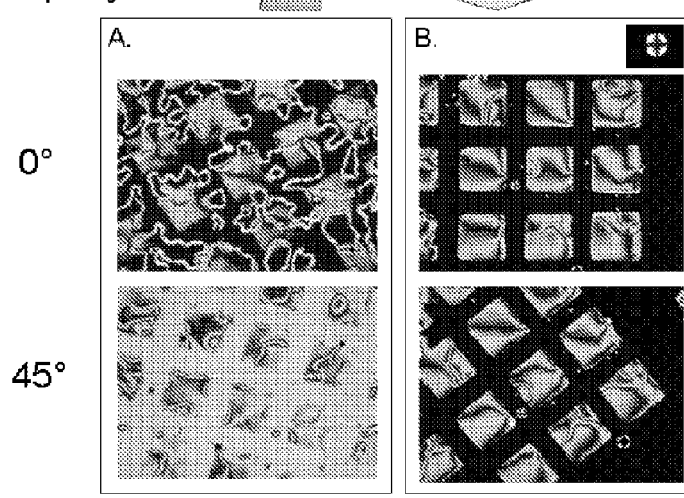
Figure 7

A.
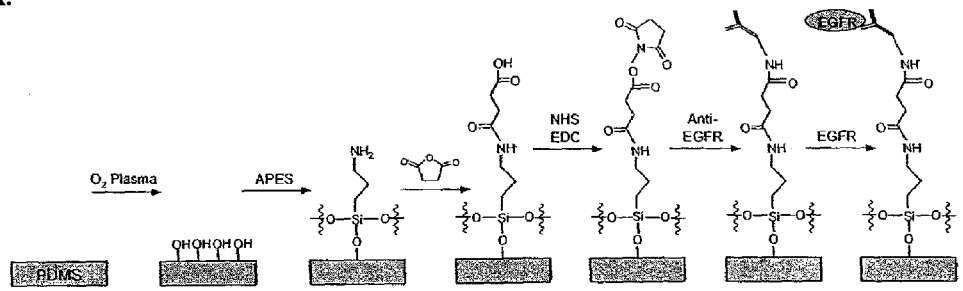
B.
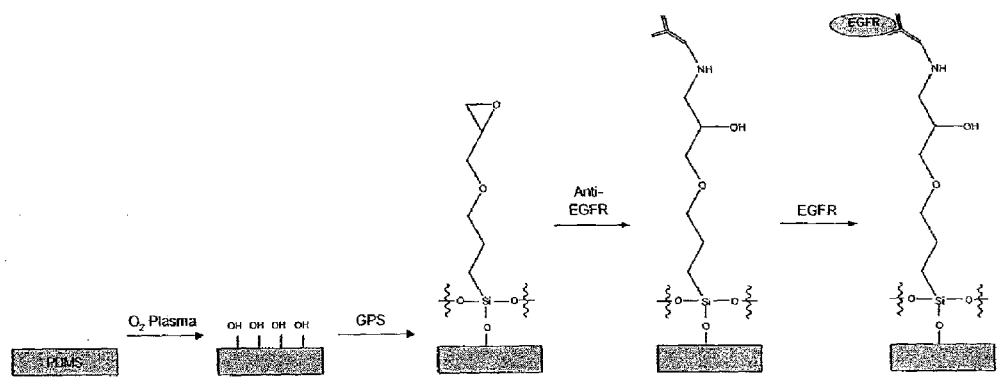
C.
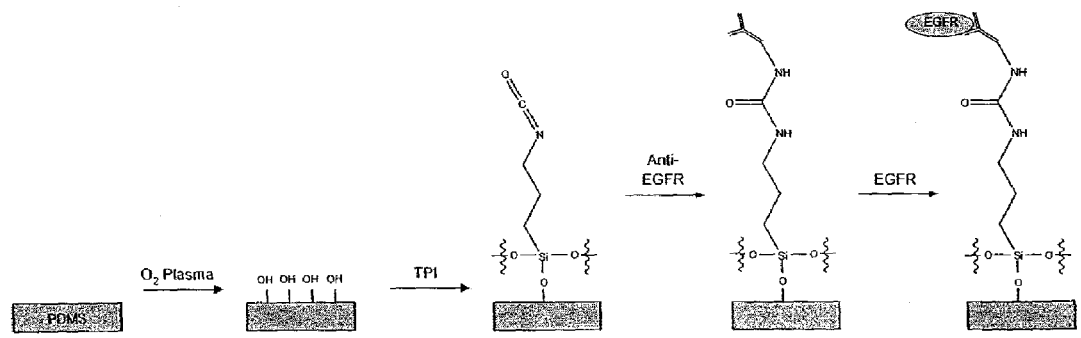
Figure 12

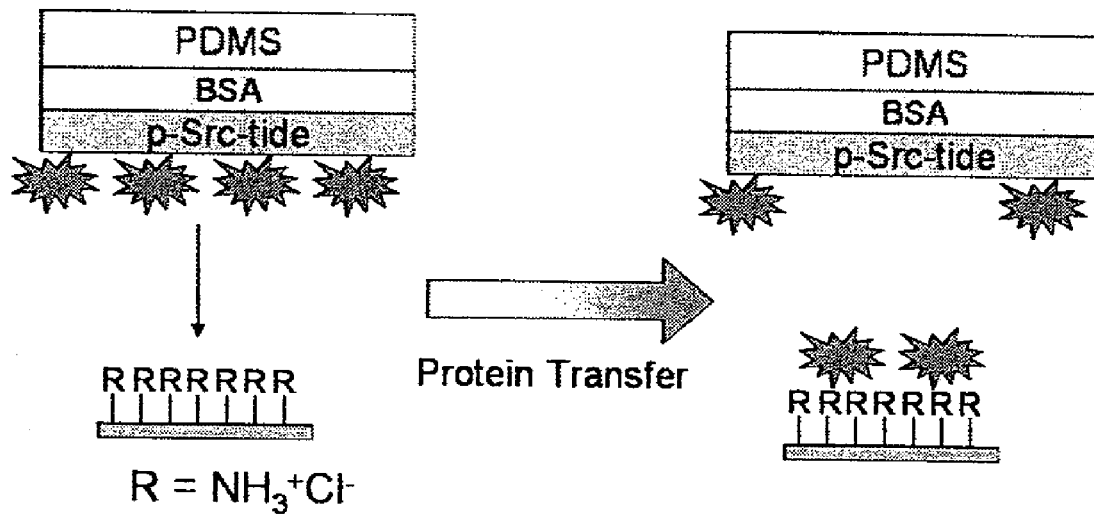
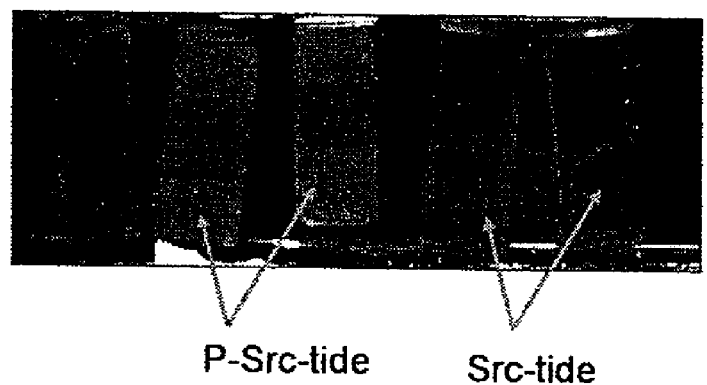
Figure 20

SEQUENCE LISTING

```
<160> NUMBER OF SEQ ID NOS: 2

<210> SEQ ID NO 1
<211> LENGTH: 9
<212> TYPE: PRT
<213> ORGANISM: artificial sequence
<220> FEATURE:
<223> OTHER INFORMATION: synthetic

<400> SEQUENCE: 1

Ile Tyr Gly Glu Phe Lys Lys Lys Cys
1               5

<210> SEQ ID NO 2
<211> LENGTH: 9
<212> TYPE: PRT
<213> ORGANISM: ARTIFICIAL SEQUENCE
<220> FEATURE:
<223> OTHER INFORMATION: synthetic
<220> FEATURE:
<221> NAME/KEY: MISC_FEATURE
<222> LOCATION: (2)..(2)
```

```
-continued

<223> OTHER INFORMATION: phosphorylated
<220> FEATURE:
<221> NAME/KEY:
<222> LOCATION: (2)..(2)
<223> OTHER INFORMATION: Y represents a phosphorylated tyrosine residue

<400> SEQUENCE: 2

Ile Tyr Gly Glu Phe Lys Lys Lys Cys
1               5
```

USING LIQUID CRYSTALS TO DETECT AFFINITY MICROCONTACT PRINTED BIOMOLECULES

RELATED DOCUMENTS

The present invention seeks priority from a U.S. Provisional application No. 60/505,114, filed on Sep. 23, 2003, which is incorporated herein by reference.

GOVERNMENT RIGHTS

This invention was made with United States government support awarded by the following agencies: Office of Naval Research, N00014-99-1-0250; NSF, DMR-0079983; NSF, ECS-0086902; and NIH, 5 T32 GM08349. The United States has certain rights in this invention.

BACKGROUND

Methods for detecting the presence of biological substances and chemical compounds in samples has been an area of continuous development in the field of analytical chemistry and biochemistry. Various methods have been developed that allow for the detection of various target species in samples taken from sources such as the environment or a living organism. Detection of a target species is often necessary in clinical situations before an illness may be diagnosed and a prescribed method of treatment may be undertaken.

Several types of assay currently exist for detecting the presence of target species in samples. One conventional type of assay is the radioimmunoassay (RIA). RIA is a highly sensitive technique that can detect very low concentrations of antigen or antibody in a sample. RIA involves the competitive binding of radiolabeled antigen and unlabeled antigen to a high-affinity antibody. Typically, the labeled antigen is mixed with the antibody at a concentration that just saturates the antigen-binding sites of the antibody molecule. Then, increasing amounts of unlabeled antigen of unknown concentration are added. Because the antibody does not distinguish between labeled and unlabeled antigen, the two types of antigen compete for the available binding sites on the antibody. Measuring the amount of labeled antigen free in solutions, it is possible to determine the concentration of unlabeled antigen. Kuby, J., Immunology, W.H. Freeman and Company, New York, N.Y. (1991), pp. 147-150.

Another type of assay which has become increasingly popular for detecting the presence of pathogenic organisms is the enzyme-linked immunosorbent assay or ELISA. This type of assay allows pathogenic organisms to be detected using biological species capable of recognizing epitopes associated with proteins, viruses and bacteria. Generally, in an ELISA assay, an enzyme conjugated to an antibody will react with a colorless substrate to generate a colored reaction product if a target species is present in the sample. Kuby, J., Immunology, W.H. Freeman and Company, New York, N.Y. (1991), pp. 147-150. Physically adsorbed bovine serum albumin has been used in various such assays as a blocking layer because it has been found to prevent the non-specific adsorption of biological species that might interfere with or result in erroneous assay results.

Although ELISA and other immunosorbent assays are simple and widely used methods, they have several disadvantages. Tizard, 1. R. Veterinary Immunology: An Introduction, W.B. Saunders Company, Philadelphia, Pa. (1996); Harlow, Ed.; Lane, D. Antibodies: A Laboratory Manual, Cold Springs Harbor Laboratory, Cold Springs Harbor, N.Y. (1988); Van Oss, C. J.; van Regenmortel, M. H. V. Immunochemistry, Dekker, New York, N.Y. (1994). Labeled antibodies can be expensive, especially for assays requiring radioactive labels. Additionally, radioactive labels require special handling as radioactive materials are also hazardous. The labeling of a compound, which is the main drawback of these methods, may alter the binding affinity of antibody to analyte. Enzymes are large molecules that may sterically inhibit antibody activity or it may lose enzymatic activity after conjugation to antibodies. Another concern with immunosorbent assays is non-specific binding of proteins to the solid support, antigen, and antibody complexes. This can lead to an increase in background noise, loss of sensitivity, and potentially a false positive test result. Additionally, the immobilization of proteins on the solid support can affect the conformation of the binding sites, leading to a decrease in sensitivity, and possible increase in non-specific binding. For example, physical adsorption of proteins to polystyrene wells occurs due to hydrophobic interactions between the protein and solid support. These interactions can also promote unfolding of the amino acid chains in order to cover the polystyrene surface. This can lead to possible inactivation of the binding sites.

Qualitative diagnostic assays based on aggregation of protein coated beads can also be used for the detection of proteins and viruses. Tizard, I. R. Veterinary Immunology: An Introduction, W.B. Saunders Company, Philadelphia, Pa. (1996): Cocchi, J. M.; Trabaud, M. A.; Grange, J.; Serres, P. F.; Desgranges, C. J. Immunological Meth., 160, (1993), pp. 1; Starkey, C. A.; Yen-Lieberman, B.; Proffitt, M. R. J. Clin. Microbiol., 28, (1990), pp. 819; Van Oss, C. J.; van Regenmortel, M. H. V. Immunochemistry, Dekker, New York, N.Y. (1994). For direct detection of antibodies, antigen is non-specifically adsorbed to the surface of latex beads which are several microns in diameter. The protein-coated beads possess a slight charge which prevents aggregation. Introduction of an antibody specific to the adsorbed protein can link the beads, leading to agglutination. The agglutination can be detected by eye or by other methods such as quasi-elastic light scattering. Visual agglutination assays, however, are not sensitive and measurement by quasi-elastic light scattering requires complex apparatus and is not suitable for use in locations remote from central labs. Furthermore, it is not possible to perform highly multiplexed agglutination assays using microarrays because of the bulk solution methodology of this type of assay.

To overcome the need for labeled proteins, principles based on direct detection of the binding of proteins and ligands have been investigated. Schmitt, F.-J.; Haussling, L.; Ringsdorf, H.; Knoll, W. Thin Solid Films, 210/211, (1992), pp. 815; Hauslling, L.; Ringsdorf, H. Langmuir, 7, (1991), pp. 1837. Surface plasmon reflectometry (SPR) is one such method. SPR is sensitive to changes in the index of refraction of a fluid near a thin metal surface that has been excited by evanescent electromagnetic waves. The binding of proteins to ligands can be detected by examining an increase in the resonance angle or intensity of signal. Typical angular resolution using this method is 0.005° allowing detection of sub-angstrom changes in adsorbed film thickness with SPR. However, care must be taken to ensure that the change in resonance angle is due to binding and not just a change in the bulk solution index of refraction. A thermally stable environment is required due to the dependence of the resonance angle on the index of refraction of the fluid. An increase in temperature from 25° C. to 26° C. in water amounts to a change in the index of refraction by 0.0001. This increase would result in the change in resonance angle of approximately 0.015° or roughly 0.2 nm in the observed height of a protein layer. This temperature stability requirement makes SPR unsuitable for most field applications. In addition, non-specific adsorption of molecules on to or near the sensor surface can lead to false changes in signal, requiring a surface which minimizes non-specific interactions. Therefore, surface plasmon reflectivity is more complex than ELISA, requires laboratory based equipment, and the preparation of a well defined surface.

The use of ion-channel switches for detecting biospecific interactions has been reported. Cornell, B. A.; Braach-Maksvytis, V. L. B.; King, L. G.; Osman, P. D. J.; Raguse, B.; Wieczorek, L.; Pace, R. J. Nature, 387, (1997), pp. 580. In a device using ion channel switches, a tethered lipid membrane incorporating mobile ion channels is separated from a gold electrode surface by an ion reservoir. The gold surface serves as an anchor for the membrane and acts as an electrode. Within the membrane are upper and lower ion channels. In order to become conductive, the outer and inner ion channels must align and form a dimer. Membrane spanning lipids, which help stabilize the lipid membrane, are attached at one end to the electrode surface and are terminated with ligands that extend away from the membrane. The ion channels of the outer layer possess ligands. Unbound, the outer ion channels move freely, occasionally forming dimers with the inner channels, allowing conduction. The binding of a bivalent molecule to both the ion channel and membrane spanning lipid restricts the mobility of the outer ion channel, leading to a measurable decrease in conductivity. However, if a large amount of protein adsorbs to the outer layer, the ion channel mobility presumably would be restricted and a false decrease in conductance could be observed due to non-specific interactions. Additionally, this method requires sensitive devices for detecting the change in conductance. The procedure for fabricating the membranes requires several hours and the membrane stability is limited (must be immersed in solution). More importantly, specific antibodies must be attached to the membrane/channels, requiring separate protein chemistry for each analyte to be detected.

A method based on a porous silicon support that permits optical detection of the binding of specific proteins to ligands has been reported. Lin, V.; Motesharei, K.; Dancil, K. S.; Sailor, M. J.; Ghadiri, M. R. Science, 278, (1997), pp. 840; Dancil, K. S.; Greiner, D. P.; Sailor M. J. J. Am. Chem. Soc., 121, (1999), pp. 7925. The porous areas are typically 1 to 5 m deep and a few square micrometers to millimeters in area. Typical binding times are on the order of 30 minutes followed by rinsing of the surface. Initial work in this area incorrectly reported the detection of extremely low concentrations of analyte. Binding of streptavidin to biotinylated surfaces was initially found to reduce the index of refraction of the porous support, however this was later correctly attributed to an oxidation of the surface. In addition, a change in the effective optical thickness of the film was reportedly observed upon introduction of streptavidin, however they could not differentiate between specific interactions and non-specific adsorption. This method does not require labeled molecules, however, the porous silicon surface is susceptible to oxidation and non-specific adsorption.

The use of polymerized multilayer assemblies for the detection of receptor-ligand interactions has also been reported. Charych, D. H.; Nagy, J. O.; Spevak, W.; Bednarski, M. D. Science, 261, (1993), pp. 585; Pan, J. J.; Charych, D. Langmuir, 13, (1997), pp.1365. Polydiacetylene multilayer films deposited by Langmuir-Blodgett technique change color from blue to red due to a conformational change in the polymer backbone. For example, changes in temperature or pH can cause a shift in color. The response can be controlled and used for protein detection by attaching ligands to the multilayer. Upon binding of a multivalent macromolecule to ligands, stress is introduced into the multilayer assembly. A change in color is seen in the system if sufficient protein is bound, with binding times typically on the order of 30 minutes. This system permits direct detection of receptor-ligand interactions and transduces the events into an optical signal that can be easily measured and quantified. The optical output can be interpreted by eye or analyzed with a spectrophotometer for quantitative conclusions. The use of polymerized multilayer assemblies for the detection of influenza virus has been demonstrated. A significant disadvantage of this method, however, is that it requires multi-valent analyte. Multiple ligands connected to the polymerized multilayer must attach to the same macromolecule. This prevents the use of this method for monovalent molecules (even bead based assays can be performed competitively, not requiring multivalent molecules). Binding of bivalent molecules such as IgG's has not been demonstrated. Furthermore, Langmuir-Blodgett deposition is a process which is difficult to translate from laboratory to commercial scale. As an alternative method to Langmuir-Blodgett deposition, these principles has also been demonstrated using vesicles. However, research based on vesicles, reveals the usefulness of the system to be limited because it is insensitive to the analyte at concentrations below 0.1 mg/ml.

Recently, assay devices that employ liquid crystals have been disclosed. For example, a liquid crystal assay device using mixed self-assembled monolayers (SAMs) containing octanethiol and biotin supported on an anisotropic gold film obliquely deposited on glass has recently been reported. Gupta, V. K.; Skaife, J. J.; Dubrovsky, T. B., Abbott N. L. Science, 279, Mar. 27, 1998, pp. 2077-2079. In addition, PCT publication WO 99/63329 published on Dec. 9, 1999 discloses assay devices using SAMs attached to a substrate and liquid crystal layer which is anchored by the SAM. Although the disclosed liquid crystal-based assay devices which use anisotropic gold films are suitable for use in determining whether a target protein is present in a sample, the preparation of the anisotropic gold film by oblique deposition is difficult. For example, the preparation of the obliquely deposited gold films requires complicated cleaning steps and high vacuum deposition. Further, such assay devices use the same surface for both the capture and detection of the target. Because a single surface is used for both capture and detection, the surface cannot be optimized to perform both functions.

Previous studies have demonstrated microcontact printing to be a broadly useful method to pattern surfaces with organized monolayers of alkanethiols. Microcontact printing and other closely related "soft lithographic" methods[3] have been extended to the patterning of colloids, metal complexes, polymers, proteins, and metal ions. In its simplest form, microcontact printing comprises the "inking" of the surface of polydimethylsiloxane (PDMS) with a solution of the species to be patterned, and conformal contact of the inked PDMS with a second surface. Appropriate design of the physicochemical properties of the surface of the PDMS stamp and the second surface lead to the transfer of the inked species from the PDMS to the second surface. For example, proteins adsorbed to the surface of a PDMS stamp will be transferred to a second surface when the second surface possesses a surface energy that is higher than that of PDMS. This method permits the patterning of proteins on surfaces and has been exploited to prepare surfaces for biomolecular assays and for patterned cell culture.

Although many of the conventional assay methods described above work very well to detect the presence of target species, many conventional assay methods are expensive and often require instrumentation and highly trained individuals, which makes them difficult to use routinely in the field. Thus, a need exists for assay devices and systems which are easier to use and which allow for evaluation of samples in remote locations.

SUMMARY OF THE INVENTION

One embodiment of the present invention provides a method for detecting a ligand comprising: (a) contacting a sample having or suspected of having a ligand with an affinity substrate (inking), wherein the affinity substrate comprises a receptor capable of specifically binding to the ligand; (b) contacting the affinity substrate with a detection surface (stamping), wherein at least a portion of the ligand which is bound to the receptor is transferred to the detection surface; and (c) detecting presence of the ligand on the detection surface, wherein the detection surface further comprises a liquid crystal. This method further comprises step (d) for washing the affinity substrate after step (a); step (e) for washing the detection substrate after step (b), or both steps (d) and (e).

In this method, the receptor or ligand may include a biomolecule, a biomolecule recognition agent, a peptide, a polypeptide, a protein, a carbohydrate, a toxin, a metal, a heavy metal, a chelator, a pathogen, a virus, a bacterium, a mammalian cell or part of a mammalian cell, a nucleic acid, a nucleic acid analogs or mimic, a sugar, antibodies or functional fragment thereof, an organic molecule, a lipid, a phospholipid, a drug, a chemical agent, a pesticide, a herbicide, or a fragment thereof.

In the described methods, the affinity substrate comprises a polymer, a silica material, a metal or a metal oxide. Preferably, the affinity substrate comprises polydimethylsiloxane (PDMS). In a preferred embodiment, the PDMS stamp is further peptide-terminated. The peptide-terminated PDMS stamp is capable of detecting a phosphorylated peptide. In another preferred embodiment, the PDMS stamp is further antibody-terminated. The antibody-terminated PDMS stamp is capable of detecting a protein.

In the method, the receptor is bound to the affinity substrate via one or more linking moieties. Further, the method also provides for quantification of amount of ligand present in the sample.

In another embodiment, the method provides the affinity substrate comprising an array of receptors located in distinct locations. Generally, the receptors in the array have specificities for more than one ligand such that the liquid crystal is capable of detecting presence of more than one ligand. Preferably, the receptors in the array are capable of detecting presence of protein phosphorylation at various residues of Epidermal Growth Factor Receptor (EGFR).

Further, in the method the detection surface comprises a self-assembled monolayer. Preferably, the self-assembled monolayer comprises an amine, alkanethiol or organosulfur compound. Aslo, preferably the self-assembled monolayer is pretreated with an acid prior to step (b).

In another preferred embodiment of the method, contacting the affinity substrate with a detection surface is performed on at least a partially curved affinity substrate. In the most preferred embodiment, the detection surface causes homeotropic anchoring in the absence of captured ligand.

In the present method, the liquid crystal comprises a nematic liquid crystal, smectic liquid crystal, polymeric liquid crystal, lyotropic liquid crystal, chromonic liquid crystal, frustrated liquid crystals, thermotropic liquid crystal, columnar liquid crystal, nematic discotic liquid crystal, calamitic nematic liquid crystal, ferroelectric liquid crystal, discoid liquid crystal, or cholesteric liquid crystal. In a preferred embodiment, the liquid crystal is pretreated by illumination with UV light. In a preferred embodiment, the liquid crystal comprises 4-cyano-4'-pentylbiphenyl (5CB), or doped salt thereof. Further, the orientation of the liquid crystal may be detected optically or electrically.

Another aspect of the invention provides a detection surface comprising a support, a first layer on the support and a self-assembled monolayer on the first layer. Generally, the self-assembled monolayer comprises an amine, alkanethiol or organosulfur compound. Further, the first layer comprises a metal layer, polymer layer or a silane layer. Preferably, the metal layer comprises gold, silver, copper, platinum, palladium, chromium or titanium, or oxides thereof. The detection surface also includes a liquid crystal. In one embodiment, the liquid crystal is thermally annealed to the detection substrate.

Another aspect of the invention provides a method of orienting a liquid crystal on a surface containing a ligand using microcontact printing or affinity microcontact printing. The method comprises the steps of: (a) contacting the ligand to a first surface, wherein the ligand is at least in part attached to the first surface; (b) contacting the ligand-decorated first surface to a second surface, wherein the ligand is at least in part attached to the second surface, such that at least a portion of the first surface is partially curved. Further, in the method, the first surface comprises an affinity substrate having a receptor capable of specifically binding to the ligand. Preferably, the affinity substrate comprises polydimethylsiloxane (PDMS). Yet preferably, the second surface further comprises a self-assembled monolayer.

The self-assembled monolayer may include an amine, an alkanethiol or an organosulfur compound. Also, the ligand or the receptor includes a biomolecule, a biomolecule recognition agent, a peptide, a protein, a carbohydrate, a toxin, a metal, a heavy metal, a chelator, a pathogen, a virus, a bacterium, a mammalian cell or part thereof, a nucleic acid, a nucleic acid analogs or mimic, a sugar, antibodies or functional fragment thereof, an organic molecule, a lipid, a phospholipid, a drug, a chemical agent, a pesticide, a herbicide, or a fragment thereof.

Yet another aspect of the invention provides a kit for detecting a ligand comprising: (a) an affinity substrate; (b) a detection substrate which is separate from the affinity substrate; and (c) a liquid crystal. The kit further includes one or more receptors that are specific for a ligand. The kit also includes a chemical compound that is capable of chemically modifying the detection surface. Preferably, the chemical modification comprises an amine. In the kit, the affinity substrate comprises one or more ligands.

Other objects and advantages of the present invention will be apparent from the detailed description, drawings and claims accompanying the specification

BRIEF DESCRIPTION OF THE DRAWINGS

FIGS. 1.1 and 1.2 depict the experimental steps for detection of affinity microcontact printed proteins using liquid crystals. The biotinylated BSA affinity stamp is inked in a solution of anti-biotin IgG. The inked stamp is affinity microcontact printed onto a SAM on obliquely-deposited gold. Differences in the liquid crystal orientation report the presence of stamped protein.

FIG. 2. Optical images of 5CB sandwiched between amine-terminated SAM and OTS-treated glass slides. A) Amine-terminated SAM, 1 hour in 36° C. oven. B) Amine-terminated SAM, 18 hours in 36° C. C) Amine-terminated SAM pretreated with 0.1 N HCl, 1 hour in 36° C. D) Amine-terminated SAM pretreated with 0.1 N HCl, 18 hours in 36° C.

FIG. 3.1. Time evolution of liquid crystal images of anti-biotin IgG stamped onto amine-terminated SAM pretreated with 0.1 N HCl. In between imaging, the sample was heated at 36° C.

FIG. 3.2. The effect of time/heating on the uniformity of the liquid crystal orientation. A) Optical image 1 hour after making the liquid crystal cell. B) Optical image of same liquid crystal cell after heating the sample at 37° C. for 10 hours.

FIG. 4. Optical images of liquid crystal response to affinity microcontact printed IgGs using biotinylated BSA affinity stamps. The affinity stamp is an array of 300 μm square pegs. A) Anti-biotin IgG, 1 hour cool. B) Sample in A heated at 36° C. for 8 hours. In the regions without stamped protein, the liquid crystal changes from planar to homeotropic alignment. C) Anti-goat IgG (control), 1 hour cool. D) Sample in C heated at 36° C. for 8 hours. The liquid crystal changes from planar to homeotropic alignment.

FIG. 4.1. Optical images of liquid crystal response to microcontact printed anti-biotin IgG. A) Microcontact printing onto amine-terminated SAM on gold deposited at 0° (isotropic). B) Microcontact printing onto glass functionalized with aminopropyltriethoxysilane.

FIG. 4.2. This figure shows the liquid crystal images when anti-biotin IgG and anti-goat IgG (control) are loaded onto a biotinylated BSA affinity stamp. In FIG. 4.2A, the liquid crystal reports the binding of anti-biotin IgG to the biotinylated BSA affinity stamp and the subsequent transfer of protein to the amine SAM substrate. By comparing FIG. 4.2A with the control experiment shown in FIG. 4.2B, it can be concluded that the affinity stamp is specifically capturing and transferring the anti-biotin IgG to the substrate which can be detected using liquid crystals.

FIG. 5.1. Comparison of the liquid crystal response to affinity microcontact printed and microcontact printed IgGs. A) Affinity microcontact printing of anti-biotin IgG. B) Microcontact printing of anti-biotin IgG.

FIG. 5.2: Comparison of the liquid crystal uniformity in the stamped regions for affinity contact printing and microcontact printing of IgGs. A) Affinity contact printing of anti-biotin IgG. B) Microcontact printing of anti-streptavidin IgG.

FIG. 6.1. Optical images obtained when reusing a biotinylated BSA affinity stamp to print anti-biotin IgG. A) 1st use of stamp. B) 2nd use of stamp. C) 3rd use of stamp.

FIG. 6.2. Side-by-side comparison of the optical images discussed in FIG. 6.1.

FIG. 7: A) The optical images of affinity contact printed anti-biotin IgG after the 3rd use of the stamp. These images were taken 1 hour after making the liquid crystal cell. B) These optical images were taken of the same sample after heating the liquid crystal cell for 32 hours at 37° C. The regions on the amine SAM treated with 0.1 M HCl with no protein are now homeotropic.

FIGS. 12A-C: Schematic depictions of reaction schemes for covalent immobilization of biomolecules to a PDMS stamp.

FIG. 20: A. Schematic depicting transfer of labeled protein. B. Optical image of roller-printed surfaces illustrating protein transfer.

DETAILED DESCRIPTION

Figure 8:
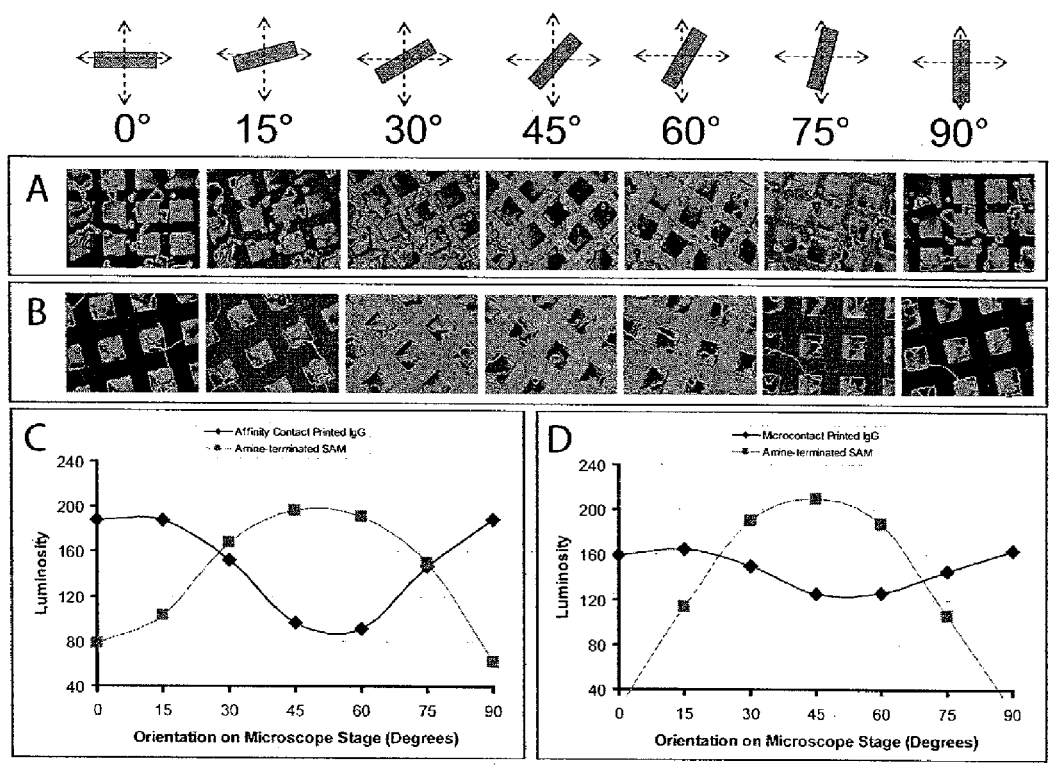
FIG. 8: Optical images (crossed polars) of 5CB in contact with amine-terminated SAMs on which anti-biotin IgG was affinity microcontact printed (A) and microcontact printed (B) in areas having lateral dimensions of 300 μm×300 μm. The luminosity inside and outside the square patterns, measured as a function of the sample orientation on the microscope stage, is graphed for affinity microcontact printing (C) and microcontact printing (D).
Figure 9:
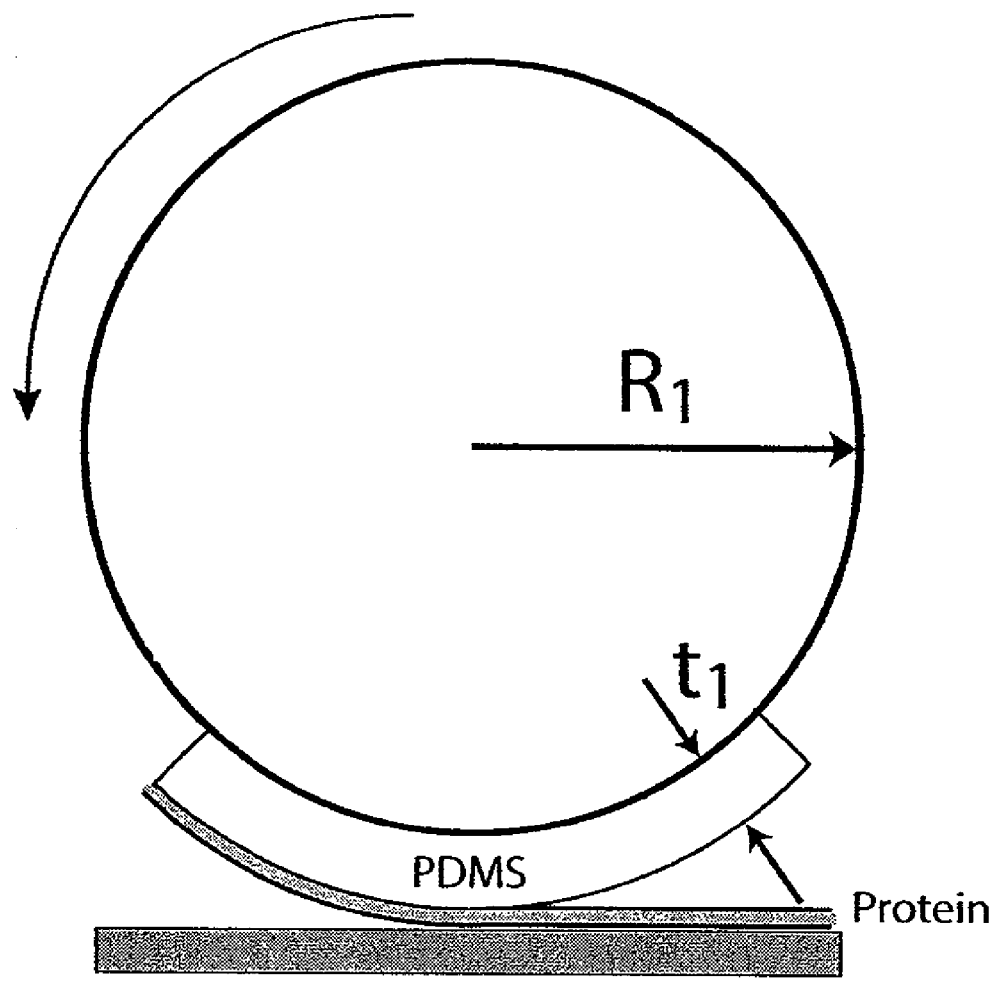
FIG. 9: Schematic illustration of microcontact printing of proteins using a PDMS stamp mounted on a cylindrical support. ($R_1$=14 mm, $t_1$=4 mm)

The present invention provides a method for detecting a ligand or analyte of interest using affinity microcontact printing of the ligand and visualizing the presence or absence of ligand with a liquid crystal. Affinity microcontact printing is used to specifically capture a ligand from a sample, and then "stamp" the ligand onto a detection surface. The present methods involve contacting a sample having or suspected of having the ligand with an affinity substrate. The affinity substrate includes a receptor that is specific for the ligand or an affinity molecule that is specific for the analyte of interest. If ligand is present in the sample, some of the ligand can bind to the receptor so that it can be removed from the sample for isolation or detection. This step is also referred to as "inking" the stamp. Typically, the affinity substrate will be incubated with the sample for a desired period of time, such as several hours. This incubation period can differ depending upon the nature of the sample being tested. After the ligand is captured from the sample by the receptor, the affinity substrate is contacted with a detection surface, present on a separate substrate, that allows a portion of the bound ligand to be transferred to the detection surface. This step is also referred to as "stamping" or "printing" the ligand. As will be apparent to the skilled artisan contacting the affinity substrate and the detection surface can be performed manually or in an automated fashion. The presence or absence of any ligand transferred to the detection surface can then be visualized using a liquid crystal. Typically, the liquid crystal is placed on the detection surface after it has been contacted with the affinity substrate and the liquid crystal is visualized. If liquid crystal is heated into an isotropic phase during this step, the isotropic phase should be cooled to form the liquid crystalline phase before imaging. The liquid crystal can also be deposited in the liquid crystalline phase. A disordering or disruption of the liquid crystal typically indicates that ligand is present on the detection surface. However, it is also possible to detect the presence of ligand in a sample by ordering of the liquid crystal by ligand on the surface. If the uniform anchoring of the liquid crystal has been disrupted, then the ligand is present in the sample. Determining whether the uniform anchoring of the liquid crystal has been disrupted may be accomplished by various methods. One such method includes viewing the substrate through polarizers. This can be performed on an automated device such as a plate reader. Electrical methods (e.g., measurement of the electrical impedance of the thin film) can also be used. In other embodiments of the invention, the presence of the ligand on the capture surface will be reported by the liquid crystal assuming a well-defined orientation that is distinguishable from the orientation assumed by the liquid crystal in the absence of the ligand. For example, the orientation of the liquid crystal could be parallel to the surface in the presence of the ligand, and perpendicular to the surface in the absence of the ligand on the surface. In other embodiments, the in-plane orientation of the liquid crystal may change with ligand is present on the surface.

A depiction of this process is illustrated in FIG. 1.1. As can be seen in this figure the affinity stamp is inked in a solution of ligand. The inked stamp is affinity microcontact printed onto a SAM on obliquely-deposited gold. Differences in the liquid crystal orientation report the presence of stamped protein. A more specific procedure used to image affinity contact printed proteins using liquid crystals is shown in FIG. 1.2. In this figure, the amine SAM (self-assembled monolayer) on the gold substrate is treated with 0.1 M HCl for 10 seconds prior to printing (this represents a preferred substrate). To make the gold substrate, gold has been deposited onto a clean glass microscope slide at a 45° angle. The affinity stamp is placed into contact with the Amine SAM on the gold substrate for 30 seconds, then peeled off. The PDMS stamp was formed from a silicon master to give pegs that are 256 µm squares. The liquid crystal cell is then assembled by sandwiching liquid crystal between two substrates. The first substrate is the gold that has been printed with protein. The second substrate is an OTS (octadecyltrichlorosilane) functionalized glass slide. This substrate gives homeotropic anchoring of the liquid crystal. The sample is slowly cooled from 37° C. to room temperature for >40 minutes.

As can be seen from FIG. 1.1, in order to facilitate visualization of the detection surface, the detection surface can be part of a liquid crystal assay cell where the liquid crystal is sandwiched between two substrates. Typically, the first substrate of the cell will be the detection surface and the second substrate will be an optically clear material, preferably one that can give homeotropic anchoring of liquid crystal. A suitable example of a second substrate is OTS (octyltrichlorosilane). In other embodiments of the invention, the second surface will be an interface between the liquid crystal and air. That is, a thin film of liquid crystal will be spread over the capture surface to image the captured protein.

As will be apparent to the skilled artisan, the molecular interaction between the detection surface and the bound ligand should be strong enough such that a detectable amount of the ligand can be transferred to the detection surface despite any ligand-receptor interaction occurring on the affinity substrate. Typically, ligand transfer from the affinity substrate to the detection surface usually simply involves contacting the surface of the two different substrates. Pressure can also be applied to either or both of the two substrates in order to facilitate ligand transfer. As will be understood by the skilled artisan, ligand removal from the affinity substrate occurs by disrupting or interfering with the interaction between the ligand and receptor thus isolating the ligand. Because ligand transfer depends on the nature of the ligand, receptor and detection surface, transfer can be enhanced or facilitated by heating, cooling, repeated contact between the affinity substrate and the detection surface, rinsing or the like. Transfer can also be enhanced by pretreatment of the affinity substrate or detection surface with a transfer agent. One example of a transfer agent is an acid. The present methods can also involve washing the affinity substrate after it has been contacted with the sample to facilitate the removal of any non-specifically bound contaminants which can increase the yield or purification of the isolate ligand.

Generally, the ligand(s) that is (are) transferred to the detection surface are associated with the detection surface non-specifically. As such, the detection surface can be treated so that it can bind any ligand in a non-specific manner and lacks any structures or molecules that specifically bind to a ligand. As such, the detection surface is not ligand specific, in contrast to the affinity substrate which is specific for a particular ligand or ligands.

By utilizing an affinity substrate that is separate from detection surface, the ligand capture step can be uncoupled from the detection step. This uncoupling allows for numerous advantages over systems that use a single surface to both capture and detect the presence of ligand. For example, the affinity substrate and detection surface can be independently optimized to provide for enhanced sensitivity and/or selectivity. The affinity substrate and the detection surface can also be made of different materials that are particularly suited to their intended environments. For instance, where the ligand or analyte of interest is typically present in extreme environments, such as highly acidic, highly basic, high or low temperatures or the like, then the affinity substrate can be made of a material that resists physical and chemical degradation in that environment. In some embodiments, a wide variety of methods can be employed to immobilize the receptors on the surface of the stamp to maximize the amount of ligand captured on the stamp. These methods may involve the use of polymeric brushes, hydrogels, protein multilayers, polyelectrolyte films, protein A, streptavidin and other molecular layers known to those skilled in the art of immobilizing receptors on surfaces. In contrast, the detection surface can be made of a relatively more delicate material that enhances detection of ligand but would not necessarily survive the conditions in which the ligand is found. A wide variety of substrates can be used, including but not limited to, rubbed polymer films, surfaces with topography, surfaces prepared by nanomolding and micromolding, surfaces prepared to orient liquid crystals by treatment with UV light (photo-alignment layers), surfaces treated with polymeric brushes, surfaces stretched to align liquid crystals, rubbed protein films, obliquely deposited organic and inorganic materials, mechanically polished surfaces, inorganic films supporting organic monolayers and multilayers, surfaces on which polymers and polyelectrolytes have been adsorbed, glass surfaces, glass surfaces treated with silane-based monolayers, gold and silver films on organosulfur compounds have been adsorbed. Those skilled in the art will recognized that surfaces for use in this invention are not limited to those listed above. Additionally, both the affinity substrate and the detection surface can be reused, resulting in decreased cost. Affinity substrates that have been contacted with sample can also be contacted with the detection surface one or more times in order to concentrate ligand on the detection surface, allowing for detection of lower levels of ligands. The treated affinity substrate can also be contacted with multiple detection surfaces allowing for multiple detections to be performed from a single sampling. It is also possible to preserve spatial information regarding the location of a target molecule in a sample, which could be very useful when detecting proteins from histological sections (imaging) or detecting species from a spatially resolved pattern of molecules.

Ligand or Analyte and Receptor or Affinity Molecule

As will be apparent to one skilled in the art, the affinity substrate can include an affinity molecule that is specific for an analyte of interest instead of the receptor. Some receptors will capture a range of molecules belonging to a class of interest. As such, the identity if the ligand or analyte of interest is not particularly limited as long as there is a receptor or affinity molecule which is capable of specifically capturing the ligand or analyte. The receptors may comprise various suitable biomolecules and biomolecule recognition agents, including peptides and polypeptides; carbohydrates; toxins; metals, such as heavy metals; chelators; pathogens, including viruses and bacteria; nucleic acids, such as RNA and DNA, their analogs and mimics; biotin; avidin; sugars; antibodies; FAB and FAB' or other active fragments of antibodies such as, but not limited to, immunoglobulins, such as but not limited to, IgG; small organic molecules, e.g., drugs, chemical agents, pesticides, herbicides and the like. Immunoglobulins including IgG, IgA, IgM, IgD, and IgE, and fragments of immunoglobulins are preferred receptors, and IgG and fragments of IgG are especially preferred receptors. Examples of biomolecules and ligands that can be used in the present invention are also discussed in U.S. Pat. Nos. 6,171,802 and 6,284,197, which are incorporated herein by reference.

The receptor may be evenly distributed over the surface of the affinity substrate. In some embodiments, substantially all of the receptor may be located on the top of the topographical features. This may be accomplished by coating the affinity substrate with blocking compound, such as BSA, and then removing the blocking compound from the top of the topographical features, such as by wiping or scraping, and treating the surface with the receptor.

As with the ligand, the receptor portion of the affinity substrate is also not particularly limited. Any of the ligands described above can also be used for receptors so that the receptor becomes the ligand and vice versa.

Affinity Substrate

As discussed above, the affinity substrate is used to capture the ligand or analyte of interest and transfer the captured ligand to the detection surface. In order to perform these functions, the affinity substrate includes a ligand or affinity molecule associated with a support. In preferred embodiments, the affinity molecule is covalently bound to the support, either directly or through one or more linking moieties, although they are not required to be covalently bound as long as the affinity substrate can effectively capture and transfer ligand. In cases where the affinity molecule is not covalently attached, the affinity molecule and ligand may be transferred to the detection surface for detection of the presence of the ligand. A wide variety of materials may be used as supports in the affinity substrate and is not particularly limited as long as the selected receptor or affinity molecule can be associated with the substrate. Preferred supports include polymers and silica-containing materials with surfaces for reaction with surface modifying compounds or agents.

The affinity substrate may be formed from various materials including any polymer that is stable under the sampling conditions, for example in aqueous media. Examples include, but are not limited to, polydimethylsiloxane, polystyrene, polymethylmethacrylate, polycarbonate, polycyanoacrylate, polyurethane, polyolefins, and polyimides. One preferred group of substrates are formed from polyurethane, polycyanoacrylate, or polystyrene. Polystyrene is an especially preferred substrates for use in the present invention. An alternative is a spin-on glass, e.g., silica material formed through wet chemical, sol-gel methods, such as tetraethoxysilane (TEOS). This inorganic material may be molded. Because it is a glass presenting hydroxyl groups, one could treat the surface using silane chemistry (e.g., 3-aminopropyl triethoxysilane (APES)). Because it is rigid, it may be less prone to "rounding" of grooves, etc. than an elastomer. Silicone elastomers can also be used. Examples of silicone elastomers suitable for use as stamps include those formed from precursors including the chlorosilanes such as methyl chlorosilanes, ethyl chlorosilanes, and phenyl chlorosilanes, and the like. A preferred silicone elastomer is polydimethylsiloxane (PDMS).

Although the affinity substrates described herein can be made of a featureless, flat piece of material, preferably the affinity substrate will have topological features, such as ridges or plateaus. The topological features can be of various geometries, e.g., square, rectangular, triangular, circular, semicircular or combinations thereof, as desired, and typically will be formed somewhat rounded or wedge shaped at nano-dimensions. The topographical features can have any desired dimensions and can be sized to be readily observable by microscopy. Typical features will be on the micrometer scale and can range from 1 to 100 µm. For example, the topographical features will be square shapes that are 10 to 20 µm on a side. Affinity substrates that employ more than one area can be used to present an array of receptors, which can have the same or different specificities, to a sample. When the receptors have different specificities, each topographical feature will have receptors that are specific for a single ligand and the topographical features can have different shapes in order to facilitate ligand identification. For example, a receptor for a specific DNA ligand can be associated with a circular topographical feature and a receptor for a protein ligand can be present on a square feature so that a circular disruption of the liquid crystal on the detection surface would indicate the presence of the DNA ligand and the presence of a square disruption would indicate the presence of the protein.

The topography of the substrate and detection region of the detection apparatus may be modified by coating at least a portion of the affinity substrate with an inorganic material such as, but not limited to, an oxide of silicon, an oxide of a metal, a metal, combinations of these. Preferably, this is accomplished using vacuum deposition techniques. Silver and gold are particularly preferred inorganic materials for use in such topography modification, and gold is especially preferred. When at least a portion of the detection region is coated with gold or silver, they may be treated with an organosulfur compound such as a mercaptan or disulfide which will bind to the metal surface.

The substrate with microstructures formed can be produced by various manufacturing processes. In one suitable process, a mold is formed by conventional micromachining processes, e.g., in a silicon workpiece, which then has a liquid polymer applied to it which is solidified. Mechanical embossing of a polymer similar to that used in the production of compact discs and holographic gratings may also be used. A hot, hard master is pressed into a polymer sheet heated to about its glass transition temperature, transferring the relief in the master to the polymer, and the polymer is then cooled below its glass transition temperature before removal of the master. Substrates may also be prepared by photopolymerization techniques, lithography or the like.

In one preferred method for preparing a substrate, a silicon or other master is used to form a polydimethylsiloxane (PDMS) or other elastomeric replica. Preferably, a fluorine-containing compound is applied to the surface of the silicon master prior to making the elastomeric replica such that removal of the elastomeric replica is easier. The elastomeric replica is then preferably used as a master to form a replica from a thermally-curing material such as, but not limited to epoxide or more preferably from a ultraviolet-curing material such as, but not limited to polyurethane, polycyanoacrylate, or polystyrene. Polystyrene is an especially preferred material for use in forming such a polymeric replica.

Discussed below is a reaction scheme illustrating the steps that are preferably used in a process for chemically immobilizing a biochemical blocking layer onto the surface of a support for use in a liquid crystal assay device. Generally, a support is generally first treated with a surface modifying agent having one end bearing a reactive group capable of reacting with a functional group on the surface of the support and another end having a reactive group capable of reacting with a reactive group on one end of the bifunctional spacer compound. In preferred surface modifying compounds, the reactive group capable of reacting with the functional group of the support includes functionalities such as, but not limited to, a halogen-silicon bond or an alkoxy-silicon bond. These functionalities react with the chemical groups on supports such as silica wafers or glass to form a covalent bond tethering the silicon compound to the surface of the support. Preferred surface modifying compounds also include an end with a reactive group capable of reacting with a reactive group on one end of the bifunctional spacer compound. Preferred such reactive groups on the surface modifying compound include, but are not limited to alkylamines. Thus, preferred surface modifying agents are silicon compounds which include a silicon atom; at least one alkoxy group bonded to the silicon atom through an oxygen-silicon bond; and an aminoalkyl group bonded to the silicon atoms through a carbon-silicon bond. More preferred surface modifying compounds include aminoalkyltrialkoxysilanes such as those having aminoalkyl groups having from 2 to 8 carbon atoms. An especially preferred such compound is aminopropyltriethoxysilane (APTS).

Those skilled in the art will recognize that alkoxy groups such as methoxy, propoxy, butoxy, and pentoxy may be used in place of the ethoxy groups. Additionally, those skilled in the art will recognize that other silanes such as, but not limited to, aminoalkyldialkylchlorosilanes, sulfhydryl-terminated silanes such as 3-mercaptopropyltrimethoxysilane, and silanes with double bonds such as allyltrichlorosilane and allyltrialkoxysilanes may also be used as the surface modifying compound. Those skilled in the art will recognize that silanes with sulfhydryl groups such as 3-mercaptopropyltrimethoxysilane would react with both the surface chemical groups on the support and with the biochemical blocking compound via formation of a disulfide bond between the sulfhydryl group on the silane and a sulfhydryl group on the protein. Thus, a bifunctional spacer compound might not be necessary if such a surface modifying compound were employed. However, if desired, a heterobifunctional cross linker such as n-succinimidyl 3-(2-pyridylthio)propionate (SPDP) or succinimidyloxycarbonyl-methyl-(2-pyridylthio) toluene (SMPT), or succinimidyl-4-(N-maleimido-methyl) cyclohexane-1-carboxylate (SMCC) or maleimidobenzoyl-N-hydroxysuccinimide ester (MBS) could be used with such a sulfhydryl containing surface modifying silicon compound.

Reaction between the surface modifying compound and the support produces a support with a modified surface that can be activated by reaction with the bifunctional spacer compound. Because water in the reaction mixture may result in an undesirable reaction with the surface modifying compound, the reaction between the surface modifying compound and the support is preferably conducted using anhydrous solvents and conditions although those skilled in the art will recognize that the presence of some water will be tolerated.

In the process for chemically immobilizing a receptor on the surface of a support, a reactive group on one end of a bifunctional spacer compound or bifunctional activating agent is typically reacted with the modified surface to activate the surface forming an activated modified surface of the support. Preferred bifunctional spacer compounds have two ends that may have similar or different functional groups. Preferably such bifunctional spacer compounds will have leaving groups at each of two ends so that one end will react with a group such as an amine on the biochemical blocking compound and the other end will react with a group such as an amine group on the tethered surface modifying compound. Preferred bifunctional spacer compounds or activating agents include structures having the following formula:

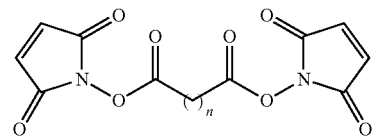

where n is an integer having a value ranging from 1 to 20, more preferably ranging from 2 to 10, or even more preferably ranging from 5 to 8. Most preferably, the bifunctional spacer compound or activating agent is disuccinimidyl suberate where n has a value of 6.

Those skilled in the art will recognize that a wide variety of bifunctional spacer compounds may be used in place of the above disuccinimidyl species and will prove effective in immobilizing biochemical blocking compounds on the surfaces of supports. Examples of homobifunctional spacer compounds that would react with an amine on the surface modifying compound and an amine on the biochemical compound of the biochemical blocking layer include, but are not limited to: disuccinimidyl suberate; bis(sulfosuccinimidyl) suberate; disuccinimidyl glutarate; dimethyl adipimidate; dimethyl suberimidate; dimethyl pimelimidate; dimethyl 3,3-dithiobispropionimidate; methyl N-succinimidyl adipate; and 1,5-difluoro-2,4-nitrobenzene. Examples of homobifunctional spacer compounds that would react with a sulfhydryl group on the surface modifying compound and a sulfhydryl group on the biochemical compound of the biochemical blocking layer include, but are not limited to: 1,11-bis-maleimidotetraethyleneglycol; bismaleimidohexane; 1,6-hexane-bis-vinylsulfone; 1,8-bis-maleimidotriethylene glycol; 1,4-bis-maleimidobutane; and bismaleimidoethane.

In addition to the homobifunctional spacer compounds presented above, it is possible to use heterobifunctional spacer compounds in the present invention. Examples of bifunctional spacer compounds with one end capable of reacting with an amine and one end capable of reacting with a sulfhydryl include, but are not limited to: N-(-maleimidoundecanoyloxy) sulfosuccinimide ester; succiminidyl-4-(N-maleimidomethyl)cyclohexane-1-carboxy-(6-amido-caproate); N-(-maleimidoundecanoic acid); succinimidyl 4-[p-maleimidophenyl]butyrate; succinimidyl-6[(-maleimidopropionamido) hexanoate]; succinimidyl 4-(N-maleimidomethyl)cyclohexane-1-carboxylate; N-succinimidyl(4-iodoacetyl)aminobenzoate; N-[-maleimidobutyryloxy]succinimide ester; m-maleimidobenzoyl-N-hydroxysuccinimide ester; N-maleimidocaproic acid; N-[-maleimidocaproyloxy]succinimide ester; N-succinimidyl-[4-vinylsulfonyl]benzoate; N-[-maleimidopropyloxy]-succinimide ester; succinimidyl 3-[bromoacetamido] propionate; N-maleimidopropionic acid; N-[-maleimidoacetoxy]succinimide ester; N-succinimidyl S-acetylthiopropionate; and N-succinimidyl iodoacetate. A bifunctional spacer compound with one end capable of reacting with an amine and one end capable of reacting with a carboxyl group includes 1-ethyl-3-(3-dimethylaminopropyl) carbodiimide hydrochloride. An example of a heterobifunctional spacer compound with one end capable of reacting with a sulfhydryl group and one end capable of reacting with a hydroxyl group includes N-[p-maleimidophenyl]isocyanate.

The receptor compound is preferably reacted with the activated modified surface of the support produced by reaction with the bifunctional spacer compound. For example, one of the amine groups, preferably an amine such as an -amino group on a lysine residue, will be reacted with the unreacted end of the bifunctional spacer compound to form a covalent amide bond immobilizing the biochemical blocking compound on the surface of the support.

Figure 21:
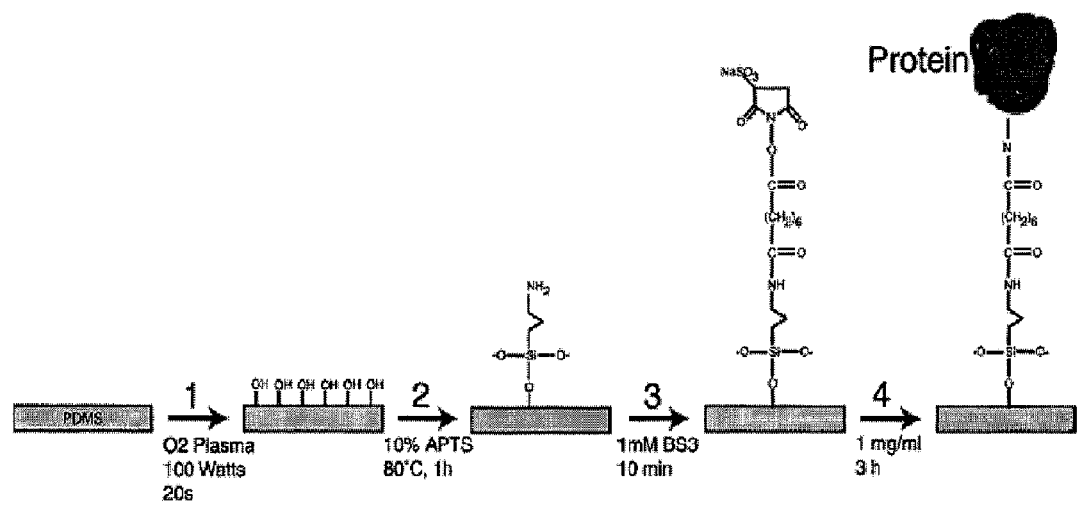
FIG. 21: Schematic depiction of method of preparing affinity stamp.
Figure 22:
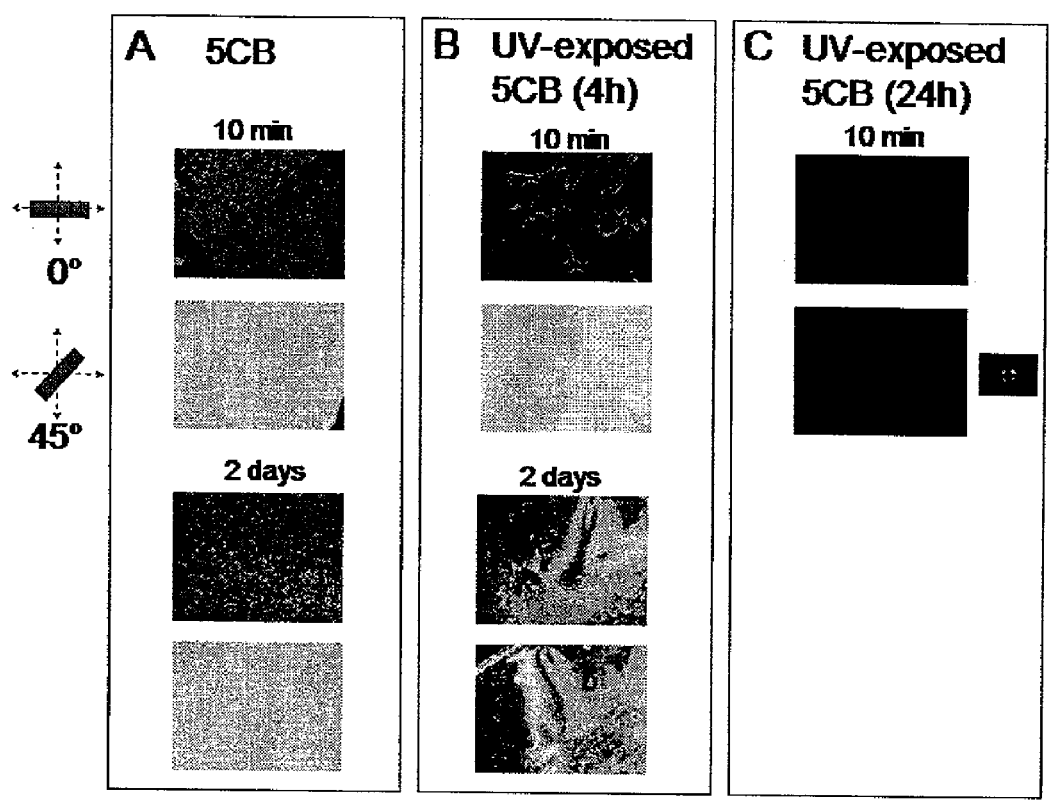
FIG. 22: Optical images of liquid crystal (5CB) sandwiched between octyltrichlorosilane (OTS)-treated glass slide and semi-transparent gold (angle of incidence of 30 degrees) functionalized with amine terminated SAM pretreated with 1 N HCl. A) 5CB. B) 5CB pretreated for 4 hours with UV light. C) 5CB pretreated for 24 hours with UV light. The orientation of the 24 h-UV pretreated 5CB was homeotropic 10 minutes after forming the liquid cell (see FIG. 22C).

In one embodiment, the affinity substrate can be prepared by covalently linking a macromolecule (capture protein) onto a PDMS stamp using conventional cross-linking methods for glass, such that the primary amines on the macromolecule (capture protein) will react with sulfo-NHS esters on the surface to covalently link them to the affinity stamp. For example, as shown in FIG. 21, a PDMS support is functionalized by first oxidizing the surface using an $O_2$ plasma (Step 1). The oxidized surface is then reacted with aminopropyltriethoxysilane (APTS) to make a surface presenting primary amines (Step 2). A bifunctional cross-linker (BS3) is then used to crosslink the primary amine on the surface with the primary amine on the macromolecule (capture protein) (Steps 3 and 4).

The affinity substrate is also referred to as the "affinity stamp". Examples of affinity substrates, their configurations and methods for preparing affinity substrates are also discussed in U.S. patent application Publication Nos. US 2002/0028451, US 2001/0013294 and US 2002/0098364 and U.S. Pat. Nos. 6,096,386, 6,537,499 and 6,596,346, which are incorporated herein by refernce.

Alternatives to PDMS for creating stamps include, but are not limited to, hydrogel (ref. Langmuir 2000, 16, 9944-9946, Langmuir 1998,14 (1 5), 3971-3975), elastomers (siloxane (PDMS), silicone, polyolefin, hydrocarbon rubber, chlorosulfonated polyethylene, polychloroprene, chlorinated polyethylene) (ref. www.dupont-dow.com), rubber, other polymers (polyaniline, polypyrrole) (ref. Synthetic Metals 1997, 84 (1-3), 27-34).

In another preferred embodiment, a cylindrical stamp is used to print biomolecules, such as proteins, peptides, antibodies and other microcontact printed species, on the detection surface. An exemplary support for a cylindrical stamp is a 20 ml liquid scintillation vial, although those skilled in the art will recognize that there are many suitable alternative supports. Cylindrical stamps have been used in the past to permit continuous processing and stamping over large areas (refs 21, 26). Affinity microcontact printing is a variant of microcontact printing in which the surface of the PDMS stamp is chemically functionalized to present a receptor that binds a specific biomolecule (e.g., protein). Forces acting near the contact line of the stamp during its adhesion and removal from a surface may lead to the deposition of proteins (and other microcontact printed species) with a preferred azimuthal orientation. In a preferred embodiment, the azimuthal symmetry of the printed proteins is determined by using liquid crystals. It is known to those skilled in the art that liquid crystals can serve as sensitive probes of the in-plane structure of the surfaces decorated with synthetic polymers, and biological macromolecules such as proteins. In some embodiments, proteins printed by both microcontact printing and affinity microcontact printing orient liquid crystals with preferred azimuthal orientations, and the orientations can be dictated by controlling the azimuthal direction of contact between a cylindrical stamp and a surface. In some particularly preferred embodiments, the methods of the present invention provide ways to organize biomolecules at interfaces, including interfaces that couple biomolecular events to orientational transitions in liquid crystals.

Detection Surface

The detection surface used in the present methods provides a surface on which a ligand or analyte is transferred from the affinity substrate and which permits visualization and detection of the ligand via a liquid crystal. As such, the detection surface can be any surface that anchors liquid crystal in the absence of ligand. Preferably, the detection surface is a self-assembled monolayer deposited on a support, such as metal film, for example obliquely deposited gold. Typically, the metal film will be deposited on a support. Alternatively, the detection surface can be a glass slide coated with aminopropyltriethoxysilane. Similar to the affinity substrate the detection surface can also be patterned. The present invention also contemplates using surfaces other than self-assembled monolayers that are also capable of uniformly anchoring liquid crystal. Examples of such surfaces include rubbed substrates and are discussed in U.S. patent application Publication No. US 2002/0055093, which can lack any binding agent when used with the present methods. This publication is incorporated herein by reference. Other methods that can be used to fabricate the detection surface include photopolymerization, mechanical polishing, oblique deposition of organic and inorganic materials, stretching of deformable substrates, and micromolding and nanomolding. Surfaces that give homeotropic or azimuthally degenerate alignment of liquid crystals can also be used.

Alternative Materials for capture surface In addition to gold, other alternative surface coatings include, but are not limited to, silver, copper, noble and coinage metals metal oxides including titanium oxides, polymers, silicon, and a wide ranges of glasses. A wide variety of substrates can be used, including but not limited to, rubbed polymer films including polyimides, surfaces with topography, surfaces prepared by nanomolding and micromolding, surfaces prepared to orient liquid crystals by treatment with UV light (photo-alignment layers), surfaces treated with polymeric brushes, surfaces stretched to align liquid crystals, rubbed protein films, obliquely deposited organic and inorganic materials, mechanically polished surfaces, inorganic films supporting organic monolayers and multilayers, surfaces on which polymers and polyelectrolytes have been adsorbed, glass surfaces, glass surfaces treated with silane-based monolayers, gold and silver films on organosulfur compounds have been adsorbed. Organosulfur compounds that lead to formation of monolayers presenting carboxylic acids groups, metal carboxylates, ethylene glycol, nitrile groups, ferrocenium, quaternary ammonium, sulfonate, and amine groups can be used. The support for the detection surface of the present invention is not particularly limited as long as the support can uniformly anchor liquid crystal or be treated to uniformly anchor a liquid crystal. Preferred supports include polymers and silica-containing materials that contain hydroxyl groups for reaction with surface modifying compounds or agents. Examples of polymeric supports include, but are not limited to, polystyrene, polycarbonates, and polymethyl methacrylate which are preferably plasma treated to present hydroxyl or carboxylic acid functionalities. Silicone elastomers can also be used. Other materials suitable for use as supports include metal oxides such as, but not limited to, indium oxide, tin oxide, and magnesium oxide and metals such as, but not limited to, gold, silver, and platinum which are preferably reacted with a sulfur-containing compound that contains a reactive functionality such as a hydroxyl or carboxylic acid group. Still other materials that may be used as supports include cellulosic materials such as nitrocellulose, wood, paper, and cardboard and sol-gel materials. Especially preferred supports include glass, quartz, and silica, and most preferred supports include glass slides and silica wafers. Preferably, such supports are cleaned prior to use. Those skilled in the art will recognized that surfaces for use in this invention are not limited to those listed above. When a self-assembled monolayer is used as the detection surface, the SAM can have one or more of the following characteristics:
(1) hydrophilic;
(2) uniformly aligns liquid crystals; and
(3) ligand will not desorb from the SAM, particularly when contacted with liquid crystal or an aqueous buffer.

First, a hydrophilic SAM can be used to increase the transfer of protein from the stamp to the substrate. The mechanism for protein immobilization for microcontact printing is different than the mechanism of protein immobilization by physisorption. The increased transfer of protein to hydrophilic surfaces is believed to be the result of the high surface energy of hydrophilic surfaces exposed to air. Second, a SAM that uniformly aligns liquid crystals on obliquely deposited gold can be used for better detection of bound protein. Third, a SAM that will not allow protein to desorb when contacted with liquid crystal or an aqueous buffer can be used as no desorption in liquid crystal is important for detection. No desorption in an aqueous buffer is desired so that testing of the activity of the stamped protein by binding a second protein from solution might be possible. A preferred SAM is an amine-terminated SAM which fulfills all of the above criteria. Although the exemplified SAMs are hydrophilic because the ligand is hydrophilic, hydrophobic molecules can also be used in the SAM, particularly when the ligand is hydrophobic.

A wide variety of materials can also used as supports for the detection surface. The support for the detection surface of the present invention is not particularly limited as long as the support can uniformly anchor liquid crystal or be treated to uniformly anchor a liquid crystal. Preferred supports include polymers and silica-containing materials that contain hydroxyl groups for reaction with surface modifying compounds or agents. Examples of polymeric supports include, but are not limited to, polystyrene, polycarbonates, and polymethyl methacrylate which are preferably plasma treated to present hydroxyl or carboxylic acid functionalities. Silicone elastomers can also be used. Other materials suitable for use as supports include metal oxides such as, but not limited to, indium oxide, tin oxide, and magnesium oxide and metals such as, but not limited to, gold, silver, and platinum which are preferably reacted with a sulfur-containing compound that contains a reactive functionality such as a hydroxyl or carboxylic acid group. Still other materials that may be used as supports include cellulosic materials such as nitrocellulose, wood, paper, and cardboard and sol-gel materials. Especially preferred supports include glass, quartz, and silica, and most preferred supports include glass slides and silica wafers. Preferably, such supports are cleaned prior to use. For example, glass slides are preferably cleaned by treatment in "piranha solution" (70% $H_2SO_4$/30% $H_2O_2$) for 1 hour and then rinsed with deionized water before drying under a stream of nitrogen. "Piranha solution" requires care in handling as it reacts violently with organic compounds and should not be stored in closed containers.

A preferred support in accordance with the present invention contains a top surface with a layer of obliquely deposited metal on it. Metals that may be used include, but are not limited to, gold, silver, copper, platinum, and palladium. Optionally, an obliquely deposited metal surface such as a gold or silver surface will overlay a surface of titanium or other material that promotes adhesion which has already been deposited on a top surface of the support. The use of the titanium provides better adhesion of the obliquely deposited metal such as silver, or more preferably gold in preparing the metallized surface. Chromium and organic adhesion promoters, such as, but not limited to, aminopropyltrialkoxysilanes may also be utilized in accordance with the present invention. The use of titanium or another adhesion-promoting material is not required as suitable detection surfaces may be prepared without the use of such materials. If an adhesion promoting material is used, a layer of varying thickness may be applied to the underlying support. In some embodiments, approximately 10 Å of Ti is deposited on a support such as a glass slide or plate. In other embodiments, the amount of adhesion-promoting material ranges from 5 Å (0.5 nm) or about 5 Å (0.5 nm) to 20 Å (2.0 nm) or about 20 Å (2.0 nm) while in other embodiments the thickness ranges from 8 Å (0.8 nm) or about 8 Å (0.8 nm) to 15 Å (1.5 nm) or about 15 Å (1.5 nm). In some embodiments, approximately 10 Å (1.0 nm) of aminopropyltrimethoxy-silane is deposited as an adhesion-promoting material. In other embodiments, the thickness of the layer of adhesion promoting material ranges from 5 Å (0.5 nm) or about 5 Å (0.5 nm) to 50 Å (5 nm) or about 50 Å (5 nm). The amount of adhesion-promoting material may be thicker such that in some embodiments, the thickness of the layer of an adhesion-promoting material such as titanium ranges from 5 Å (0.5 nm) or about 5 Å (0.5 nm) to 100 Å (10 nm) or about 100 Å (10 nm).

In some embodiments, a layer of an obliquely deposited metal, preferably gold, is deposited on a cleaned surface of the support by evaporating it at a rate of about 0.2 Å/s (0.02 nm/s) at a pressure of less than or about $5 \times 10^{-6}$ torr without rotation of the sample relative to the incident flux of gold. See Gupta, V. K. et al. Chemistry of Materials, 8, (1996), p. 1366. In other embodiments, a metal such as gold is deposited as described above on a top surface of a support that contains an adhesion-promoting material such as titanium. The layer of a metal such as gold on the metallized surface of the support typically ranges from 50 Å (5 nm) or about 50 Å (5 nm) to 300 Å (30 run) or about 300 Å (30 nm) in thickness. In other embodiments, the layer of a metal such as gold deposited on the surface of the support ranges from 80 Å (8 nm) or about 80 Å (8 nm) to 250 Å (25 nm) or about 250 Å (25 nm) in thickness or from 90 Å (9 nm) or about 90 Å (9 nm) to 200 Å (20 nm) or about 200 Å (20 nm) in thickness. In still other embodiments, the layer of the metal such as gold deposited on the support is from 100 Å (10 nm) or about 100 Å (10 nm) to 200 Å (20 nm) or about 200 Å (20 nm). In some embodiments, a metal such as gold is deposited at an angle of from 30° or about 300 to 60° or about 60°. In other preferred embodiments, a metal such as gold is deposited at an angle of 50° or about 50°. The angle at which the gold is deposited on an underlying support has been found to impact the sensitivity of the detection surface. Therefore, different angles of metal deposition may be preferred depending on the particular application as will be apparent to those skilled in the art. The metallized surface obtained after deposition of the metal is generally an anisotropically rough and semi-transparent surface.

The detection surface is then typically prepared by depositing a self-assembled monolayer on the support. Generally, the SAM is made up of alkane thiol molecules or organosulfur compounds that spontaneously self-assemble on the support. The alkanethiol can be readily adsorbed onto the surface of the support from a solution containing the alkanethiol. In some embodiments, the alkanethiol is present in an alcohol such as ethanol or methanol although other liquids may also be employed in accordance with the invention.

Various alkanethiols may be used to prepare the SAM. Suitable alkanethiols include, but are not limited to, $C_4$ to $C_{20}$ alkanethiols such as butanethiol, pentanethiol, hexanethiol, heptanethiol, octanethiol, nonanethiol, decanethiol, undecanethiol, dodecanethiol, tridecanethiol, tetradecanethiol, pentadecanethiol, hexadecanethiol, heptadecanethiol, octadecanethiol, nonadecanethiol, and eicosanethiol. In various embodiments, the alkanethiols include $C_5$ to $C_{12}$ alkanethiols, $C_5$ to $C_{10}$ alkanethiols, $C_5$ to $C_8$ alkanethiols, or hexanethiol. Those skilled in the art will recognize that dialkyl disulfides, R—S—S—R, may also be used to prepare detection surfaces. Functionalized alkanethiols, such as amine terminated alkanethiols, may also be used and are encompassed in the group of compounds referred to as "alkanethiols". For example, aminoalkanethiols, such as 1-aminoethanethiol, may be used in place of or with ethanethiol to prepare self assembled monolayers in one embodiment of the invention.

The concentration of the alkanethiol in the solution used for alkanethiol adsorption generally ranges from about 1 micromolar to 10 millimolar. When using 1 micromolar solutions, preferred immersion times range from 10 seconds to 24 hours. Particularly preferred immersion times range from 1 minute to 6 hours. Other preferred immersion times range from 30 minutes to 2 hours. Typically, detection surfaces were prepared by contacting metallized surfaces of a support with an ethanolic solution of an alkanethiol at a concentration of 1 mM for a period of at least about 1 hour. Longer or shorter contact times may be used as long as a densely packed monolayer is obtained as will be apparent to those of skill in the art. Generally, the lower the concentration of the alkanethiol in the alkanethiol solution, the longer the metallized surface will be contacted with the alkanethiol solution. Conversely, the higher the concentration of the alkanethiol in the alkanethiol solution, the shorter the metallized surface will be contacted with the alkanethiol.

The alkanethiols are typically adsorbed onto the metallized surface of the support in solutions at temperatures ranging from about 15° C. to about 60° C., from about 20° C. to about 40° C., from about 22° C. to about 40° C., or from about 25° C. to about 37° C. In some embodiments, the temperature range is from about 22° C. to about 28° C., and in other embodiments the temperature is about 25° C. A steady temperature is not necessary, and the temperature may be increased or decreased during the alkanethiol adsorption. Generally, the temperature of the alkanethiol solution is not critical to the preparation of the detection surface. If the DNA recognition fragment has previously been adsorbed onto the metallized surface of the support, then the temperature of alkanethiol adsorption typically ranges from about 20 to about 60° C., from about 22° C. to about 38° C., from about 22° C. to about 28° C., or from about 22° C. to about 26° C. A temperature of at or about 25° C. is particularly suitable for alkanethiol adsorption.

After the alkanethiol has been adsorbed onto the metallized surface of the support, the surface of the support is typically rinsed with ethanol. The ethanol is then usually removed by blowing a stream of $N_2$ or other inert gas over the rinsed surface.

In some embodiments, the detection surface includes an amine-terminated self-assembled monolayer (SAM), for example 1-aminoethanethiol, deposited on obliquely-deposited gold, although SAMs can be deposited on any suitable surface. In some embodiments, the amine SAM is acid treated, such as with 0.1M HCl for 10 seconds, to improve protein transfer and liquid crystal imaging. Amine-terminated SAMs can be used because they possess three characteristics that can be important for some embodiments, namely the SAM (i) is hydrophilic, (ii) it uniformly aligns liquid crystals, and (iii) protein will not desorb from the SAM when contacted with liquid crystal or an aqueous buffer. Other detection surfaces can also be used that have some or all of these characteristics.

Various types of liquid crystals may be used in conjunction with the rubbed substrate structures. Examples of these include both nematic and smectic liquid crystals. Other classes of liquid crystals that may be used in accordance with the invention include, but are not limited to: polymeric liquid crystals, lyotropic liquid crystals, chromonic liquid crystals including disodium chromoglycate, frustrated liquid crystals, thermotropic liquid crystals, columnar liquid crystals, nematic discotic liquid crystals, calamitic nematic liquid crystals, ferroelectric liquid crystals, discoid liquid crystals, and cholesteric liquid crystals. Examples of just some of the liquid crystals that may be used are shown below in Table 1.

TABLE 1

Molecular structure of mesogens suitable for use in Liquid Crystal Assay Devices

| Mesogen | Structure |
|---------|-----------|
| Anisaldazine | $CH_3-O-C_6H_4-CH=N-N=CH-C_6H_4-O-CH_3$ |
| NCB | $C_nH_{2n+1}-C_6H_4-C_6H_4-CN$ |
| CBOOA | $C_9H_{19}-O-C_6H_4-N=CH-C_6H_4-CN$ |
| Comp A | $C_7H_{15}-C_6H_{10}-C_6H_4-COO-C_6H_4-NCS$ |
| Comp B | $C_8H_{17}-O-C_6H_4-O-CO-C_6H_4-O-CH_2-C_6H_4-CN$ |
| $DB_7NO_2$ | $C_7H_{15}-C_6H_4-O-CO-C_6H_4-O-CO-C_6H_4-NO_2$ |
| DOBAMBC | $C_{10}H_{21}-O-C_6H_4-CH=N-C_6H_4-CH=CH-COO-CH_2-CH(CH_3)(C_2H_5)$ |
| nOm<br>n=1, m=4: MBBA<br>n=2, m=4: EBBA | $C_nH_{2n+1}-O-C_6H_4-CH=N-C_6H_4-C_mH_{2m+1}$ |
| nOBA<br>n=8: OOBA<br>n=9: NOBA | $C_nH_{2n+1}-O-C_6H_4-COOH$ |
| nmOBC | $C_nH_{2n+1}-O-CO-C_6H_4-C_6H_4-O-C_mH_{2m+1}$ |
| nOCB | $C_nH_{2n+1}-O-C_6H_4-C_6H_4-CN$ |
| nOSI | $C_nH_{2n+1}-O-C_6H_4-C_6H_4-COO-C_6H_4-CH_2-CH(CH_3)(C_2H_5)$ |
| 98P | $C_3H_7-[CH_2(CH_3)]_5-O-C_6H_4-C_4H_2N_2-C_8H_{17}$ (pyrimidine) |
| PAA | $CH_3-O-C_6H_4-N=N(O)-C_6H_4-O-CH_3$ |
| PYP906 | $C_9H_{19}-C_4H_2N_2-C_6H_4-O-C_6H_{13}$ (pyrimidine) |
| $\bar{n}Sm$ | $C_nH_{2n+1}-O-C_6H_4-CO-S-C_6H_4-C_mH_{2m+1}$ |

Liquid crystals are used in the present invention because of their characteristic properties. Specifically, the present detection systems exploit four important properties of liquid crystals. First, molecules within liquid crystals (mesogens) can communicate their orientations to regions of the bulk liquid crystal, in some cases up to 100 μm away. This long-range communication between mesogens permits changes in the surface to be amplified into changes in orientations of thin films of liquid crystal anchored at the surface. Second, because liquid crystals are fluid, information about the binding of proteins to surfaces is rapidly transduced into the bulk of the liquid crystal (amplification and transduction can occur in a few seconds). Third, because of the optical anisotropy caused by the preferred orientation of mesogens within the liquid crystal, the orientations of bulk liquid crystals can be easily imaged using polarized light microscopy. Fourth, because liquid crystals are sensitive to molecular-level and mesoscale structure of the surface, surfaces can be designed to report the binding of macromolecules and small molecules. Thus the present detection systems provide a general and facile tool for detecting specific ligand-receptor interactions.

A preferred liquid crystal can undergo an alignment transition from planar to homeotropic on the detection surface, which can be caused by the formation of an electrical double layer in the liquid crystal. An example of a liquid crystal that can undergo this transition is 4-cyano-4'-pentylbiphenyl (5CB). By exploiting this transition, detection on surfaces using liquid crystals is not limited to obliquely-deposited gold, but can be extended to other surfaces, such as isotropic gold and glass. An especially preferred liquid crystal composition is 5CB doped with a salt, such as tetrabutylammonium tetrafluoroborate (TBAF). In some preferred procedures, the 5CB can be irradiated with UV light prior to placement on the detection surface. Past studies have demonstrated that irradiation with UV light can lead to increases in the ion content of the liquid crystals.

As shown in the examples, the detection surface with these characteristics allowed for specifically capturing an antibody from solution, printing the antibody onto an amine-terminated SAM, and detecting the presence of the antibody using liquid crystals. By combining affinity microcontact printing with detection using liquid crystals, the capture step can be decoupled from the detection step. Furthermore, surfaces decorated with amine-terminated SAMs provided a planar to homeotropic transition of the liquid crystal alignment. Without limiting the scope of this invention, it is believed this transition is caused by the formation of an electrical double layer in the liquid crystal 5CB. By exploiting this transition, protein detection on surfaces using liquid crystals is not limited to obliquely-deposited gold, but can be extended to other surfaces, such as gold surfaces not deposited at an oblique angle of incidence and glass. The present invention also encompasses the detection surfaces or substrates described herein. Specifically, a detection surface having an amine terminated SAM is covered. The detection surfaces can also be covered with a liquid crystal, typically between 1 micrometer and 100 micrometers thick that can be deposited on the detection surface and can be used without the use of a second substrate. In some embodiments, the liquid crystal can be thermally annealed after contact with the detection substrate in order to maximize the response of the liquid crystal to the presence of the ligand on the substrate Examples of detection surfaces suitable for use in the present invention are disclosed in U.S. patent application Publication Nos. US 2002/0004216, US 2002/0055093 and US 2003/0099993, which are incorporated herein by reference.

Kits

The present invention also provides kits, particularly for performing the detection methods described herein. Kits for use in a liquid crystal assay can include one or more receptors, affinity substrates, detection surfaces, spacing materials, preferably a film, and a liquid crystal compound. In a preferred kit for use in a liquid crystal assay, the surface that uniformly anchors the liquid crystal is another rubbed substrate structure. Such kits may include instructions for the detection of a ligand. Such instructions will typically include directions for incubating the affinity substrate with a sample that possibly contains a target ligand to be detected and contacting the affinity substrate with the detection surface to transfer captured ligand. It will also preferably contain instructions explaining how the presence of the target species is identified and may also contain steps that may be used to determine the concentration of the target species in a sample. Exemplary kit components are discussed herein, particularly in the Examples as shown below.

Preferred kits for use in detecting ligand on a surface typically include a metallized surface; a liquid crystal; a surface that uniformly anchors liquid crystals; and a spacing material such as a film adapted. Any of the kits of the present invention preferably provide either an organosulfur compound or a metallized surface to which a suitable organosulfur compound has already been adsorbed. If the alkanethiol is provided separately, then it may be in the form of a solution such as an ethanolic solution or in a form for addition to a liquid to prepare an alkanethiol solution for adsorption to the metallized surface. The surface that uniformly anchors liquid crystal provided in preferred kits may include any of those described above. Suitable kits of the invention may also include one or more rinsing solution(s) for use after adsorption of an alkanethiol, and after incubation with a sample solution. Such kits may include instructions for the detection and/or instructions for assembling the detection surface or an optical cell.

Following examples provide methods, techniques and apparatus used in the preferred embodiments of the present invention. These examples are useful for illustrative purposes and should not be deemed to limit the scope of the invention.

EXAMPLES

Materials and Methods

Materials. Titanium (99.999%) and gold (99.999%) were obtained from International Advanced Materials (New York, N.Y.). The glass microscope slides were Fisher's Finest, premium grade obtained from Fisher Scientific (Pittsburgh, Pa.). The nematic liquid crystal 4-cyano-4'-pentylbiphenyl (5CB), manufactured by BDH, was purchased from EM Industries (Hawthorne, N.Y.). Octyltrichlorosilane (OTS) and 3-aminopropyltriethoxysilane (APES), and the liquid crystal N-(4-Methoxybenzylidene)-4-butylaniline (MBBA) was purchased from Aldrich (Milwaukee Wis.). All aqueous solutions were preared with high-purity deionized water (18 MΩcm ) using a Milli-Q water purification system (Millipore, Bedford, Ma). All protein solutions were made from phosphate buffered saline (PBS), pH 7.4 (Sigma). The 2-mercaptoethylamine and anti-biotin IgG were also from Sigma (St. Louis, Mo.). PDMS stamps were prepared from Sylgard 184 (Dow Corning, Midland, Mich.). The liquid crystal cells were held together by mini binder clips (Acco, Lincolnshire, Ill.). BS$^3$ (bis[sulfosuccinimidyl] suberate) and biotinylated BSA were from Pierce (Rockford, Ill.).

Cleaning of Substrates. Microscope slides were cleaned sequentially in piranha (70% $H_2SO_4$, 30% $H_2O_2$) and base solutions (70% KOH, 30% $H_2O_2$) using nitrogen to provide agitation (1 h at ~80° C.). Warning: Piranha solution should be handled with extreme caution; in some circumstances, most probably when it has been mixed with significant quantities of an oxidizable organic material, it has detonated unexpectedly. The slides were then rinsed thoroughly in deionized water (18.2 MΩ cm), ethanol, and methanol and dried under a stream of nitrogen. The clean slides were stored in a vacuum oven at 110° C.

Preparation of Octyltrichlorosilane (OTS)-Treated Glass Slides. OTS (octadecyltrichlorosilane) Slides. OTS slides were made according to a procedure described in Brake, J. M.; Abbott, N. L. Langmuir 2002, 18, 6101-6109. Briefly, a solution of 10 mM OTS in n-heptane was passed through a column of aluminum oxide to remove any residual water. Piranha-cleaned glass slides were then immersed into the OTS/n-heptane solution for 30 minutes. The slides were rinsed with methylene chloride and dried under a stream of gaseous $N_2$. The OTS slides were tested for homeotropic alignment by observing the orientation of 5CB sandwiched between two OTS slides. Any slide not inducing homeotropic alignment was discarded.

Alternative Materials for capture surface In addition to gold, other alternative surface coatings include, but are not limited to, silver, metal, metal oxide, polymer, silicon, glass surface In addition to gold, other alternative surface coatings include, but are not limited to, silver, copper, noble and coinage metals metal oxides including titanium oxides, polymers, silicon, and a wide ranges of glasses. A wide variety of substrates can be used, including but not limited to, rubbed polymer films including polyimides, surfaces with topography, surfaces prepared by nanomolding and micromolding, surfaces prepared to orient liquid crystals by treatment with UV light (photo-alignment layers), surfaces treated with polymeric brushes, surfaces stretched to align liquid crystals, rubbed protein films, obliquely deposited organic and inorganic materials, mechanically polished surfaces, inorganic films supporting organic monolayers and multilayers, surfaces on which polymers and polyelectrolytes have been adsorbed, glass surfaces, glass surfaces treated with silane-based monolayers, gold and silver films on organosulfur compounds have been adsorbed. The support for the detection surface of the present invention is not particularly limited as long as the support can uniformly anchor liquid crystal or be treated to uniformly anchor a liquid crystal. Preferred supports include polymers and silica-containing materials that contain hydroxyl groups for reaction with surface modifying compounds or agents. Examples of polymeric supports include, but are not limited to, polystyrene, polycarbonates, and polymethyl methacrylate which are preferably plasma treated to present hydroxyl or carboxylic acid functionalities. Silicone elastomers can also be used. Other materials suitable for use as supports include metal oxides such as, but not limited to, indium oxide, tin oxide, and magnesium oxide and metals such as, but not limited to, gold, silver, and platinum which are preferably reacted with a sulfur-containing compound that contains a reactive functionality such as a hydroxyl or carboxylic acid group. Still other materials that may be used as supports include cellulosic materials such as nitrocellulose, wood, paper, and cardboard and sol-gel materials. Especially preferred supports include glass, quartz, and silica, and most preferred supports include glass slides and silica wafers. Preferably, such supports are cleaned prior to use. Those skilled in the art will recognized that surfaces for use in this invention are not limited to those listed above.

Chemical Functionalization of the Capture Surface

Alternatives to functionalizing a gold or silver surface include, but are not limited to, thiols or disulfides terminated with amine, alcohol, aldehyde, methyl, allyl, carbonyl, carboxyilic, nitrile, nitro, thiol, ethylene glycol, amino-ethylene glycol, or ferrocenyl. In some embodiments, it is desirable to activate the previous functional groups with a reactive moiety, like NHS, SPDP, or maleimide (www.dojindo.com).

Similarly, there are several alternatives available for functionalizing silicon-based or glassy substrates, including but not limited to silanes terminated with amine, alcohol, aldehyde, methyl, allyl, carbonyl, carboxyilic, nitrile, nitro, thiol, ethylene glycol or amino-ethylene glycol. In some embodiments, it is desirable to activate the previous functional groups with a reactive moiety, like NHS, SPDP, or maleimide (www.dojindo.com).

In some preferred embodiments, the choice of surface functionalization chemistry depends on the nature of the ligand to be attached to the surface. The following table presents some exemplary functional groups for use in attaching different biomolecules or compounds with particular functional groups available for attachment to the functionalized surface.

|  | Amine | Thiol | Aldehyde | streptavidinbiotin |
|---|---|---|---|---|
| Biomolecules |  |  |  |  |
| acidic peptides/proteins | − | + | − | (#) |
| neutral peptides/protein | + | (+) | (#) | (#) |
| basic peptides/proteins | + | (+) | (#) | (#) |
| nucleic acids | − | − | − | # |
| polysaccharides | − | − | − | # |
| Functional groups peptides/proteins |  |  |  |  |
| —NH$_2$ | + | # | − | (#) |
| —SH | − | + | − | (#) |
| —COOH | − | (#) | − | (#) |
| —CHO | − | − | # | (#) |
| polysaccharides |  |  |  |  |
| —CHO | − | − | (#) | # |
| —COOH | − | (#) |  |  |

+ recommended,
(+) acceptable,
− unsuitable,
requires ligand modification

The choice of thiol coupling depends on the availability of thiol groups on the ligand. Thiol coupling may not be suitable for strong reducing conditions, since the disulfide bond is unstable under such conditions. Polysaccharides and glycoconjugates have cis-diol and sialic acids which are easily oxidized to aldehydes. Therefore, in some embodiments, aldehyde coupling can be used for these cases. In other embodiments, particularly when neither amine nor thiol coupling is suitable, streptavidin-biotin is a preferred coupling pair.

Typical NHS-EDC Procedure
(1) Solutions of NHS (0.1 M) and EDC (0.4 M) in distilled deionized water are prepared.
(2) Immobilization surface with terminal carboxylic acid groups is equilibrated with PBS.
(3) The surface carboxylic acid groups are transformed into NHS esters by passing a mixture of 0.05 M NHS and 0.20 M EDC in $H_2O$ over the surface for 7 min.
(4) The surface is rinsed with PBS for 2 min.
(5) The solution of the protein or ligand to be immobilized was injected over the surface for 7 min resulting in amide bond formation by displacement of the NHS esters.
(6) The surface is rinsed with PBS, and excess NHS esters are deactivated by washing (5-20 min) with pH 8.6 sodium phosphate buffer (25 mM).

Immobilization of Proteins on PDMS Using 3-Glycidoxypropyltrimethoxysilane

Discussed below are reaction schemes illustrating the steps that are preferably used in the process for covalent immobilization of an amine-terminated receptor onto a PDMS stamp via an amine-initiated nucleophilic ring opening reaction. A PDMS stamp surface is first oxidized using $O_2$ plasma. The oxidized surface is then reacted with 3-glycidoxypropyltrimethoxysilane (GPS) by immersion in a solution of GPS 0.1% v/v in anhydrous toluene for 30 min at 40° C. The surface is then washed several times in anhydrous toluene and cured in an oven at 110° C. for 20 min. Proteins are then covalently attached to the surface epoxy group by placing a drop of protein dissolved in PBS. The surface is incubated for 1-2 hours in a covered Petri dish containing cottons wet with water to keep a constant moisturized environment.

Immobilization of Proteins on PDMS Using 3-(triethoxysilyl)propyl-isocyanate

A PDMS stamp surface is first oxidized using $O_2$ plasma. The oxidized surface is incubated in toluene solution containing 3% w/v of 3-(triethoxysilyl)propyl-isocyanate at 40° C. for 2 hours. The surface is then rinsed with toluene, hexane, and ether, and dried thoroughly with a stream of nitrogen. A droplet of protein dissolved in PBS is placed on an isocyanate derivatized surface. The surface is incubated for 1-2 hours in a covered Petri dish containing cottons wet with water to keep a constant moisturized environment.

Immobilization of Proteins on Thionyl Chloride-Activated Glass or PDMS (1) Prepare a clean glass slide by cleaning with Piranha solution or with concentrated nitric acid. Or a PDMS with a thin silicon oxide layer is prepared by oxidizing the surface with $O_2$ plasma.
(2) A primary amine surface is created by immersing either glass or oxidized PDMS into an aqueous solution of 10% 3-aminopropyltriethoxysilane at 80° C. for 1 hour.
(3) Rinse the surface with water, dry it in an oven, and rinse it with acetone.
(4) Immerse the surface in a solution containing 1% (v/v) triethylamine and 10% (v/) succinic anhydride in acetone.
(5) After reaction is completed (10-20 min at room temperature), rinse the succinamidopropyl glass or PDMS thoroughly with acetone and methylene chloride.
(6) Immerse the surface into thionyl chloride and allow them to react on a heating mantle for 1 hour at 60° C.
(7) Following the reaction, rinse the activated surface with methylene chloride, acetone and water.
(8) Dry the surface at 110° C. and store desiccated at room temperature until required for immobilization.
(9) Equilibrate the thionyl chloride-activated surface in PBS.
(10) Place a drop of antibody overnight at 4° C.
(11) Following immobilization, immerse the surface in 1.0M glycine methyl ester in PBS for 2 hours to block unreacted thionyl chloride-activated sites.
(12) Wash the surface with PBS and store in PBS until use.

Immobilization of Histidine-Tagged Proteins on Nitrilotriacetic Acid (NTA)-Terminated Surface In some embodiments, SAMs are formed on a gold surface by immersing the surface in ethanolic solutions containing 1 mM mixed alkanethiols (NTA-terminated alkanethiols and ethylene glycol-terminated alkanethiol) for more than 12 hours.

(1) After being rinsed in ethanol and dried under nitrogen, the SAMs are immersed in a 40 mM aqueous solution of $NiSO_4$ (pH 7.2) for 1 h.
(2) The SAMs are then rinsed with a PBS solution (pH 8.2) for 10 s and dried with a stream of nitrogen.
(3) Protein binding is carried out by incubation of SAMs in PBS containing 0.1 µM of Histidine-tagged protein.
(4) The substrates are rinsed with PBS (pH 8.2), and either dried under a stream of nitrogen or stored in PBS (pH 7.4) until use.

Immobilization of Proteins by Introduction of Reactive Maleimide Groups (1) The carboxymethylated matrix is equilibrated with 10 mM Hepes, pH 7.4, 150 mM NaCl, and 3.4 mM EDTA (HBS)
(2) The surface is activated by injection of 0.05 M NHS/0.2 M EDC mixture in Milli-Q water for 7 min at the flow rate of 5 µl/min.
(3) After activation of the surface with NHS/EDC, amino groups were generated by injection of 1.0 M ethylene diamine (pH 6.0) for 10 min at 5 µl/min.
(4) To introduce maleimide groups the surface is exposed to 15 mM N-(4-maleimidobutyryloxy)succinimide in HBS/ethanol (1:1) for 30 min at 5 µl/min.
(5) After replacement of the buffer on the flow cell with 10 mM Na acetate, pH 6.0, and 0.1 5 M NaCl (ABS), the protein in ABS is injected for 25 min at 2 µl/min.
(6) Unreacted maleimide groups are blocked by injection of 10 mM dithiothreitol for 2 min at 5 µl/min.
(7) At the end of immobilization, 40 µl of 20 mM Tris-HCl, pH 7.5, 1 M KCl, 1 mM EDTA, and 1 mM DTT was injected at 5 µl/min to wash the surface.

Uniform Deposition of Gold Films. For use in combination with ellipsometry, films of gold with thicknesses of ~500 Å were deposited onto silicon wafers (Silicon Sense, Nashua, N.H.) mounted on rotating planetaries (no preferred direction or angle of incidence) by using an electron beam evaporator (VES-3000-C manufactured by Tek-Vac Industries, Brentwood, N.Y.). The rotation of the substrates on the planetaries ensured that the gold was deposited without a preferred direction of incidence. A layer of titanium (thickness of ~100 Å) was used to promote adhesion between the glass microscope slide and the film of gold. The rates of deposition of gold and titanium were ~0.2 Å/s. The pressure in the evaporator was less than $5 \times 10^{-7}$ Torr during each deposition.

Semi-Transparent Gold. For use in combination with liquid crystals, semitransparent films of gold with thicknesses of ~140 Å were deposited onto clean glass microscope slides mounted on stationary holders using the electron beam evaporator described above. Anisotropic gold (obliquely-deposited gold) was deposited from a fixed angle of incidence of 45° (measured from normal to the surface). Isotropic gold was deposited at a fixed angle of incidence of 0° (measured from normal to the surface). A layer of titanium (thickness of ~55 Å) was used to promote adhesion between the glass and the film of gold.

Amine SAMs. Self-assembled monolayers were formed on the surfaces of gold films by immersion in ethanolic solutions containing 1 mM 2-mercaptoethylamine ($NH_2(CH_2)_2SH$, Sigma). After 6 hours of immersion at room temperature, the slides were removed, rinsed with ethanol, and then dried under a stream of gaseous $N_2$. Some amine-terminated SAMs were pretreated with HCl by immersing the substrate in 0.1 or 1 N HCl solutions for 15 seconds, then removed and dried under a stream of gaseous $N_2$.

Making Affinity Stamps. PDMS stamps were made by casting Sylgard 184 (Dow Corning, Midland, Mich.) on a silicon master made by photolithography. The master was silanized with (tridecafluoro-1,1,2,2,-tetrahydrooctyl)-1-trichlorosilane vapor overnight under vacuum to aid in the release of the PDMS. The PDMS was cured overnight at 80° C. The elastomeric stamp was peeled off giving the negative pattern of the silicon master. The PDMS was cut into 1 cm×1 cm stamps, and then oxidized using PlasmaTherm 1441 RIE (8 sccm, 20 seconds, 100 W) to form a thin silicon oxide layer on the surface. The oxidized PDMS was functionalized with a primary amine by immersing in 10% 3-aminopropyltriethoxysilane (APES; Aldrich) in water at 80° C. for 1 hour. The surface was activated with a NHS ester by exposure to 1 mM $BS^3$ (Bis[sulfosuccinimidyl] suberate, Pierce) for 15 minutes. Biotinylated BSA (Pierce) was covalently immobilized onto the affinity stamp by covering the activated stamp with 2 mg/ml biotinylated BSA in PBS for 2-8 hours.

Alternatives to PDMS for creating stamps include, but are not limited to, hydrogel (ref. *Langmuir* 2000, 16, 9944-9946, *Langmuir* 1998, 14 (15), 3971-3975), elastomers (siloxane (PDMS), silicone, polyolefin, hydrocarbon rubber, chlorosulfonated polyethylene, polychloroprene, chlorinated polyethylene) (ref. www.dupont-dow.com), rubber, other polymers (polyaniline, polypyrrole) (ref. Synthetic Metals 1997, 84 (1-3), 27-34).

Stamping Procedure. The stamp was inked by covering the entire stamp with antibody solution (1 mg/ml in PBS, 5 h). The inked stamp was rinsed with water for 15 s, then dried with $N_2$. The stamp was contacted with the amine-terminated SAM pretreated with HCl for 30 seconds, applying slight pressure for the first 3 seconds. The stamp was then peeled off. When printing from a stamp mounted on a cylindrical support, the inked stamp was attached to a 20 ml scintillation vial using adhesive tape and then rolled slowly over the substrate for an interval of approximately 30 seconds.

Direct Adsorption. Uniformly deposited gold films were decorated with amine-terminated SAMs, then pretreated with 0.1 M HCl. These gold surfaces were then covered with anti-biotin IgG solution (1 mg/ml in PBS, 5 h or 24 h).

Optical Cells. Optical cells were fabricated by pairing a slide stamped with protein with an OTS-treated glass microscope slide. The slides were aligned facing each other. The slides were kept apart by inserting a thin film of Saran Wrap (~12 μm) or Mylar (thickness of ~13 μm) at the edge of the glass microscope slides. The cells were held together by bulldog clips. The cells were heated to ~40° C. by placement on a hot plate. The 5CB, heated into its isotropic phase (>35° C.) within a glass syringe, was dispensed onto the edge of each cell on the hot plate. The thickness of the film of LC (13 μm±2 μm) was measured as described in (**ref37). The 5CB was drawn into the space between the two surfaces by capillary forces. The cell was then slowly cooled from 36° C. to 33° C. over 1 hour in an oven. Upon cooling, the 5CB transitioned from the isotropic to the nematic phase.

Image Capture. Images of the liquid crystals were captured with a CCD camera (DXC-151A, Sony, Park Ridge, N.J.) or a digital camera (Olympus C-2020 Zoom) and frame grabbing software (Mediagrabber, Rasterops Inc., Santa Clara, Calif.) that was attached to a polarized light microscope (BX60, Olympus, Tokyo, Japan). Consistent settings of the microscope light source (50% of maximum intensity, 50% open aperture, 4× or 10× magnification and no condenser) and CCD camera or digital camera (f-stop of 11) (no auto color correction, 1/100th second shutter speed for 10×).

Ellipsometry. Ellipsometric measurements were performed to determine the optical thicknesses of SAMs and films of proteins. The optical thickness reported for each sample is the average of 3 substrates, each substrate measured 3 times at different locations. The measurements were performed using a Rudolph Auto EL ellipsometer (Flanders, N.J.) at a wavelength of 6320 Å and an angle of incidence of 70°. The gold substrates used for ellipsometric measurements were uniformly deposited gold films. The ellipsometric thicknesses of SAMs and immobilized proteins were estimated by using a three-layer model and by assuming a refractive index of 1.45 for both the monolayer and protein.

Experimental Results

Example 1

Design of Surfaces for Affinity Microcontact Printing. The present example used a detection surface having a SAM that possessed the following characteristics: (I) hydrophilic, (II) uniformly aligns liquid crystals, (III) protein will not desorb from the SAM when contacted with liquid crystal or an aqueous buffer. Amine-terminated SAMs are hydrophilic. Harnett, et al. Appl Phys Lett 2000, 76, 2466-2468, Dulcey, et al. Science 1991, 252, 551-554. Prior work has also shown that surfaces coated with primary amines non-specifically adsorb biological materials from solution. Accordingly, amine terminated SAMs were used in the present example. The final characteristic sought for the detection surface was uniform alignment of liquid crystal. To determine if the amine-terminated SAM would uniformly align the liquid crystal 5CB, a sandwich cell with the liquid crystal 5CB sandwiched between two substrates (liquid crystal thickness: ~12 μm) was created. The bottom substrate was an amine-terminated SAM on obliquely-deposited gold. The top substrate was a glass microscope slide functionalized with OTS.

An OTS-treated slide was used for the top surface because OTS has been reported to cause homeotropic alignment of biphenyl LCs, particularly 5CB. Cognard, J. Molecular Crystals and Liquid Crystals 1982, 1-77, and Yang, et al. Microchemistry Proceedings 1994, 441-454. In homeotropic alignment, the average orientation of the long axis of 5CB is normal to the surface. Polarized light transmitted through the liquid crystal sees no anisotropy in the index of refraction. Therefore, the OTS surface will not affect the optical images, and thus only the surface interactions at the gold substrate will be reported in the optical images of the liquid crystal.

FIG. 2A shows the optical image of a sandwich cell with an amine-terminated SAM on one substrate and OTS on the other after 1 hour in a 36° C. oven. At 0° sample orientation on the microscope stage, the least amount of light passing through the crossed polarizers was observed. Sample orientation on the microscope stage is the angle between the direction of incidence of obliquely-deposited gold (maximum roughness of gold surface) and the bottom polarizer on the polarized light microscope. This indicates that the average orientation of the 5CB is in the same direction as one of the polarizers at 0° sample orientation because the polarized light does not see any birefringence and thus is extinguished by the crossed polarizers. At 45° sample orientation, the polarized light sees the greatest amount of birefringence, which leads to the greatest amount of light passing through the crossed polarizers. From this observation, it was concluded that the liquid crystal is uniformly aligned by the amine SAM surface.

By making a wedge-shaped cell (spacer at one end but not the other) with amine-terminated SAMs on both surfaces and observing the change in interference colors upon insertion of a quarter wave plate, the azimuthal orientation of the liquid crystal on the amine-terminated SAM was determined to be in the direction of minimum roughness of the gold surface (orthogonal to direction of maximum roughness). A more detailed description of determining the azimuthal orientation of the liquid crystal is given in Luk, et al. Langmuir 2003, 19, 1671-1680.

In FIG. 2A, many line defects in the liquid crystal alignment, which are domains of the liquid crystal that possess no preferred orientation (isotropic), were also seen,. The cell was heated to determine if it was possible to remove the defects. After heating the sample in FIG. 2A to 36° C. in an oven for 18 hours, then cooling back to room temperature, the alignment of the liquid crystal became homeotropic on both surfaces (FIG. 2B). 36° C. is above the clearing temperature for 5CB (~35° C.). The clearing temperature is the temperature at which the mesogens transition from a liquid crystalline to isotropic phase. The homeotropic alignment was detected by conoscopy. A more detailed description of determining homeotropic alignment by conoscopy is given in Brake, J. M.; Abbott, N. L. Langmuir 2002, 18, 6101-6109. In most samples that are heated at 36° C., the transition from planar to homeotropic alignment occurs after ~8 hours of heating. For samples left at room temperature, the transition from planar to homeotropic alignment occurs after ~6 days. Accordingly, it was concluded that heating the liquid crystal above the clearing temperature decreases the time for the transition from planar to homeotropic alignment.

Past studies have shown that the formation of an electrical double layer at a surface in contact with a liquid crystal can induce homeotropic alignment. For example, contact of 5CB with surfaces presenting sodium carboxylate leads to the transition of 5CB from planar to homeotropic alignment. The ionic species in 5CB that form the electrical double layer are either present at the conclusion of its synthesis, formed by the chemical degradation of the molecules within the liquid crystal or formed by the ionization of entrained water ($H^+$ and $OH^-$). Shah, R. R.; Abbott, N. L. J Phys Chem B 2001, 105, 4936-4950. Past work showed that the electric field induced by the electrical double layer is able to align 5CB in a homeotropic alignment because of its positive dielectric anisotropy (difference in dielectric constant between the long axis and short axis). This conclusion was supported by the observation that a liquid crystal possessing a negative dielectric anisotropy (MBBA), shows no transition to homeotropic alignment. MBBA liquid crystal cells were formed with amine-terminated SAMs and OTS. Even after 21 days of heating the samples above the clearing temperature, then cooling to room temperature, the MBBA liquid crystal showed planar anchoring. This is consistent with the hypothesis that the transition from planar to homeotropic alignment is caused by the formation of an electrical double layer.

It was hypothesized that the formation of the electrical double layer was associated with the presence of ammounium species on the surface. Accordingly, the possible role of ammounium groups by treating the surface with an acid was investigated. Increasing the number of $NH_3+$ groups on the surface will decrease the anchoring energy of the liquid crystal. FIG. 2C shows the optical image of the liquid crystal when the amine-terminated SAM was pretreated with 0.1 N HCl. By comparing FIGS. 2A and 2C, it was observed that the pretreatment of the amine-terminated SAM with 0.1 N HCl reduces the number of defects in the liquid crystal. The decrease in the number of defects seen by pretreating the amine-terminated SAM with 0.1 N HCl is consistent with a reduction in the planar anchoring energy of the liquid crystal, which results in fewer pinned defect lines. The reduction of planar anchoring energy of pretreated surfaces compared to non-pretreated surfaces is consistent with the presence of a more highly charged surface. It follows that pretreating the amine-terminated SAM with an acid improves the uniform alignment of the liquid crystal. In FIG. 2D, a similar transition from planar alignment to homeotropic alignment was seen for the amine-terminated SAM that was pretreated with 0.1 N HCl as the amine-terminated SAM that was not pretreated (FIG. 2B).

The thickness of the amine-terminated SAMs treated with HCl was also measured prior to affinity microcontact printing. For amine-terminated SAMs treated with 0, 0.1, and 1 N HCl, the ellipsometric thickness measured was 1.3, 1.3, and 1.0±0.2 nm, respectively. Since HCl is a gas at room temperature, and the ellipsometric thickness of the amine-terminated SAM does not change for different conctrations of acid treatment, it follows that there is no significant accumulation of salts on the surfaces as a result of the acid treatment.

Example 2

Using Ellipsometry to Confirm Affinity Microcontact Printing of Proteins. The transfer of protein from the affinity stamp to the amine-terminated SAM pretreated with 0.1 N HCl was confirmed by ellipsometry. For ellipsometry, flat PDMS were used stamps. The stamp was first oxidized with an $O_2$ plasma and then functionalized with a primary amine using silane chemistry (aminopropyltriethoxysilane). Biotinylated BSA was then covalently attached to the stamp through Bis[sulfosuccinimidyl] suberate (BS3). The stamp was inked by placing a drop of anti-biotin IgG (1 mg/ml in PBS) on the stamp surface for 5 hours then rinsed with water for 15 seconds. The stamp was then contacted with the amine-terminated SAM for 30 seconds. A change in ellipsometric thickness of 10.8±0.4 nm was measured for stamping the inked anti-biotin IgG from the affinity stamp. Prior work has reported a similar change in ellipsometric thinkness (10 nm) for the binding of anti-biotin IgG to immobilized biotinylated BSA. Kim, S. R.; Abbott, N. L. Langmuir 2002, 18, 5269-5276. In the control experiment, a biotinylated BSA affinity stamp was inked by placing a drop of non-specific antibody (anti-goat IgG, 1 mg/ml in PBS) on the stamp surface for 5 h. The anti-goat IgG inked stamp was then printed in the same manner as the anti-biotin IgG inked stamp. The change in ellipsometric thickness for the control experiment was 2.3±0.2 nm. These results confirm the specific capture and transfer of protein from the affinity stamp to the amine-terminated SAM pretreated with 0.1 N HCl.

Using the same concentration and soak time (1 mg/ml, 5h), the amount of protein transferred by affinity microcontact was compared to printing with direct adsorption. The change in ellipsometric thickness by direct adsorption from solution for anti-biotin IgG is 6.7±0.2 nm. Even for samples soaked for 24 hours, the change in ellipsometric thickness was no greater than 6.7 nm. Without limiting the scope of the invention, it is believed that the greater increase in ellipsometric thickness using affinity microcontact printing is probably the result of higher packing density of the anti-biotin IgG on the affinity stamp compared to direct adsorption of anti-biotin IgG.

To test the effect of acid treatment on the transfer of protein from the affinity stamp, the concentration of the acid treatment was varied and the ellipsometric thickness was measured. The change in ellipsometric thickness for affinity microcontact printing anti-biotin IgG onto amine-terminated SAMs pretreated with 0, 0.1, and 1 N HCl was 7.4, 10.8 and 13.4±0.4 nm respectively. It was concluded that increasing the concentration of the acid pretreatment of the amine-terminated SAMs, increases the amount of protein transferred to the substrate.

Example 3

Orientations of Liquid Crystals on Affinity Microcontact Printed Proteins. The orientations of liquid crystals were next investigated on proteins that were deposited onto amine-terminated SAMs by affinity microcontact printing. The PDMS stamp used for the liquid crystal experiments possessed an array of 300×300 μm square pegs. Using the same procedure described above, the stamp was oxidized and then functionalized with a primary amine. Biotinylated BSA was covalently attached to the stamp. The stamp was then inked by placing a drop of anti-biotin IgG (1 mg/ml in PBS) on the stamp surface for 5 hours then rinsed with water for 15 seconds. The stamp was then contacted with the amine-terminated SAM for 30 seconds. The liquid crystal 5CB was then sandwiched between two surfaces for detection of the protein. The bottom surface of the liquid crystal cell was the amine-terminated SAM pretreated with 0.1N HCl that had been affinity microcontact printed with antibody. The top surface was OTS which gives homeotropic alignment of 5CB.

FIG. 4.1A is an optical image of liquid crystal supported on a surface stamped with anti-biotin IgG and slowly cooled from 36° C. to 33° C. over 1 hour. The sample was cooled slowly because rapid cooling to room temperature results in more defect lines. At 0° sample orientation on the microscope stage, an array of green squares was seen. Sample orientation on the microscope stage is the angle between the direction of incidence of obliquely-deposited gold (maximum roughness of gold surface) and the bottom polarizer on the polarized light microscope. The background at 0° sample orientation is black. At 45° sample orientation, the array of green squares has some dark areas and the background is all green. Because the squares are the same size as the pegs on the affinity stamp, these regions are believed to have immobilized anti-biotin IgG. The dark regions are interpreted to indicate uniform alignment of the liquid crystal on the amine-terminated SAM in the same direction as one of the polarizers. By using a Michel-Levy chart, one can determine the effective birefringence ($\Delta n_{eff}$) of the liquid crystal from the green color. The thickness of the sample is ~12 μm, therefore, from the Michel-Levy chart the effective birefringence of this sample was determined to be ~0.065. The tilt angle of the 5CB on the amine-terminated SAM was calculated by starting with a description of the effective birefringence, $\Delta n_{eff}$, of a tilted birefringent material (Van Doorn, et al. Influence of the Device Parameters on the Performance of Twisted-Nematic Liquid-Crystal Matrix Displays in The Physics and Chemistry of Liquid Crystal Devices; Plenum Press: New York, 1980), $$\Delta n_{eff} = \frac{n_\| \cdot n_\perp}{\sqrt{n_\perp^2 \sin^2(\theta) + n_\|^2 \cdot \cos^2(\theta)}} - n_\perp \quad \text{Equation 1}$$

where $n\| = 1.7110$ and $n\perp = 1.5296$ are the indices of refraction parallel and perpendicular to the optical axis of 5CB, respectively, at 23° C. $\theta$ is the tilt angle of 5CB measured relative to the surface normal.

Equation 2 follows the assumption that the tilt angle of the 5CB varies linearly from the OTS surface ($\theta_1$-0°) to the gold surface decorated with an amine-terminated SAM ($\theta_2$). In Equation 2, d is the thickness of the film of 5CB (~12 μm) and z is the position within the 5CB where z=0 represents the OTS-5CB interface.

$$\theta(z) = \frac{z}{d} \cdot (\theta_2 - \theta_1) + \theta_1 = \frac{z}{d} \cdot \theta_2 \quad \text{Equation 2}$$

By substituting Equation 2 into Equation 1, followed by integration of Equation 1 across the film, the effective birefringence of the 5CB film can be $$\Delta n_{eff} \approx \frac{1}{d} \int_0^d \left( \frac{n_\| \cdot n_\perp}{\sqrt{n_\perp^2 \sin^2\left(\frac{z}{d} \cdot \theta_2\right) + n_\|^2 \cdot \cos^2\left(\frac{z}{d} \cdot \theta_2\right)}} - n_\perp \right) dz \quad \text{Equation 3}$$

estimated using Equation 3.

For an effective birefringence of ~0.065, the tilt of the 5CB on the amine-terminated SAM is calculated to be ~70° from the surface normal.

FIG. 4.1B shows the optical image of the sample in FIG. 4.1A after heating in a 36° C. oven for 8 hours. In FIG. 4.1B, a change in the orientation of the liquid crystal on the amine-terminated SAM not covered with protein from near-planar (~70°) to homeotropic alignment (~0°) was observed. The continuously black background at all sample orientations on the microscope stage is indicative of homeotropic alignment. The homeotropic alignment was also confirmed by conoscopy.

This example also explores how the liquid crystal anchoring changes over time. FIG. 3 shows the time evolution of a sample with anti-biotin IgG printed using affinity microcontact printing. As the time in the oven increases (5 and 7 hours), a change in color of the background (amine-terminated SAM pretreated with 0.1 N HCl) from green to yellow was seen. The change from green to yellow corresponds to a change towards lower order colors on the Michel-Levy chart. Since the thickness of the sample is not changing (~12 μm thick spacers), this change in color was attributed to a change in the effective birefringence from ~0.065 to ~0.02. This corresponds to a change in tilt angle relative to the surface normal from ~70° to ~35° on the amine-terminated SAM. For times greater than 10 hours at 36° C., the liquid crystal alignment is homeotropic (0° tilt angle) in the regions that do not have proteins. FIG. 3.2 is a side by side comparison showing the effect of heating the liquid crystal cell for 10 hours at 37° C. has on the uniformity of the liquid crystal orientation. In A) the optical image was taken 1 hour after making the liquid crystal cell. B) shows the optical image of same liquid crystal cell after heating the sample at 37° C. for 10 hours. As discussed above, it is believed that this transition from planar to homeotropic alignment on the amine-terminated SAM is caused by the formation of an electrical double layer.

To confirm that the optical contrast seen in FIG. 3 was due to anti-biotin IgG specifically binding to biotinylated BSA and transferring to the gold substrate, a control experiment was performed. In the control experiment, a biotinylated BSA affinity stamp was inked by placing a drop of non-specific antibody (anti-goat IgG, 1 mg/ml in PBS) on the stamp surface for 5 h. The anti-goat IgG inked stamp was then printed in the same manner as the anti-biotin IgG inked stamp. FIG. 4.1C shows the optical image of the control experiment. At 0° sample orientation, the entire image is dark. At 45° sample orientation, the entire image is green. The regions that were contacted by the stamp show the same liquid crystal alignment as those regions that were not contacted by the affinity stamp. This result supports the conclusion that the contrast seen in FIG. 3 is due to anti-biotin IgG printed on the surface.

FIG. 4.1D shows the optical image of the sample in FIG. 4.1C after heating in a 36° C. oven for 8 hours. Again a transition from planar to homeotropic alignment was observed, which was confirmed by conoscopy.

From the results in FIG. 4, it was concluded that antibodies can specifically be captured and printed onto gold substrates decorated with amine-terminated SAMs pretreated with 0.1N HCl, and detect the presence of the specific antibody using liquid crystals. FIG. 4.2 shows a side by side comparison of the specific capture against the control.

Example 4

Orientational Response of the Liquid Crystal to Microcontact Printed Proteins. Detailed observation of FIGS. 3 and 4 indicates some uniformity in the liquid crystal response inside the regions of affinity microcontact printed proteins. It was hypothesized that affinity microcontact printing might be providing protein orientation. In order to investigate the possibility of protein orientation, the liquid crystal response to affinity microcontact printed proteins and microcontact printed proteins was compared. It was believed that the liquid crystal response to microcontact printed proteins would be less uniform due to less orientation of the proteins. From FIG. 5.1, it can be seen that the response of the liquid crystal is very similar for both affinity microcontact printing and microcontact printing. At 0° and 90° sample orientation, the background is black and the squares are green. As the sample is rotated on the microscope stage, it was observed that the green squares turn darker, with a maximum in darkness at ~60° sample orientation. The background is brightest at ~45° sample orientation. It follows that the stamped protein (affinity microcontact printed or microcontact printed) is providing some orientation to the liquid crystal and that the liquid crystal response to affinity microcontact printed proteins and microcontact printed proteins is very similar. FIG. 5.2 is a comparison of the liquid crystal images for IgGs stamped using affinity contact printing and microcontact printing. In FIG. 5.2A, the regions with proteins that were affinity contact printed are fairly uniform in their azimuthal orientation. In FIG. 5.2B, the regions with proteins that were microcontact printed are random in their azimuthal orientation.

Example 5

Affinity Microcontact Printing of Proteins on Isotropic Gold and Glass. It was hypothesized that the anisotropic gold might be influencing the uniform orientation of the liquid crystal. To eliminate the influence of the anisotropic gold on the orientation of the liquid crystal in the regions of stamped protein, and thereby determine if the stamped protein can orient the liquid crystal, microcontact printing onto isotropic gold and glass was performed. The isotropic gold is deposited with an angle of incidence of 0° from normal, which gives no anisotropy, and thereby, no uniform orientation to the liquid crystal. The isotropic gold was functionalized with the same amine-terminated SAM, then pretreated with 0.1 N HCl. Anti-biotin IgG was microcontact printed onto this surface and imaged with liquid crystals. The response of the liquid crystal was very similar to the response shown in FIGS. 3, 4A, and 5. Anti-biotin IgG was also microcontact printed onto glass that was functionalized using aminopropyltriethoxysilane. At short times (<20 hours), the response of the liquid crystal in regions of stamped protein was similar to the regions without stamped protein (non-uniform, planar alignment). At longer times (>20 hours), the regions of stamped protein became more apparent because the background was transitioning towards homeotropic alignment (like FIG. 3). The complete transition to homeotropic alignment was much slower for the glass than the gold (~8 hours versus ~8 days). Therefore, there is no evidence that the stamped protein is providing some orientation to the liquid crystal. However, the conclusion follows that by exploiting the transition to homeotropic alignment on amine-terminated monolayers, protein detection using liquid crystals is not limited to obliquely-deposited gold, but can also be performed on isotropic gold and glass functionalized with primary amines.

Example 6

Reusing Affinity Stamps. Prior work has shown that affinity stamps are reusable. Bernard, et al. Nat Biotechnol 2001, 19, 866-869. To test the reusability of the biotinylated BSA affinity stamps, the stamp was reloaded (reinked) two more times with anti-biotin IgG. FIG. 6 shows the liquid crystal response to the first, second, and third use of an affinity stamp. Besides the different colors, the images for the first, second, and third use are very similar. Several possible reasons for the different colors were hypothesized. The different colors could be the result of differences in the cell thickness, differences in the acid pretreatment, or differences in the amount of protein on the surface. It was observed that for images taken after 1 hour (not >10 hours as shown in FIG. 6), the background color is the same as the color inside the squares for a given sample. This indicates that the change in color is independent of whether the region has protein or not. It is also possible that the protein is masking the amine SAM from the liquid crystal, and that this masking is the reason why there is no change from planar to homeotropic alignment in the regions possessing protein. Therefore, it is believed that the different colors are the result of small differences in cell thickness. Assuming a constant effective birefringence of 0.065, the differences in cell thickness from the Michel-Levy chart was calculated to be 12±1 μm. Accordingly FIG. 6 demonstrates that the biotinylated BSA affinity stamps are reusable.

The reusability of the biotinylated BSA affinity stamps was also confirmed by ellipsometry. The change in ellipsometric thickness was measured for the first, second, and third use of the stamp to be 10.8, 8.5, and 8.3±0.4 nm respectively. A side-by-side comparison is shown in FIG. 6B. For the control experiment of stamping anti-goat IgG, the change in ellipsometric thickness for the first, second, and third use of the stamp was 2.3, 1.5, and 1.2±0.2 nm respectively. These results confirm the reusability of the affinity stamps. The ellipsometry results also indicate that the amount of non-specifically transferred protein is reduced after the first use of the stamp, which has been observed previously.

In FIG. 7, the transition of the liquid crystal from planar to homeotropic for the regions of the amine SAM treated with 0.1 M HCl that are not covered with protein can be seen. The transition usually occurs ~2 days after making the liquid crystal cell.

Example 7

Examination of conventional procedures used to pattern proteins by affinity microcontact printing.

Affinity stamps were prepared by the covalent attachment of biotinylated bovine serum albumin to the surface of a PDMS stamp (see Materials and Methods). Following incubation of an aqueous solution of anti-biotin IgG on the surface of the stamp, the surface of the stamp was rinsed with aqueous buffer and then contacted with a film of gold that was functionalized with $NH_2(CH_2)_2SH$. The gold films were prepared by physical vapor deposition at an oblique angle of incidence.

The oblique deposition of the gold film leads to the introduction of in-plane structure in the gold film that causes the uniform azimuthal alignment of liquid crystal, as described previously. The stamp was contacted with the surface by placing one edge of the stamp into contact with the surface and lowering the remainder of the stamp into contact. Following contact, the stamp was peeled from the surface in a direction opposite to that used to contact the stamp with the surface. After transfer of the protein, the stamped surface was spaced (using a thin strip of Mylar with thickness of ~13 µm) from a glass slide treated with octyltrichlorosilane (to cause perpendicular or homeotropic anchoring of the liquid crystal), and the nematic liquid crystal 5CB was introduced into the cavity defined by the two surfaces.

FIG. 8A shows a series of polarized light micrographs (transmission mode) of the nematic liquid crystal (LC) 4-cyano-4'pentylbiphenyl (5CB) in contact with the affinity microcontact printed anti-Bi IgG as a function of the orientation of the sample relative to the crossed polars. The ellipsometric thickness of the anti-Bi IgG transferred to the amine-terminated surface was ~10 nm. Inspection of FIG. 8A reveals the optical appearance of the LC to be black in regions of the surface that are free of antibody and green in the square regions of the surface supporting patterned antibody when the azimuthal orientation of the sample relative to the crossed polars is either 0° or 90° (corresponding to alignment of the azimuthal direction of deposition of the gold with either the analyzer or polarizer of the crossed polars). This result suggests that the azimuthal orientation of the liquid crystal on the regions of the surface printed with antibody is different from the azimuthal orientation on the regions of the surface free of antibody. FIG. 8A also shows that rotation of the sample away from 0° and 90° leads to a darkening of the optical appearance of the LC on the printed antibody, with a maximum in darkness occurring at a sample orientation of ~45°. This result suggests that the azimuthal orientation of the LC on the printed antibody is not random but distributed around an azimuthal angle of ~45° with respect to the direction of deposition of the gold. This conclusion is supported by measurements of the intensity of light transmitted through the liquid crystal in regions of the surface supporting affinity microcontact printing antibody and regions free of antibody (FIG. 8C). The inventors determined the preferred azimuthal orientation of the liquid crystal to lie within ±20° of the direction of contact of the stamp with the surface. The inventors also found that microcontact printing of antibody from a PDMS stamp leads to a preferred orientation of LC in contact with the printed antibody (FIGS. 8B and 8D). The inventors conclude that the protein printed (by affinity microcontact printing or by microcontact printing) on the obliquely-deposited gold is providing a locally preferred azimuthal orientation to the liquid crystal and that the response of the liquid crystal to affinity microcontact printed protein and microcontact printed protein is similar.

Example 8

Use of cylindrical stamps to control the direction of contact between the stamp and the surface Whereas the results of Example 7 suggest that both affinity microcontact printing and microcontact printing lead to proteins deposited with preferred azimuthal orientations, the inventors observed differences of ±20° between the apparent direction of contact of the stamp with the surface and the azimuthal orientation of the LC. To better control the direction of contact of the stamp with the surface and thus test its role in dictating the observed azimuthal alignment of the LC, the inventors adopted the use of a cylindrical stamp (FIG. 9 Cylindrical stamps have been used in the past to permit continuous processing and stamping over large areas. In this example, cylindrical stamps were exploited to define the azimuthal molecular-level organization of the patterned species.

Figure 10:
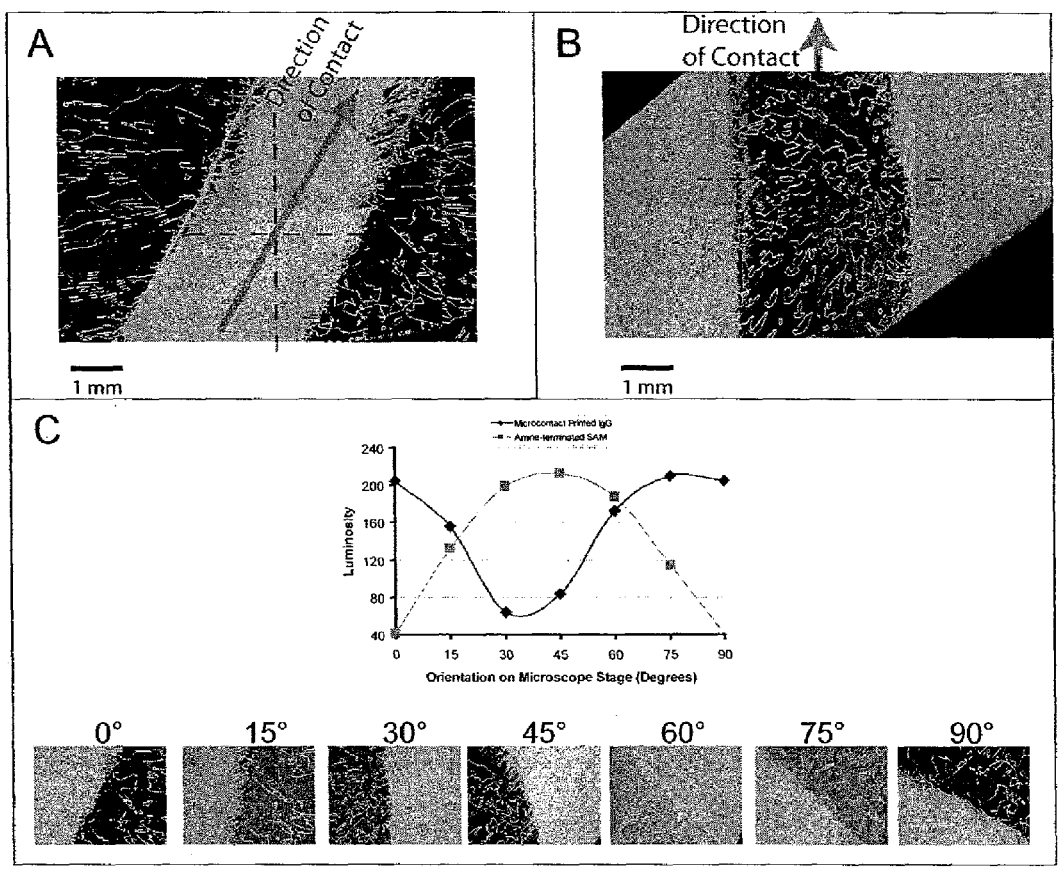
FIG. 10: Optical images (crossed polars) of 5CB in contact with amine-terminated SAMs on which IgGs were microcontact printed by using a PDMS stamp mounted on a cylindrical support. A) 0° sample orientation. B) 45° sample orientation. C) Graph of luminance of liquid crystal in areas of surface presenting microcontact printed IgG and areas of the surface free of printed IgG.
Figure 11:
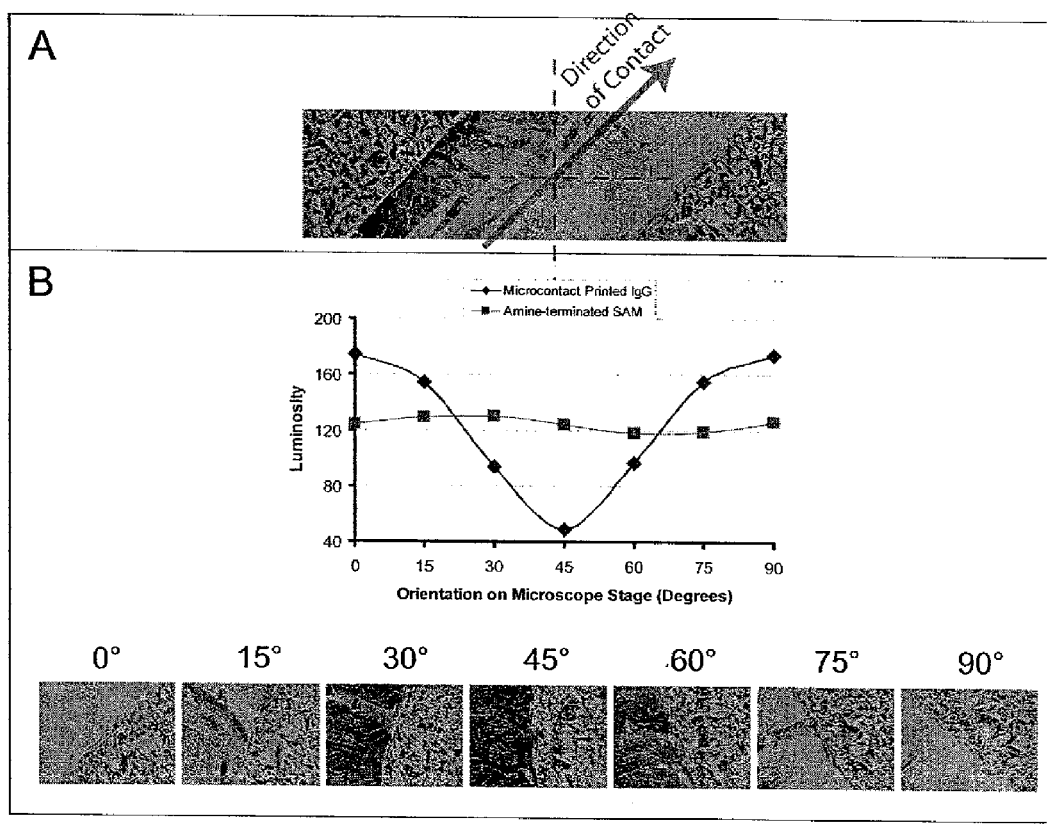
FIG. 11: Optical images (crossed polars) of 5CB in contact with amine-terminated SAMs on which IgGs were microcontact printed using a PDMS stamp mounted on a cylindrical support. The amine-terminated SAM was supported on a gold film deposited at normal incidence. A) 0° sample orientation. B) Graph of luminance of liquid crystal in areas of surface presenting microcontact printed IgG and areas of the surface free of printed IgG.

FIG. 10 shows optical images of nematic 5CB supported on an amine-functionalized gold film (obliquely deposited) on which IgG was microcontact printed using a cylindrical stamp. Inspection of FIGS. 10A and B reveals that the azimuthal orientation of the liquid crystal closely follows the azimuthal direction of motion of the cylindrical stamp during transfer of the antibody to the surface. In the absence of patterned antibody, the azimuthal orientation of the LC follows that templated by the structure of the obliquely deposited gold film. Measurement of the intensity of light transmitted through the LC in the presence and absence of the printed protein confirms these conclusions (FIG. 3C). Comparison of FIG. 10C to FIGS. 8C and 8D also reveals that the uniformity of alignment of the LC, as characterized by the extent of modulation of the intensity of light transmitted through the LC during rotation of the sample, is substantially better when the protein is delivered to the surface from the cylindrical stamp (FIG. 10C) as compared the conventional procedures (FIGS. 8C and 8D). These results, when combined, indicate that the azimuthal orientation of the antibodies can be controlled by using cylindrical stamps to delivery the antibody to the surface.

Whereas the gold films used in the experiments described above were prepared by the oblique deposition of gold, the inventors hypothesized that microcontact printing of IgG should induce a preferred azimuthal orientation of IgG on surfaces that do not possess an underlying anisotropy. The inventors tested this proposition by microcontact printing antibodies onto gold films deposited at normal incidence to the silica substrate. Inspection of FIGS. 11A and B confirms that the LC adopts a random azimuthal orientation on these surfaces in regions free of antibody. In contrast, the LC supported on the printed IgG is oriented in a preferred direction that is defined by the direction of contact of the cylindrical stamp with the gold film. Quantitative measurements of the transmission of polarized light through the LC confirm that there is no preferred orientation of the LC on the gold films in the absence of printed IgG but that there exists a preferred orientation on the regions of the surface decorated with printed IgG (FIG. 11B). These measurements also demonstrate that the uniformity of alignment of the LC is similar on antibody printed onto gold films deposited at normal incidence (FIG. 11B) and oblique incidence (FIG. 10C). Finally, the inventors note that they have also observed the preferred azimuthal orientation of LCs on microcontact printed proteins other than IgGs. For example, microcontact printed BSA causes nematic phases of 5CB to assume a uniform azimuthal orientation.

Example 9

Multiplexed and quantitative protein detection using affinity microcontact printed microarrays To create a microarray for affinity microcontact printing, PDMS stamps are prepared by casting Sylgard 184 on a flat silicon master silanized with (tridecafluoro-1,1,2,2,-tetrahydrooctyl)-1-trichlorosilane.

After curing overnight at 80° C., the PDMS is oxidized using an oxygen plasma (Plasma Etch PE-200, 8 sccm, 20 seconds, 100 W). The oxidized PDMS is functionalized with a primary amine by immersion in an aqueous solution containing 10% APES at 80° C. for 1 hour. The surface is functionalized with a carboxylic acid by incubating in 0.1M Succinic Anhydride in DMF (12 min), then rinsed with DMF and stored in PBS. The stamp is activated with NHS/EDC and rinsed with PBS. The stamp is taped to a glass microscope slide to attach to the GeneMachines OmniGrid Microarrayer. The Microarrayer is used to create four arrays of 25 spots (5 spots per antibody). For example, to detect proteins phosphorylated at different residues, the following antibodies could be arrayed: pan-reactive 111.6 Ab (Lab Vision), and phoshospecific antibodies anti-pY1068 (Biosource), anti-pY1086 (Biosource), anti-pY1148 (Biosource), and anti-pY1173 (Upstate). Glycerol (40%) is added to the antibody solutions to reduce evaporation of the droplet. The PDMS is deactivated with 1% BSA in PBS for 10 min. Small drops of WT (+ and − treatment with EGF) and PAR (+ and − treatment with EGF) membrane extracts are added onto the four antibody arrays separated by a silicon gasket or hydrophobic pen and incubated for 6 hours at 4° C. The stamp is rinsed with PBS with 0.01% Triton X-100, PBS, and water. The stamp is roller-printed onto 30° obliquely-deposited gold functionalized with an amine-terminated monolayer, as described in the preceeding example. The stamped protein is imaged by sandwiching 5CB between the obliquely-deposited gold substrate and an OTS-treated glass slide. Images are taken using a digital camera mounted onto a polarized light microscope. The luminosity of the 5 spots is averaged to give a quantitative characterization of total EGFR and phosphorylated EGFR of each of the membrane extracts.

Example 10

Imaging of Epidermal Growth Factor Receptor by affinity microcontact printing and liquid crystal signal amplification Procedure: Epidermal Growth Factor Receptor (EGFR) is a transmembrane glycoprotein possessing EGF-stimulated protein-tyrosine kinase activity. Its over-expression and mutation have been associated with many cancers. The experiment below demonstrates a label-free analytical method based on affinity microcontact printing (αCP) and liquid crystals (LC) that can detect EGFR from cell membrane extracts or cell lysates using small amounts of sample. Functionalization of the PDMS stamp begins with oxidation of the patterned stamp surface using plasma etching (8 sccm, 20 s, 100 W) to form a thin silicon oxide layer. A primary amine surface was then created by immersing the oxidized PDMS into an aqueous solution containing 10% 3-aminopropyltriethoxysilane at 80° C. for 1 h. Nucleophilic ring opening reaction between the surface amine and 0.1 M succinic anhydride in N,N-dimethylformamide at room temperature for 10 min produces a carboxylic acid-terminated surface. Pan-reactive Anti-EGFR 111.6 (1 mg/ml, Lab Vision) was then immobilized on the carboxylic acid surface using standard NHS-EDC protocol. The EGFR was then affinity captured by placing a small drop (~1 μL) of cell membrane extract purified from either human epidermal carcinoma cells (A431), murine fibroblasts null of the EGFR (B82L-parental), or murine fibroblasts stably expressing wild type human EGFR (B82L-WT), on the antibody-modified surface and incubating for 3-5 h at room temperature. A431 and B82L-WT contain about 1 million EGFR/cell and 100,000 EGFR/cell respectively. The stamp surface is rinsed thoroughly with surfactant solution (0.01%-Triton X-100 in PBS), PBS, and Milli-Q water, and dried under a stream of $N_2$. The affinity-captured EGFR is then transferred to the surface presenting amine-terminated monolayer by contact printing the stamp to the substrate. Amine-terminated self-assembled monolayers (SAMs) are treated with HCl right before the stamping by immersing the substrates into 1 N aqueous HCl for 15 s and then dried under a stream of $N_2$. The stamped surface is observed with a cross-polarized microscope through an optical cell fabricated by sandwiching LC between an amine SAM surface stamped with protein and an octyltrichlorosilane(OTS)-treated glass slide. A schematic representation of this procedure is depicted in FIG. 12A.

Alternative method: Discussed below are reaction schemes illustrating the steps that are preferably used in the process for covalent immobilization of an amine-terminated receptor onto a PDMS stamp via an amine-initiated nucleophilic ring opening reaction. A PDMS stamp surface is first oxidized using $O_2$ plasma. The oxidized surface is then reacted with 3-glycidoxypropyltrimethoxysilane (GPS) by immersion in a solution of GPS 0.1% v/v in anhydrous toluene for 30 min at 40° C. The surface is then washed several times in anhydrous toluene and cured in an oven at 110° C. for 20 min. Anti-EGFR is then covalently attached to the surface epoxy group by placing a drop of protein dissolved in PBS. The surface is incubated for 1-2 hours in a covered Petri dish containing cottons wet with water to keep a constant moisturized environment. The EGFR is then affinity captured by placing a small drop (~1 μL) of cell membrane extract. A schematic representation of this procedure is depicted in FIG. 12B.

Additional Alternative method: A PDMS stamp surface is first oxidized using $O_2$ plasma. The oxidized surface is incubated in toluene solution containing 3% w/v of 3-(triethoxysilyl) propyl-isocyanate at 40° C. for 2 hours. The surface is then rinsed with toluene, hexane, and ether, and dried thoroughly with a stream of nitrogen. A droplet of receptor protein dissolved in PBS is placed on an isocyanate derivatized surface. The surface is incubated for 1-2 hours in a covered Petri dish containing cottons wet with water to keep a constant moisturized environment. The EGFR is then affinity captured by placing a small drop (~1 μL) of cell membrane extract. A schematic representation of this procedure is depicted in FIG. 12C.

Figure 13:
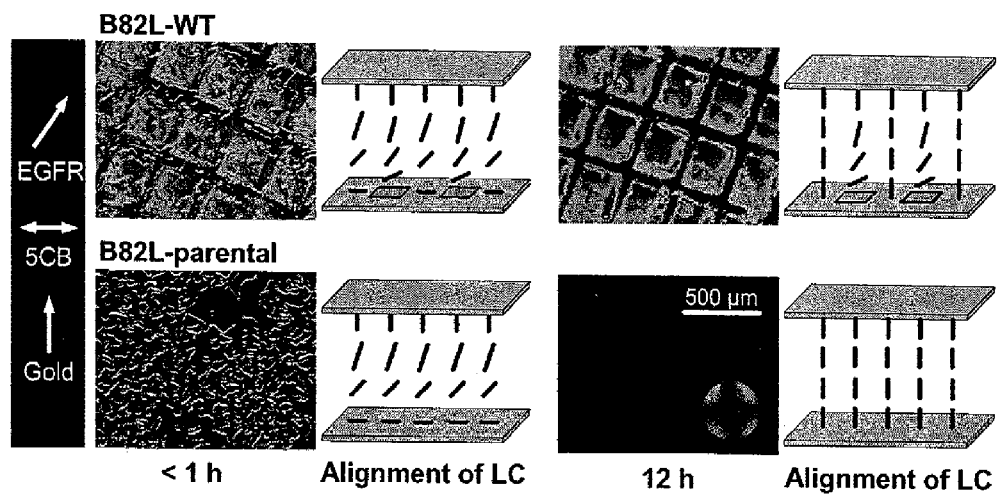
FIG. 13: Images and schematics of nematic 5CB supported on an amine-terminated SAM presenting printed EGFR (epidermal growth factor receptor) affinity-captured from cell membrane extracts either containing EGFR (B82L-WT) or free of EGFR (B82L-parental).

LC results from pan-reactive anti-EGFR (111.6Ab): FIG. 13 shows the optical images (cross-polars) of nematic 5CB supported on an amine-terminated SAM presenting printed EGFR which was affinity-captured from cell membrane extracts (containing EGFR (B82L-WT) and free of EGFR (B82L-parental)). The amine-terminated SAM was supported on an obliquely deposited gold film (bottom surface) and the second surface was an OTS-treated glass slide (top surface). After printing, the substrates were annealed at 36° C. prior to imaging at room temperature. Immediately after printing, A431 samples showed disruption of LC alignment in printed regions while control samples (B82L-parental) did not. After one day of annealing at 36° C., the alignment of LC only on the background region of the A431 sample surface turned homeotropic. The LC pattern persisted more than a week. For the control sample, the entire surface gradually turned homeotropic signifying negligible amounts of protein transferred to the surface by stamping. Homeotropic alignment of LC on B82L-parental samples was confirmed by conoscopy.

Ellipsometry: The transfer of EGFR from affinity stamp to the amine-terminated SAM was confirmed by ellipsometry. The ellipsometric thickness for the affinity captured protein layer from A431 was ~3 nm thicker than B82L-parental. To confirm that the LC patterns were generated by the surface-bound EGFR, a sandwich assay using a second antibody (Clone 199.12, Lab Vision) was performed. 199.12 Ab and 111.6 Ab bind to different ligand binding sites of EGFR. The thickness of the 199.12 Ab layer captured by surface-bound EGFR from A431 was ~1.1 nm. The control experiment with B82L-parental showed no increase in thickness after treatment with 199.12 Ab. The ellipsometric thickness of printed protein layers on amine SAMs supported on flat gold substrates was also measured. The thicknesses of printed protein layers from wild type samples with total protein concentration of 1 µg/µl were ~1 nm greater than parental samples.

Figure 14:
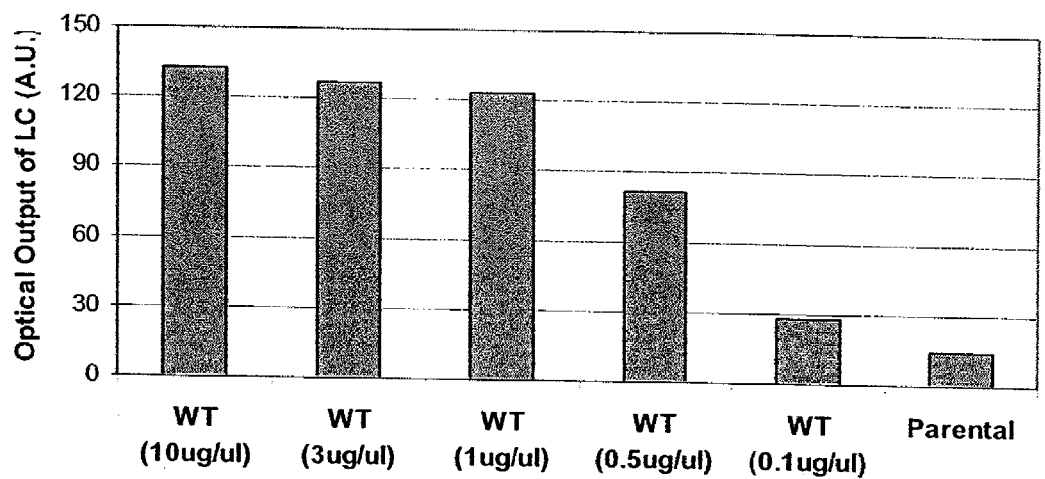
FIG. 14: Representative results demonstrating the quantification of stamped proteins. WT and parental samples were as described in the description of FIG. 13.

Quantification of stamped proteins: The proteins transferred to the amine surface by stamping were quantified by measuring the average optical appearance of LC inside the patterned regions for each case using ADOBE PHOTOSHOP® graphics software. FIG. 14 shows that the wild type samples presented high optical output but the luminosities within the printed region of parental sample was negligible. It also shows that the LC signal gradually decreased with the reduction of total cell protein concentrations. The vanishing of LC signal supports the hypothesis that the LC pattern is due to affinity-captured EGFR printed on the surface.

Figure 15:
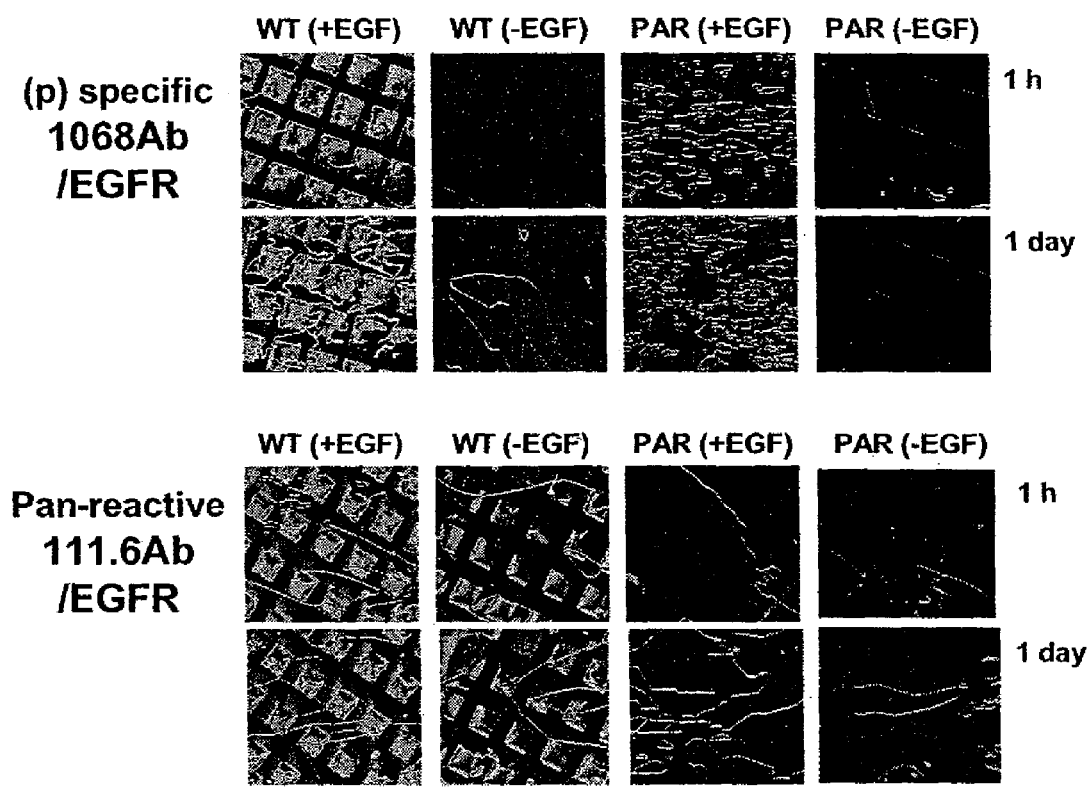
FIG. 15: Optical images of nematic 5CB supported on an amine-terminated SAM presenting printed EGFR affinity-captured from 4 different cell membrane extracts: 1. B82L-WT with EGF treatment (5 minutes) 2. B82L-WT without EGF treatment 3. B82L-parental with EGF treatment (5 minutes) 4. B82L-parental without EGF treatment.
Figure 16:
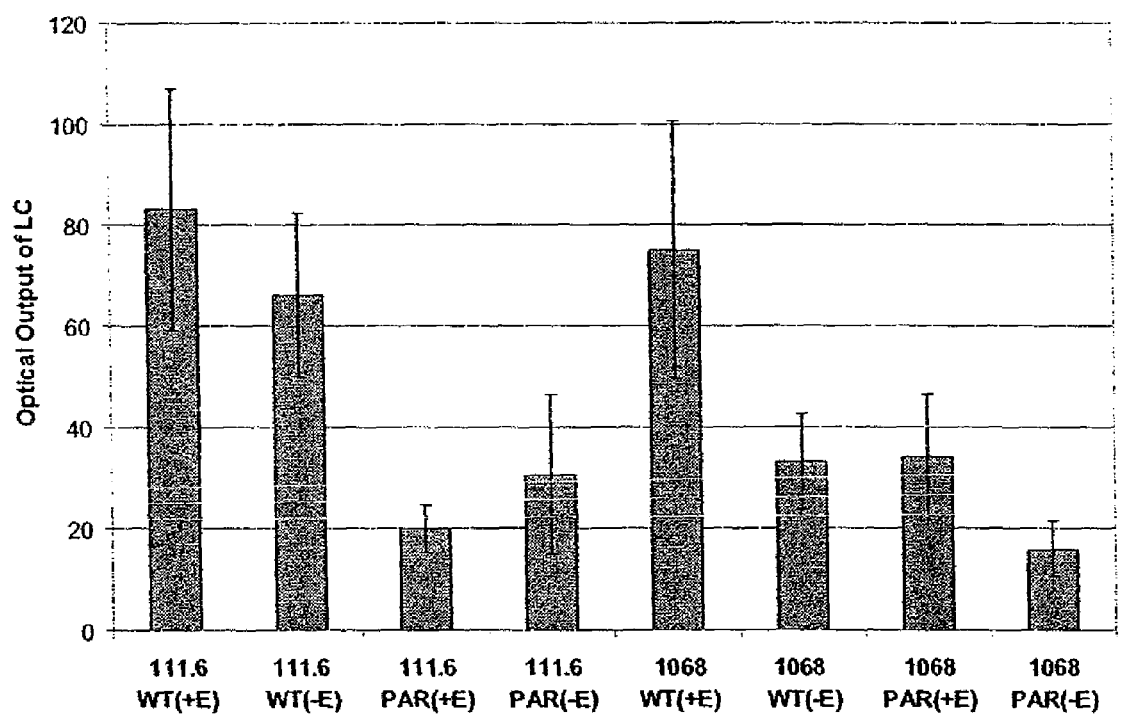
FIG. 16: Quantitative analysis of the average optical response of 5CB in the region of printed EGFR.

Results from phosphospecific anti-EGFR (1068Ab): EGFR tyrosine phosphorylation closely parallels receptor activation. EGF stimulation results in receptor self-phosphorylation on tyrosine kinase domain. The availability of antibodies that exclusively react with various tyrosine-phosphorylated forms of the receptor allows the detection of activated receptor. FIG. 15 shows the optical images of nematic 5CB supported on an amine-terminated SAM presenting printed EGFR which was affinity-captured from 4 different cell membrane extracts: 1. B82L-WT with EGF treatment (5 minutes) 2. B82L-WT without EGF treatment 3. B82L-parental with EGF treatment (5 minutes) 4. B82L-parental without EGF treatment. Pan-reactive anti-EGFR (111.6Ab) shows the disruption of LC alignment for both wild type samples because it cannot tell the difference between the phosphorylated and non-phosphorylated EGFR. However, the phospho-specific anti-EGFR (1068Ab) shows the disruption of LC alignment only for the phosphorylated wild type sample. FIG. 16 shows the average optical response of 5CB in the region of printing for each case.

Inhibition of phosphorylation: Biological signaling processes are often studied by selectively perturbing the network by using specific inhibitor. Current drug discovery efforts for EGFR-associated cancers are mostly focused on inhibition of tyrosine kinase activity. However, these efforts have been hampered by the shortcomings of existing screening methods. To investigate whether this analytical method might be used in combination with inhibitors for this purpose, number of cell membrane extracts were prepared and treated with tyrosine kinase inhibitor (AG1478) and EGF differently (Table 1).

TABLE 1

Wild type and Parental cell membrane extracts with different treatments for a CP-LC detection study

|  | Total Protein (µg/ml) | AG1478 inhibition (minutes) | EGF treatment (minutes) |
| --- | --- | --- | --- |
| WT (1) | 2529 | X | X |
| WT (2) | 1641 | X | 5 |
| WT (3) | 1442 | 30 | X |
| WT (4) | 1923 | 30 | 5 |
| Parental (1) | 2005 | X | X |
| Parental (2) | 2274 | X | 5 |
| Parental (3) | 2086 | 30 | X |
| Parental (4) | 1987 | 30 | 5 |

Figure 17:
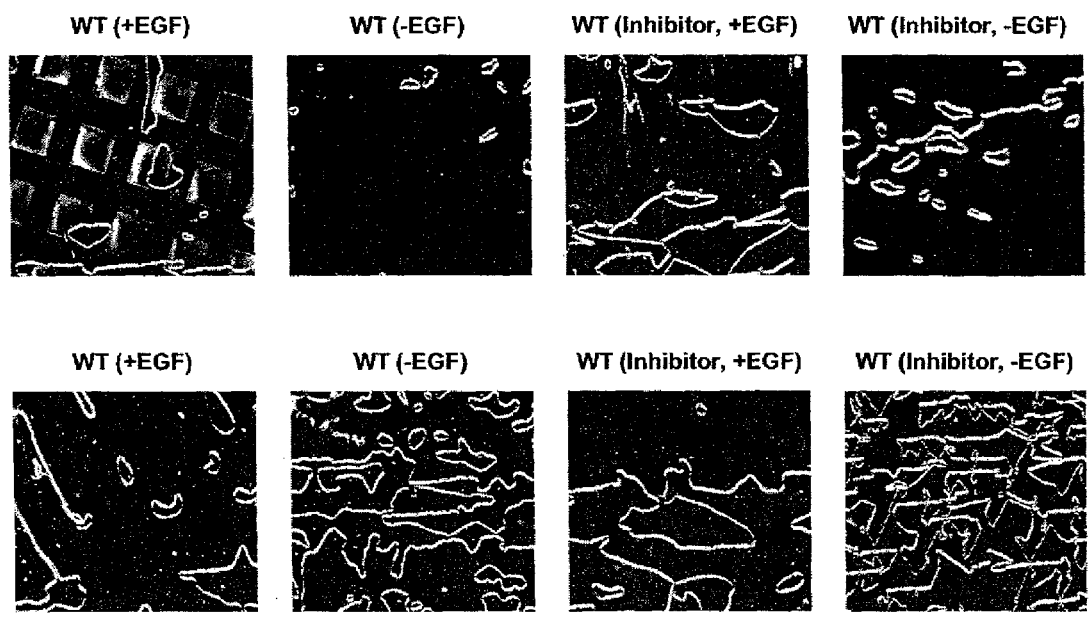
FIG. 17: Optical images of nematic 5CB supported on an amine-terminated SAM presenting printed EGFR which was affinity-captured from 8 different cell membrane extracts using phosphor-specific anti-EGFR 1068Ab.
Figure 18:
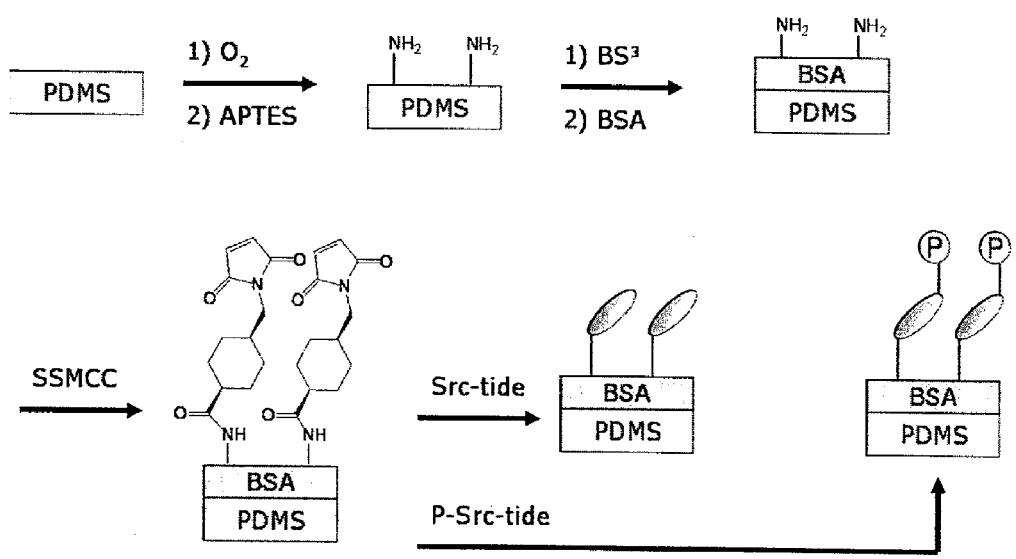
FIG. 18: Scheme for peptide-modification of BSA-coated PDMS stamps.

LC results from inhibitor: FIG. 17 shows the optical images of nematic 5CB supported on an amine-terminated SAM presenting printed EGFR which was affinity-captured from 8 different cell membrane extracts using phosphor-specific anti-EGFR 1068Ab. Only Wild Type (+EGF) sample shows the disruption of LC alignment, which means that the treatment with AG1478 inhibitor successfully block the binding of EGF to EGFR. These results provide the potential for this method to be used for the characterization of the capacity of anti-cancer (tyrosine kinase-directed) agents to specifically attenuate EGFR function.

Example 11

Method for Functionalizing PDMS Stamps with Cysteine-terminated Peptides

To date, no methods have been reported for the functionalization of PDMS stamps with peptide materials. These stamps may have application in the capture of proteins which have affinity for known peptide sequences from complex mixtures (e.g. cell lysate). The prepared stamps must also have surface properties such that efficient protein transfer from the stamp to a desired surface can occur. The present example provides a description of suitable chemistry for covalently attaching peptides to stamp surfaces. The sequence of chemical steps is schematized in FIG. 18.

PDMS stamps were prepared using the Sylgard 184 Silicone Elastomer Kit, and cured for at least 12 hours at 60° C. These stamps were oxidized in an oxygen plasma chamber for 20 seconds, and then immediately immersed in a 10% solution of aminopropyltriethoxysilane (APTES) in dilute acetic acid, pH 6.0. This was warmed to 80° C. for one hour. The stamps were rinsed with water and dried under a stream of nitrogen gas. Next, the stamp surface was treated sequentially with a 1 mM solution of BS3 in water for 15 minutes, and then a 2 mg/mL solution of BSA in PBS buffer for 30 minutes.

The covalently attached BSA has free amine groups from lysine residues not in contact with the stamp. Therefore these free amines could be used to attach peptide molecules via a heterobifunctional linker. The stamps were treated with 2 mM solution of SSMCC in TEA buffer pH 7.0 for 45 minutes. These stamps were rinsed with water, and a 250 µM solution of cysteine-containing peptide in TEA buffer pH 7.0 was applied for 3 hours. These stamps were rinsed with water and then used for subsequent protein capture steps.

Example 12

Capture and Release of Target Anti-pY Antibody Using Peptide Modified Stamps

In order to report the presence of a phosphorylated peptide at the stamp surface, phosphospecific antibodies were used which have affinity for only peptides which contain a phosphorylated tyrosine residue, such as p-Src-tide, which comprises the amino acid sequence IYGEFKKKC (SEQ ID NO: 1) and is a known substrate for the Src protein kinase. See Houseman, B. T., et al., *Langmuir*, 19: 1522-1531 (2003). Post-translationally modified peptide II, referred to as (p) Src-tide, is a synthetic molecule (IpYGEFKKKC (SEQ ID NO: 2)) comprising a phospho-tyrosine (pY) residue that mimics Src protein kinase modification. The sequences of these molecules were confirmed using MALDI-TOF mass spectrometry. Reverse-phase C-18 HPLC analysis demonstrated that each molecule was greater than 98% pure.

The present example demonstrates the selective binding of this antibody protein to stamps which have been modified with the p-Src-tide. Stamps modified with the Src-tide are not observed to capture any antibody.

Figure 19:
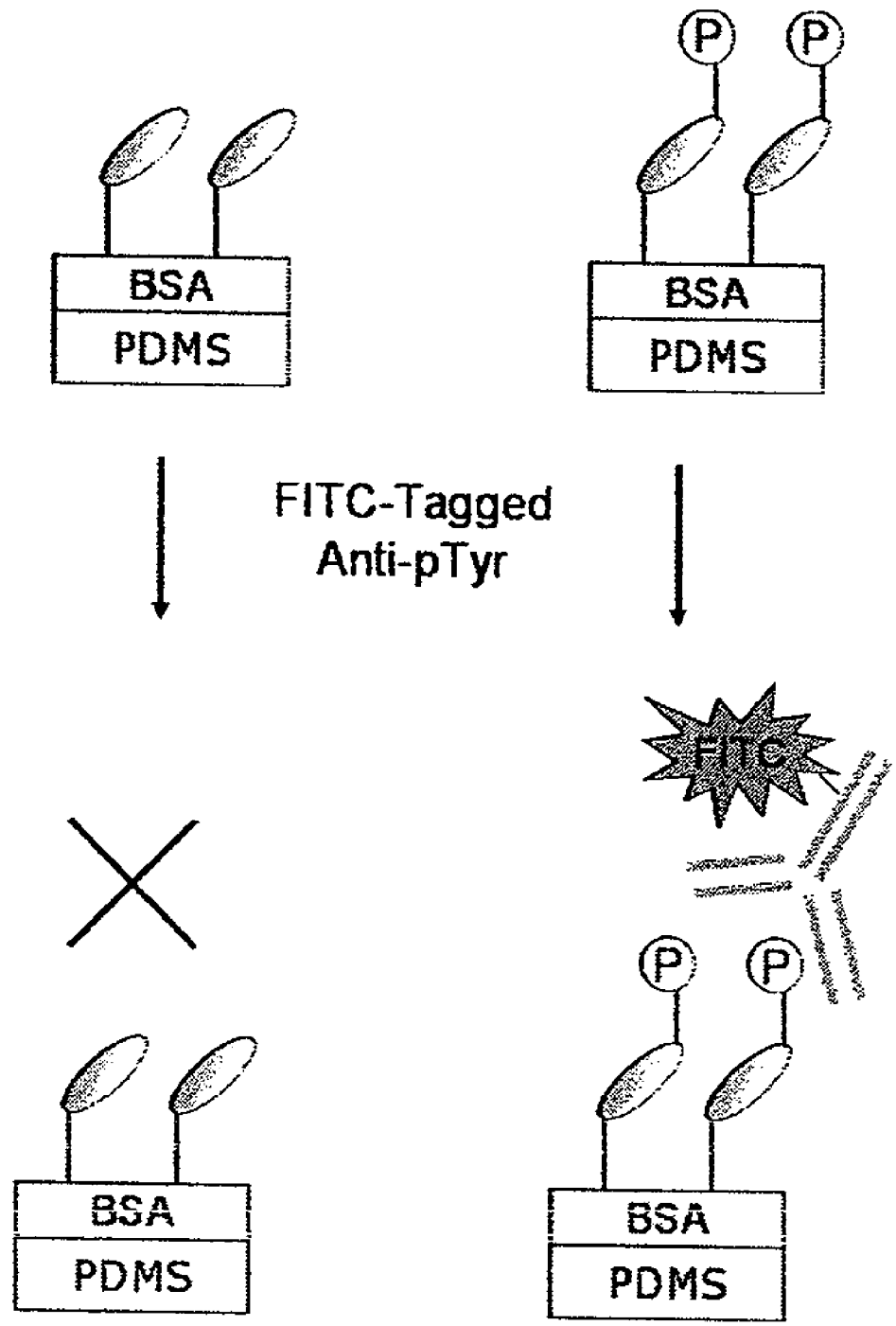
FIG. 19: Scheme for specific capture of antibody.

To monitor this binding event, fluorescein tagged monoclonal anti-phosphotyrosine (Sigma) was used. As illustrated in FIG. 19, both Src-tide and p-Src-tide modified stamps (as prepared according to procedures above) were placed in contact with dilute solutions of FITC-Anti-pY (10 μg/mL, in PBS buffer +0.1%Triton X-100) for 3 hours. These stamps were then rinsed for 10 seconds with PBS buffer +0.1%Triton X-100, then rinsed with water for 1 second and dried under a stream of nitrogen gas.

Experiments were designed to test if the bound antibody could be transferred to SAM surfaces for eventual liquid crystal-based detection. Amine-terminated monolayers were prepared by immersing obliquely deposited gold surfaces in a 2 mM ethanolic solution of 2 mercapto-amine for 4 hours. These gold surfaces were rinsed with copious amounts of ethanol and water, then dried. Then, these SAM surfaces were immersed in 1 N HCl for 15 seconds and blown dry with nitrogen gas.

Dried stamps, after treatment with the FITC-Anti-pY were placed in contact with the SAM surfaces for 30 seconds. The fluorescence intensity of the stamp surface was analyzed in order to observe both 1) the amount of protein initially captured by the stamp and 2) the amount of protein transferred to the SAM surface, as schematized in FIG. 20A.

FIG. 20B depicts two important results when using peptide modified stamps. First, the amount of protein (a phosphospecific antibody) initially bound to the p-Src-tide is significantly higher than the amount of protein adsorbed to the Src-tide modified stamp surface. (Areas pointed to using arrows). Secondly, it demonstrates that it is possible to monitor the amount of protein transferred from the stamp to the detection surface after contact of the stamp with the detection surface. The size of the gold-SAM was about ⅓ the size of the stamp; darkened patches where the fluorescently tagged protein has been transferred.

Example 13

Creating Homeotropic Orientations on Amine-terminated SAMs by UV-pretreatment of Liquid Crystal Experiments were conducted in order to determine if it was possible to pre-treat a liquid crystal preparation to create homeotropic orientations on amine terminated SAMs.

When fresh batches of the 5CB were sandwiched between an OTS-treated glass slide and an amine terminated SAM on a gold surface, as described in previous examples, no transition to homeotropic orientation was observed as it had been for less fresh batches (e.g. a fresh batch was approximately 5 months prior to its expiration date whereas the less fresh batch was less than one month from its expiration date). Generally, pretreatment of the liquid crystal provides uniform behavior of the crystal for a longer duration. Accordingly, after pretreatment, the crystal retains its homeotropic orientation for a longer duration of time. Pretreatment of crystals may therefore be performed, when homeotropic orientation is desirable for longer duration.

FIG. 22A shows the uniform planar alignment of the fresh 5CB which does not turn homeotropic even after 2 weeks. The fresh 5CB was sandwiched between OTS treated glass slide and amine terminated SAM on gold (angle of incidence of 30 degrees) pretreated with 1M HCl.

The fresh 5CB was pretreated with UV light for 4 hours in a glass vial using a Spectroline E-series lamp with filter (model EN280L, Westbury, N.Y.). The lamp illuminates at 1.09 mW/cm$^2$ with a range of wavelengths from 300-450 nm with a peak at 365 nm. The UV-pretreated 5CB was then sandwiched between OTS and amine terminated SAM on gold pretreated with 1M HCl. The orientation of the UV-pretreated 5CB turns partially homeotropic after 2 days (see FIG. 22B).

The fresh 5CB was also pre-treated with UV light for 24 hours in a glass vial using the Spectroline E-series lamp with filter. The 5CB (24 hours UV-pretreatment) was also sandwiched between OTS and amine terminated SAM on gold pretreated with 1M HCl. The orientation of the 24 h-UV pretreated 5CB was homeotropic 10 minutes after forming the liquid cell (see FIG. 22C).

The present compositions and kits can have any or all of the components described herein. Likewise, the present methods can be carried out by performing any of the steps described herein, either alone or in various combinations. One skilled in the art will recognize that all embodiments of the present invention are capable of use with all other appropriate embodiments of the invention described herein. Additionally, one skilled in the art will realize that the present invention also encompasses variations of the present compositions, kits and methods that specifically exclude one or more of the components or steps described herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the invention.

All references, patents and publications disclosed herein are specifically incorporated by reference thereto. Unless otherwise specified, "a," "at least one" or "an" means "one or more".

While preferred embodiments have been illustrated and described, it should be understood that changes and modifications can be made therein in accordance with ordinary skill in the art without departing from the invention in its broader aspects as described herein.

Additional reference is made to the following:
(1) Bernard, et al., Langmuir 1998, 14(9), 2225.
(2) Gupta, V. K.; Skaife, J. J.; Dubrovsky, T. B.; Abbott, N. L. Science 1998, 279, 2077-2080.

(3) Renault, J. P.; Bernard, A.; Juncker, D.; Michel, B.; Bosshard, H. R.; Delamarche, E. Angew Chem Int Edit 2002, 41, 2320-2323.
(4) Gupta, V. K.; Abbott, N. L. Langmuir 1996,12, 2587-2593.
(5) Tan, J. L.; Tien, J.; Chen, C. S. Langmuir 2002,18, 519-523. A. Kumar, G. M. Whitesides, Appl. Phys. Lett. 1993, 63, 2002.
(6) A. Kumar, H. A. Biebuyck, G. M. Whitesides, Langmuir 1994,10, 1498.
(7) P. C. Hidber, W. Helbig, E. Kim, G. M. Whitesides, Langmuir 1996, 12, 1375.
(8) M. Geissler, A. Bernard, A. Bietsch, H. Schmid, B. Michel, E. Delamarche, J. Am. Chem. Soc. 2000, 122, 6303.
(9) L. Yan, X. M. Zhao, G. M. Whitesides, J. Am. Chem. Soc. 1998, 120, 6179.
(10) L. Yan, W. T. S. Huck, X. M. Zhao, G. M. Whitesides, Langmuir 1999, 15, 1208.
(11) J. Lahiri, E. Ostuni, G. M. Whitesides, Langmuir 1999, 15, 2055.
(12) J. P. Renault, A. Bernard, A. Bietsch, B. Michel, H. R. Bosshard, E. Delamarche, M. Kreiter, B. Hecht, U. P. Wild, J. Phys. Chem. B 2003, 107, 703.
(13) K. L. Yang, K. Cadwell, N. L. Abbott, Adv. Mater. 2003, 15, 1819.
(14) J. L. Tan, J. Tien, C. S. Chen, Langmuir 2002, 18, 519.
(15) A. Bernard, J. P. Renault, B. Michel, H. R. Bosshard, E. Delamarche, Adv. Mater. 2000, 12, 1067.
(16) A. Bernard, D. Fitzli, P. Sonderegger, E. Delamarche, B. Michel, H. R. Bosshard, H. Biebuyck, Nat. Biotechnol. 2001, 19, 866.
(17) J. P. Renault, A. Bernard, D. Juncker, B. Michel, H. R. Bosshard, E. Delamarche, Angew. Chem. Int. Ed. 2002, 41, 2320.
(18) M. L. Tingey, S. Wilyana, E. J. Snodgrass, N. L. Abbott, Langmuir 2004, In Press.
(19) L. T. Creagh, A. R. Kmetz, Mol. Cryst. Liq. Cryst. 1973, 24, 59.
(20) N. Mikami, M. Honma, Kobunshi Ronbunshu 1999, 56, 396.
(21) J. M. Geary, J. W. Goodby, A. R. Kmetz, J. S. Patel, J. Appl. Phys. 1987, 62, 4100.
(22) S. R. Kim, N. L. Abbott, Langmuir 2002, 18, 5269.
(23) S. R. Kim, N. L. Abbott, Adv. Mater. 2001, 13, 1445.
(24) S. R. Kim, R. R. Shah, N. L. Abbott, Anal. Chem. 2000, 72, 4646.
(25) Y. N. Xia, D. Qin, G. M. Whitesides, Adv. Mater. 1996, 8, 1015.
(26) J. J. Skaife, J. M. Brake, N. L. Abbott, Langmuir 2001, 17, 5448.
(27) D. L. Everitt, W. J. W. Miller, N. L. Abbott, X. D. Zhu, Physical Rev. B 2000, 62, R4833.
(28) V. K. Gupta, N. L. Abbott, Langmuir 1996, 12, 2587.
(29) L. A. Tercero Espinoza, Y. Y. Luk, K. Schumann, B. A. Israel, N. L. Abbott, Langmuir 2004, 20, 2375.
(30) J. A. Rogers, Z. Bao, A. Makhija, P. Braun, Adv. Mater. 1999, 11, 741.
(31) E. J. Wanless, H. K. Christenson, J. Chem. Phys. 1994, 101, 4260.
(32) V. V. Tsukruk, F. Rinderspacher, V. N. Bliznyuk, Langmuir 1997, 13, 2171.
(33) Y. Gu, F. Nederberg, R. Kange, R. R. Shah, C. J. Hawker, M. Moller, J. L. Hedrich, N. L. Abbott, ChemPhysChem 2002, 3, 448.
(34) O. Yaroshchuk, Y. Zakrevskyy, S. Kumar, J. Kelly, L. C. Chien, J. Lindau, J. Phys. Rev. E 2004, 69, Art No. 011 702 Part 1.
(35) E. Ouskova, Y. Reznikov, S. V. Shiyanovskii, L. Su, J. L. West, O. V. Kuksenok, O. Francescangeli, F. Simoni, Phys. Rev. E 2001, 64, Art. No. 051709 Part 1.
(36) D. H. Chung, Y. Takanishi, K. Ishikawa, H. Takezoe, B. Park, Y. Jung, H. K. Hwang, S. Lee, K. J. Han, S. H. Jang, Jpn J. Appl. Phys 2000, 2 39, L185.
(37) R. R. Shah, N. L. Abbott, J. Phys. Chem. B 2001, 105, 4936.
(38) R. R. Shah, N. L. Abbott, J. Am. Chem. Soc. 1999, 121, 11300.
(39) R. R. Shah, N. L. Abbott, Science 2001, 293, 1296.
(40) Y. Y. Luk, K. L. Yang, K. Cadwell, N. L. Abbott, Surface Science 2004, In Press.
(41) Y. Y. Luk, N. L. Abbott, Science 2003, 301, 623.

All publications are incorporated herein by reference for all purposes.

What is claimed is:

1. A method for detecting a ligand in a sample comprising:
   (a) contacting a sample having a ligand with an affinity substrate, wherein the affinity substrate comprises a receptor capable of specifically binding said ligand, the receptor binding the ligand upon contact with the sample;
   (b) contacting the affinity substrate with a detection surface comprising a hydrophilic, amine-terminated self-assembled monolayer comprising an aminoalkanethiol or aminosilane, wherein the ligand which is bound to the receptor is thereby transferred to the detection surface, and wherein the detection surface is capable of both uniformly anchoring liquid crystal in the absence of the ligand and binding non-specifically to the ligand; and
   (c) detecting the presence of the ligand on the detection surface by contacting the detection surface with a liquid crystal, wherein the presence of the ligand on the detection surface is detected by a change in the orientation of the liquid crystal contacted with the detection surface.

2. The method according to claim 1, further comprising:
   (d) washing the affinity substrate after (a);
   (e) washing the detection surface after (b); or
   (f) both (d) and (e).

3. The method according to claim 1, wherein the receptor or ligand comprises a biomolecule, a biomolecule recognition agent, a peptide, a polypeptide, a protein, a carbohydrate, a toxin, a metal, a heavy metal, a chelator, a pathogen, a virus, a bacterium, a mammalian cell or part of a mammalian cell, a nucleic acid, a nucleic acid analog or mimic, a sugar, an antibody, a Fab, an organic molecule, a lipid, a phospholipid, a drug, a chemical agent, a pesticide or a herbicide.

4. The method according to claim 1, wherein the affinity substrate comprises a polymer, a silica material, a metal or a metal oxide.

5. The method according to claim 1, wherein the affinity substrate comprises polydimethylsiloxane (PDMS).

6. The method according to claim 5, wherein the PDMS of the affinity substrate is further terminated by an antibody which acts as the receptor capable of specifically binding said ligand, the antibody binding the ligand upon contact with the sample.

7. The method according to claim 1, wherein the receptor is bound to the affinity substrate via one or more linking moieties.

8. The method according to claim 1, wherein the amount of ligand present in the sample is quantified.

9. The method according to claim 1, wherein the receptor comprised by the affinity substrate is capable of detecting presence of protein phosphorylation in Epidermal Growth Factor Receptor (EGFR) residues.

10. The method according to claim 1, wherein the self-assembled monolayer is pretreated with an acid prior to (b).

11. The method according to claim 1, wherein contacting the affinity substrate with the detection surface is performed on at least a portion of the affinity substrate that is curved.

12. The method according to claim 1, wherein the detection surface causes homeotropic anchoring in the absence of the transferred ligand.

13. The method according to claim 1, wherein the liquid crystal comprises a nematic liquid crystal, smectic liquid crystal, polymeric liquid crystal, lyotropic liquid crystal, chromonic liquid crystal, frustrated liquid crystals, thermotropic liquid crystal, columnar liquid crystal, nematic discotic liquid crystal, calamitic nematic liquid crystal, ferroelectric liquid crystal, discoid liquid crystal, or cholesteric liquid crystal.

14. The method according to claim 1, wherein the liquid crystal is pretreated by illumination with UV light.

15. The method according to claim 1, wherein the liquid crystal comprises 4-cyano-4'-pentylbiphenyl (5CB), or doped salt thereof.

16. The method according to claim 1, wherein orientation of the liquid crystal is detected optically or electrically.

* * * * *

UNITED STATES PATENT AND TRADEMARK OFFICE
CERTIFICATE OF CORRECTION

| | | |
|---|---|---|
| PATENT NO. | : 8,133,680 B2 | Page 1 of 1 |
| APPLICATION NO. | : 10/711517 | |
| DATED | : March 13, 2012 | |
| INVENTOR(S) | : Nicholas L. Abbott et al. | |

It is certified that error appears in the above-identified patent and that said Letters Patent is hereby corrected as shown below:

Col. 1, Lines 13-17 should be replaced with the following: -- This invention was made with government support under 0079983 awarded by the National Science Foundation. The government has certain rights in the invention. --

Col. 4, Line 50, "methods3" should be -- methods --

Col. 24, Line 47, "preared" should be -- prepared --

Signed and Sealed this
Eighth Day of May, 2012

David J. Kappos
*Director of the United States Patent and Trademark Office*